US012727880B2

(12) United States Patent
Egan

(10) Patent No.: US 12,727,880 B2
(45) **Date of Patent: *Sep. 8, 2026**

(54) ELECTRICALLY WELDABLE SUTURE MATERIAL, AND APPARATUS AND METHOD FOR FORMING WELDED SUTURE LOOPS AND OTHER WELDED STRUCTURES

(71) Applicant: INTUITIVE SURGICAL OPERATIONS, INC., Sunnyvale, CA (US)

(72) Inventor: Thomas D. Egan, Marblehead, MA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/800,806

(22) Filed: Aug. 12, 2024

(65) Prior Publication Data

US 2025/0040926 A1 Feb. 6, 2025

Related U.S. Application Data

(63) Continuation of application No. 17/429,490, filed on Aug. 9, 2021, now Pat. No. 12,114,853, which is a (Continued)

(51) Int. Cl.
*A61B 17/06* (2006.01)
*A61B 17/04* (2006.01)
*B29C 65/34* (2006.01)

(52) U.S. Cl.
CPC .... *A61B 17/06166* (2013.01); *A61B 17/0401* (2013.01); *A61B 17/0469* (2013.01); (Continued)

(58) Field of Classification Search
CPC .......... A61B 17/06166; A61B 17/0401; A61B 17/0469; A61B 17/0482; A61B 17/0487; (Continued)

(56) References Cited

U.S. PATENT DOCUMENTS 3,657,056 A 4/1972 Winston et al.
4,662,068 A 5/1987 Polonsky
(Continued)

FOREIGN PATENT DOCUMENTS

CN 102292033 A 12/2011
CN 105828729 A 8/2016
(Continued)

OTHER PUBLICATIONS

Extended European Search Report for Application No. EP18879322.8, mailed on Jul. 15, 2021, 11 pages.
(Continued)

*Primary Examiner* — Tan-Uyen T Ho
*Assistant Examiner* — Osama Nemer
(74) *Attorney, Agent, or Firm* — Jones Burke, PLLC

(57) ABSTRACT

A device for positioning in the body of an animal, the device comprising a first portion and a second portion that may be positioned in contact with one other, the first portion and the second portion each comprising a biocompatible conductive thermoplastic material, such that when the device is positioned in the body of an animal and electric current flows from the first portion to the second portion, heat is generated by electrical resistance at the point of contact between the first portion and the second portion so as to melt regions of the first portion and the second portion, and when the electric current is thereafter terminated, the melted regions of the first portion and the second portion re-solidify so that a weld is formed between the first portion and the second portion.

24 Claims, 26 Drawing Sheets

Related U.S. Application Data continuation of application No. PCT/US2020/017167, filed on Feb. 7, 2020.

(60) Provisional application No. 62/802,362, filed on Feb. 7, 2019.

(52) U.S. Cl.
CPC .. *B29C 65/3468* (2013.01); *A61B 2017/0409* (2013.01); *A61B 2017/0619* (2013.01)

(58) Field of Classification Search
CPC ............ A61B 17/0483; A61B 17/0491; A61B 17/0467; A61B 17/064; A61B 17/122; A61B 2017/0409; A61B 2017/0619; A61B 2017/0488; A61B 2017/00955; A61B 2017/00526; A61B 2017/00314; A61B 2017/00327; A61B 2017/00398; A61B 2017/0641; B29C 65/3468; B29C 65/3488; B29C 65/3476; B29C 65/3492; B29C 65/3412; B29C 65/3416; B29C 65/7451; B29C 66/861; B29C 66/73141; B29C 66/1122; B29C 66/73921; B29C 66/69; B29C 66/81422; B29C 66/8161; B29C 66/863; B29C 66/71; B29C 66/7212; B29C 66/112; B29C 66/114; B29C 66/30221; B29C 66/50; B29C 66/5346; B29C 66/832; B29C 66/8618; B29K 2995/0005; B29K 2995/006; B29K 2995/0056; B29K 2105/162; B29K 2505/00; B29K 2507/04; B29K 2067/046; B29K 2067/043; B29K 2069/00; B29K 2077/00; B29K 2023/12; B29K 2307/04; A61L 17/00; B29L 2031/709; B29L 2031/753
See application file for complete search history.

(56) References Cited

U.S. PATENT DOCUMENTS 5,059,201 A 10/1991 Asnis
5,133,727 A 7/1992 Bales et al.
5,417,700 A * 5/1995 Egan .................. A61B 17/0469 606/228
5,618,290 A 4/1997 Toy et al.
5,766,186 A 6/1998 Faraz et al.
5,893,880 A * 4/1999 Egan ................ A61B 17/06166 606/228
5,925,064 A 7/1999 Meyers et al.
5,980,538 A 11/1999 Fuchs et al.
6,077,277 A * 6/2000 Mollenauer ............ A61B 17/04 606/139
6,286,746 B1 9/2001 Egan et al.
6,358,271 B1 3/2002 Egan et al.
6,793,750 B2 9/2004 Bittar
7,090,111 B2 8/2006 Egan et al.
7,582,097 B2 * 9/2009 McRury ............. A61B 17/0487 606/139
9,017,346 B2 * 4/2015 Kia .................... A61B 17/0469 606/144
9,168,037 B2 10/2015 Woodard, Jr. et al.
10,245,023 B2 * 4/2019 Kia .................. A61B 17/06166
11,399,822 B2 * 8/2022 Huntington ........ A61B 17/0469
11,446,021 B2 9/2022 Egan
12,114,853 B2 10/2024 Egan
2002/0011508 A1 * 1/2002 Egan ................... B29C 66/1122 606/228
2002/0035371 A1 * 3/2002 Westhaver ......... A61B 17/0483 606/148
2002/0138084 A1 9/2002 Weber
2002/0188304 A1 * 12/2002 Mollenauer ............ A61B 17/04 606/148
2003/0014077 A1 1/2003 Leung et al.
2003/0050649 A1 3/2003 Brock et al.
2003/0114864 A1 * 6/2003 McRury ........... A61B 17/06166 606/148
2004/0073256 A1 4/2004 Marchitto et al.
2004/0172107 A1 9/2004 Fox
2005/0048859 A1 3/2005 Canham et al.
2005/0209639 A1 * 9/2005 Gidwani ................. B29C 66/69 606/228
2006/0265042 A1 11/2006 Catanese, III et al.
2007/0134292 A1 6/2007 Suokas et al.
2008/0039845 A1 2/2008 Bonutti et al.
2008/0086152 A1 4/2008 McKay et al.
2009/0012538 A1 1/2009 Saliman et al.
2009/0062851 A1 3/2009 Rosenblatt
2009/0131979 A1 5/2009 Thompson et al.
2009/0259251 A1 10/2009 Cohen
2010/0101707 A1 * 4/2010 Maiorino .......... B29C 66/81427 156/494
2010/0241229 A1 9/2010 Baehre et al.
2011/0313433 A1 12/2011 Woodard, Jr. et al.
2012/0158023 A1 6/2012 Mitelberg et al.
2013/0092719 A1 4/2013 Kostrzewski
2013/0150842 A1 6/2013 Nau, Jr. et al.
2013/0231701 A1 9/2013 Voss et al.
2013/0253533 A1 9/2013 Bartol et al.
2014/0097554 A1 4/2014 Fenton et al.
2014/0276778 A1 9/2014 McLawhorn et al.
2015/0099959 A1 4/2015 Bonmassar et al.
2015/0250470 A1 9/2015 Vargas
2016/0022332 A1 1/2016 Baehre et al.
2016/0338691 A1 11/2016 Weber et al.
2016/0345563 A1 12/2016 Fenton et al.
2017/0238991 A1 * 8/2017 Worrell .................. H05K 1/034
2018/0228486 A1 * 8/2018 Ravikumar ........ A61B 17/0469
2019/0105032 A1 4/2019 Crews et al.
2022/0079585 A1 3/2022 Egan
2022/0142639 A1 * 5/2022 Egan ...................... B23K 11/28
2023/0050983 A1 2/2023 Egan

FOREIGN PATENT DOCUMENTS

CN 106163423 A 11/2016
CN 111683622 A 9/2020
EP 1009288 A1 6/2000
EP 2075012 A1 7/2009
JP 2003210468 A 7/2003
JP 2010531680 A 9/2010
JP 2013534451 A 9/2013
WO WO-2010053118 A1 5/2010
WO WO-2010085793 A2 7/2010
WO WO-2012006491 A1 1/2012
WO WO-2012007941 A2 1/2012
WO WO-2017039677 A1 3/2017
WO WO-2019099512 A1 5/2019

OTHER PUBLICATIONS

International Search Report and Written Opinion for Application No. PCT/US2018/061043, mailed Mar. 15, 2019, 20 pages.
International Search Report and Written Opinion for Application No. PCT/US2020/017167, mailed Jun. 16, 2020, 13 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP24198746.0, mailed on Dec. 2, 2024, 12 pages.

* cited by examiner

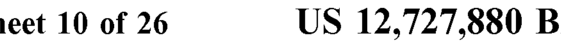
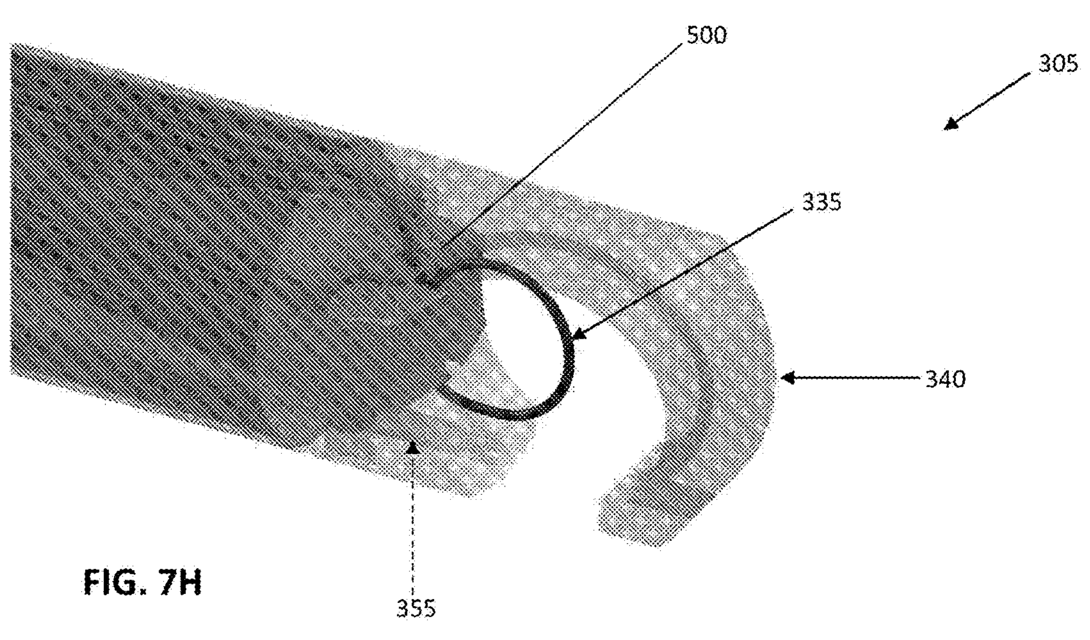
FIG. 7H
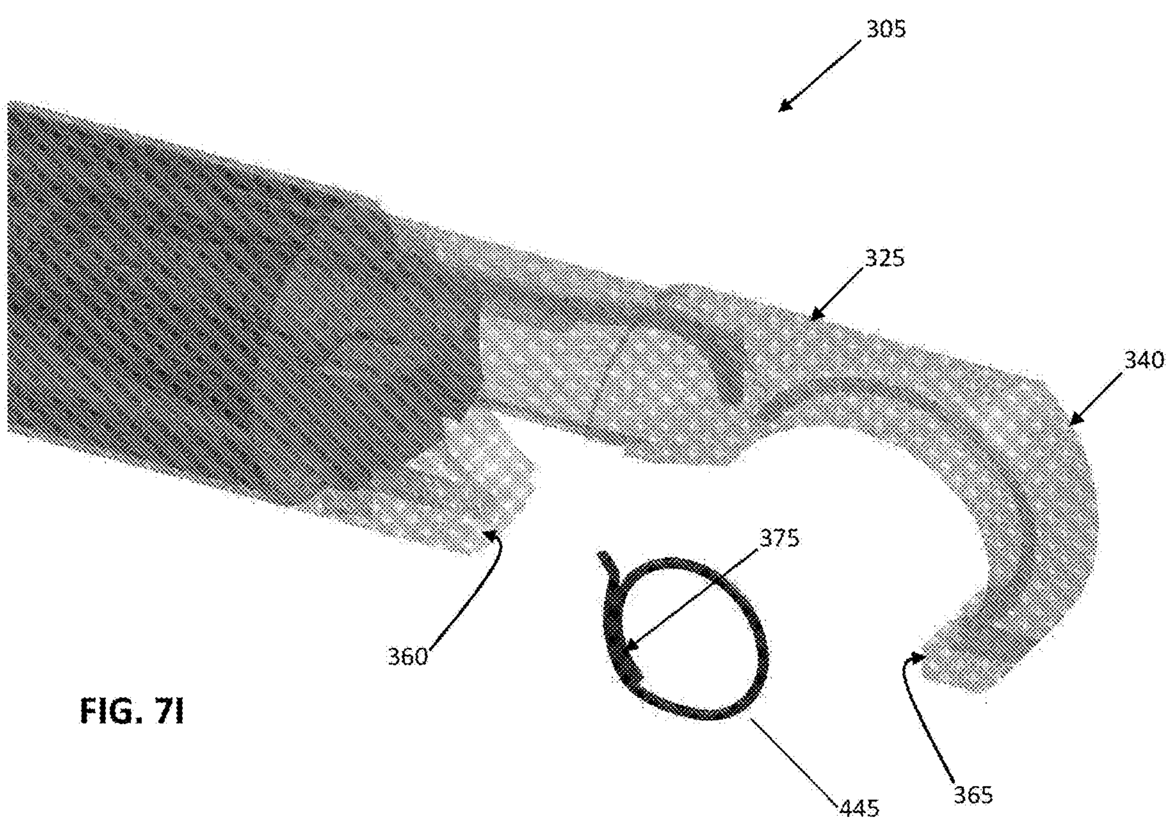
FIG. 7I 901
804
900
805
801

901
804
805
801

901
804
805
905
801

901
804
805
801

901
804
906
805
801

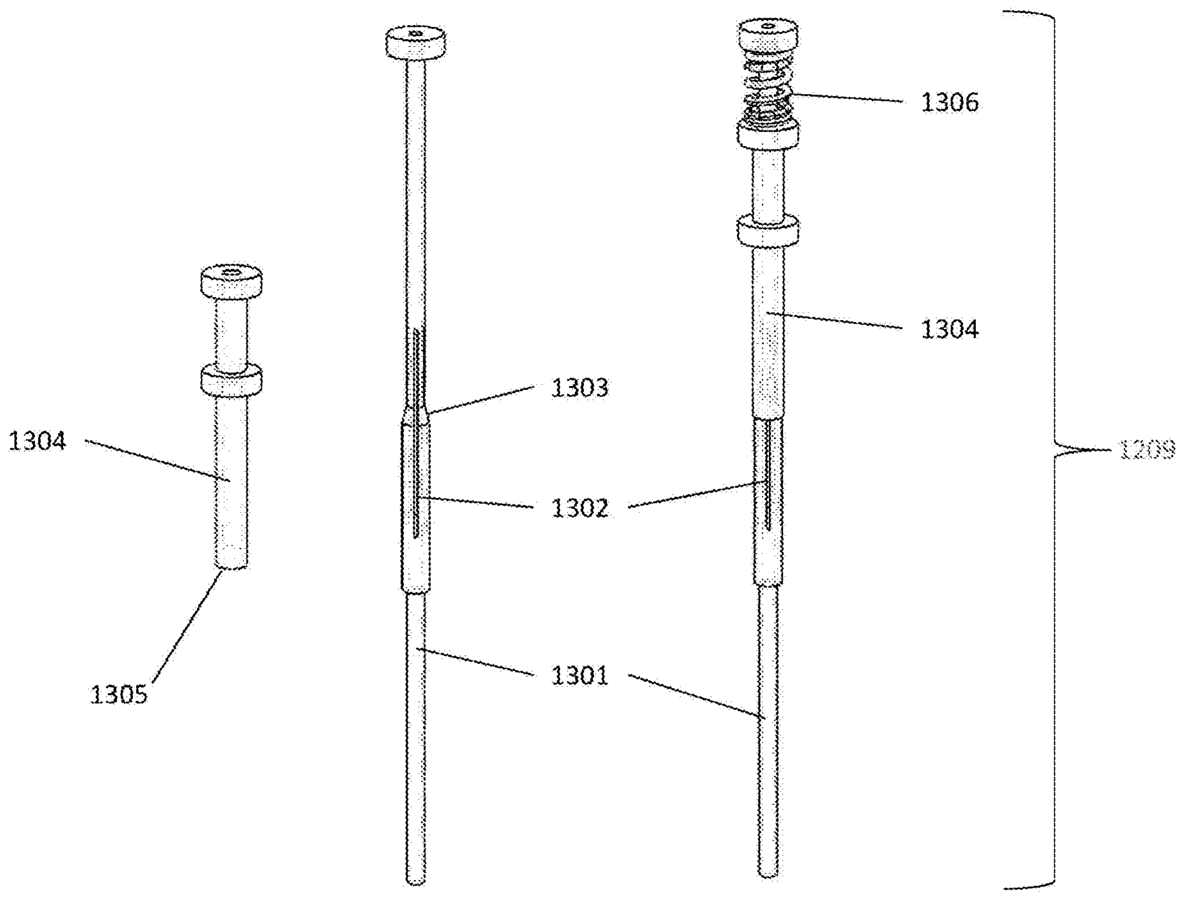
FIG. 12a (Disassembled) FIG. 12b (Assembled)

1204
1402
1401
1306
1304
1305
1303
1301
1208
1203
1209
1404
1403

1306
1208
1203
1403
1204

1203
1208
1209
1403
1404
1405

1306
1208
1304
1305
1303
1302
1203
1406
1407

ELECTRICALLY WELDABLE SUTURE MATERIAL, AND APPARATUS AND METHOD FOR FORMING WELDED SUTURE LOOPS AND OTHER WELDED STRUCTURES

CROSS-REFERENCE TO RELATED APPLICATIONS

This application is a continuation of U.S. application Ser. No. 17/429,490, filed Aug. 9, 2021, which is a continuation of International Application No. PCT/US2020/017167, filed Feb. 7, 2020, which claims the benefit of priority to U.S. Provisional Application No. 62/802,362, filed Feb. 7, 2019, each of which is hereby incorporated by reference in its entirety.

FIELD OF THE INVENTION

This invention relates to the use of electrical energy to fuse polymer materials into useful shapes, and more particularly to the use of electrical energy to fuse polymer materials into useful shapes in the body of an animal (which term is intended to include humans and other mammals), and even more particularly to the use of electrical energy to fuse polymer sutures and other structures for the surgical joining of tissues in a body such as for surgical suturing and vessel or organ closure and/or for surgical ligating of tissues in a body such as for surgical ligating of vessels or organs.

BACKGROUND OF THE INVENTION

In surgical procedures, a suture is typically used to secure the edges of tissue together so as to maintain those tissue edges in proximity to one another until healing is substantially completed. The suture is generally directed through the portions of the tissue to be joined and formed into a single loop or stitch, which is then knotted or otherwise secured (e.g., with a crimped fastener) so as to maintain the edges of the tissue in the appropriate relationship to each other for healing to occur.

In some situations a series of individual, separate stitches of substantially uniform tension are made in tissue. Inasmuch as the stitches are individual and separate from one another, the removal of one stitch does not require the removal of all of the stitches or cause the remaining stitches to loosen. However, each individual stitch requires an individual knot (or some other stitch-closing device, e.g., a crimped fastener) for securing the stitch in place about the wound.

It is sometimes necessary or desirable to close a wound with sutures without having to form knots in the suture or utilize loop-closing devices (e.g., crimped fasteners), such as, for example, in the surgical repair of organs or tissues where access to the repair site is restricted. In these situations, a fused loop of suture can be used to maintain the wound edges in sufficient proximity for a sufficient period of time to allow healing to occur.

Polymer sutures are particularly amenable to various fusing or joining processes, such as, for example, by welding, where sections of the sutures can be fused together upon application of sufficient heat to the sections of the sutures to cause partial melting and fusion of the sections of the sutures.

Efforts have heretofore been made to fuse together segments of polymer suture using (i) the direct application of heat, or (ii) the application of ultrasonic energy.

Unfortunately, effecting welding via the direct application of heat suffers from two significant disadvantages. First, the direct application of heat to sutures in situ may produce undesirable heating of the surrounding tissue. Second, with the direct application of heat to sutures, it is difficult to selectively melt only the interface between the suture segments which are to be welded without melting the entire cross-section of the suture, which can drastically weaken the suture.

For these reasons, it is generally preferred to apply non-thermal energy to the suture material in situ in order to induce localized heating of the suture material in the areas or sections to be fused. In particular, ultrasonic energy may be effectively applied to sections of suture material to induce frictional heating of the sections in order to fuse or weld the sections of the suture together. While such ultrasonic welding of sutures can be an important improvement over direct thermal welding of sutures (i.e., ultrasonic welding melts only the parts of the suture that touch each other and not the whole cross-section of the suture, thereby preserving the strength of the suture), ultrasonic welding suffers from two significant disadvantages of its own. First, ultrasonic welding requires bulky, expensive equipment. Such equipment may not be compatible with certain kinds of surgery and, in any case, increases cost. Second, due to the nature of ultrasonic transducers and waveguides, ultrasonic welding requires straight line access between the energy source and the weld site, so that it is incompatible with curved or flexible instruments.

In addition to the foregoing, in some situations it can be necessary or desirable to ligate tissue such as vessels or organs. Such ligation is typically accomplished using suture which is passed around the tissue and then secured with a knot or closure device (e.g., a crimped fastener). Again, in some circumstances (e.g., where access to the ligation site is restricted), it can be desirable to use a fused loop of suture to effect ligation. And again, in some circumstances, it can be difficult to effect welding using the direct application of heat or the application of ultrasonic energy.

It is, therefore, an object of the present invention to provide a new and improved approach for forming connections (which may also be referred to as joinders or welds) within the body which does not suffer from the problems associated with the prior art.

SUMMARY OF THE INVENTION

The present invention comprises the provision and use of a new and improved approach for forming connections (which may also be referred to as joinders or welds) within the body which does not suffer from the problems associated with the prior art.

Among other things, the present invention comprises the provision and use of a new and improved method and apparatus for producing suture welds of sufficient strength and reliability to replace suture knots or other loop-closure devices.

One important aspect of the present invention comprises the provision and use of a new kind of polymer biomaterial that is strong, biologically compatible, and weldable with electrical energy (i.e., "an electrically weldable polymer").

Another important aspect of the present invention is the provision and use of a method for joining polymer devices in a body to make medically useful structures.

And another important aspect of the present invention is the provision and use of apparatus for delivering and joining medically useful structures in a body.

Still another important aspect of the present invention is the provision and use of novel medically useful structures, including, but not limited to, (i) a fused loop of electrically weldable polymer; (ii) a welded hemostasis clip of electrically weldable polymer; and (iii) a continuously deliverable, staple-like chain of electrically weldable polymer fasteners.

In one form of the present invention, there is provided a device for positioning in the body of an animal, the device comprising a first portion and a second portion that may be positioned in contact with one other, the first portion and the second portion each comprising a biocompatible conductive thermoplastic material, such that when the device is positioned in the body of an animal and electric current flows from the first portion to the second portion, heat is generated by electrical resistance at the point of contact between the first portion and the second portion so as to melt regions of the first portion and the second portion, and when the electric current is thereafter terminated, the melted regions of the first portion and the second portion re-solidify so that a weld is formed between the first portion and the second portion.

In one form of the present invention, there is provided apparatus for forming a weld between a first portion of a biocompatible conductive thermoplastic material and a second portion of a biocompatible conductive thermoplastic material, the apparatus comprising:

- a first electrode;
- a second electrode;
- a structure for holding the first and second electrodes in opposition to one another with a space therebetween for receiving the first portion and the second portion in contact with one another, wherein the structure is non-conductive of electricity; and
- an electrical circuit comprising a power source and a switch arranged such that closure of the switch applies a voltage potential across the first electrode and the second electrode, such that when the first and second portions are positioned in the body of an animal and placed between the first and second electrodes in contact with one another and the switch is thereafter closed, heat is generated by electric resistance at the point of contact so as to melt regions of the first and second portions, and when the switch is thereafter opened, the melted portions of the first and second portions re-solidify so that a weld is formed at the point of contact.

In one form of the present invention, there is provided a method for forming a weld between two portions of a biocompatible conductive thermoplastic material in the body of an animal, wherein the method comprises:

- positioning first and second portions of a biocompatible conductive thermoplastic material in the body of an animal between first and second electrodes so that the first portion is in contact with the first electrode, the second portion is in contact with the second electrode, and the first and second portions of the biocompatible conductive thermoplastic material are in contact with one another;
- applying a selected amount of electrical current across the first and second electrodes so as generate a selected amount of heat by electric resistance at the point of contact between the first and second portions so as to cause a specific desired amount of melting of the first and second portions; and
- terminating the electrical current across the first and second electrodes so that the melted regions of the first and second portions re-solidify so that a weld is formed at the point of contact.

In one form of the present invention, there is provided a novel method and apparatus for suturing tissue.

In one form of the present invention, there is provided an end effector for a suturing device, the end effector comprising:

- a first arm having a tissue-engaging surface;
- a second arm having a tissue-engaging surface;
- at least one of the first and second arms being configured for movement (i) toward the other of the first and second arms so as to clamp tissue between the tissue-engaging surface of the first arm and the tissue-engaging surface of the second arm, and (ii) away from the other of the first and second arms so as to release tissue clamped between the tissue-engaging surface of the first arm and the tissue-engaging surface of the second arm;
- the second arm having an opening therein; and
- a needle having a penetrating tip, the needle being configured for movement (i) toward the tissue-engaging surface of the first arm so as to position the penetrating tip of the needle adjacent to the tissue-engaging surface of the first arm, whereby to penetrate tissue clamped between the tissue-engaging surface of the first arm and the tissue-engaging surface of the second arm, and (ii) away from the tissue-engaging surface of the first arm so as to withdraw from tissue clamped between the tissue-engaging surface of the first arm and the tissue-engaging surface of the second arm;
- the needle being configured to pass through the opening in the second arm as the needle moves toward the tissue-engaging surface of the first arm and to pass through the opening in the second arm as the needle moves away from the tissue-engaging surface of the first arm.

In one form of the present invention, there is provided a novel method and apparatus for ligating tissue.

In one form of the present invention, there is provided apparatus for applying suture to tissue, wherein the suture comprises a biocompatible, electrically conductive thermoplastic material having a diameter, the apparatus comprising:

- a shaft;
- a jaw assembly comprising a first jaw member comprising a first tip and a first passageway for slidably receiving the suture, and a second jaw member comprising a second tip and a second passageway for slidably receiving the suture, wherein at least one of the first and second jaw members is pivotally mounted so as to be movable between (i) at least one open position in which the first and second tips of the first and second jaw members are separated from one another by a gap, and (ii) a closed position in which the first and second passageways form a continuous pathway;
- a gripping assembly comprising a first gripper comprising a first gripping surface, and a second gripper comprising a second gripping surface, wherein at least one of the first and second grippers is movably mounted to the shaft so as to be movable between (i) a release position in which the first and second gripping surfaces of the first and second grippers are separated from one another by a gap which is larger than the diameter of a suture which is to be used to form a loop of the suture, and (ii) a gripping position in which the first and second gripping surfaces of the first and second grippers are separated from one another by a distance which is less than the diameter of a suture which is used to form the loop of the suture;

an electrode assembly comprising an electrode for selectively applying an electric potential to suture clamped between the first and second gripping surfaces of the first and second grippers, wherein the electrode is movably mounted to the shaft so as to be movable between (i) a non-weld position in which the electrode is spaced from suture clamped between the first and second gripping surfaces of the first and second grippers, and (ii) a welding position in which the electrode engages suture clamped between the first and second gripping surfaces of the first and second grippers; and an operating mechanism for selectively operating the gripping assembly and the electrode assembly in response to movement of at least one of the first and second jaw members of the jaw assembly, wherein, when the electrode assembly is in its non-weld position, and the gripping assembly is in its release position, and the jaw assembly is in its closed position, and when suture is positioned between the first and second gripping surfaces of the gripping assembly, progressive movement of the at least one of the first and second jaw members of the jaw assembly towards its at least one open position causes, sequentially:

(a) at least one of the first and second grippers to move from its release position to its gripping position;

(b) the electrode to move from its non-weld position to its welding position; and (c) at least one of the first and second grippers to move from its gripping position to its release position.

In one form of the present invention, there is provided a medical device for applying a suture to tissue, comprising:

a jaw assembly, a gripping assembly, an electrode assembly, and an operating mechanism operably coupled to the jaw assembly, to the gripping assembly, and to the electrode assembly;

the jaw assembly comprising a first jaw member and a second jaw member, the first jaw member comprising a first tip and a first passageway for the suture, the second jaw member comprising a second tip and a second passageway for the suture, at least one of the first and second jaw members being movable between an open position and a closed position, the open position being a position in which the first and second tips of the first and second jaw members are separated by a gap, and the closed position being a position in which the first and second passageways of the first and second jaw members form a continuous passageway for the suture;

the gripping assembly comprising a first gripper and a second gripper, the first gripper comprising a first gripping surface, the second gripper comprising a second gripping surface, at least one of the first and second grippers being movable between a release position and a gripping position, the release position being a position in which the first and second gripping surfaces of the first and second grippers are separated from one another by a gap larger than a diameter of the suture, and the gripping position being a position in which the first and second gripping surfaces of the first and second grippers are separated from one another by a distance smaller than the diameter of the suture;

the electrode assembly comprising an electrode configured to apply an electric potential to the suture clamped between the first and second gripping surfaces of the first and second grippers, the electrode being movable between a welding position and a non-weld position, the welding position being a position in which the electrode engages the suture between the first and second gripping surfaces of the first and second grippers, and the non-weld position being a position in which the electrode is spaced from the suture between the first and second gripping surfaces of the first and second grippers; and the operating mechanism operating the gripping assembly and the electrode assembly such that on the conditions the electrode assembly is in the non-weld position, the gripping assembly is in the release position, the jaw assembly is in the closed position, and the suture is positioned between the first and second gripping surfaces of the gripping assembly, progressive movement of at least one of the first and second jaw members towards the open position causes, sequentially, at least one of the first and second grippers to move from the release position to the gripping position, then the electrode to move from the non-weld position to the welding position, and then at least one of the first and second grippers to move from the gripping position to the release position.

In one form of the present invention, there is provided a method for applying suture to tissue, wherein the suture comprises a biocompatible, electrically conductive thermoplastic material having a diameter, the method comprising:

providing apparatus comprising:

a shaft;

a jaw assembly comprising a first jaw member comprising a first tip and a first passageway for slidably receiving the suture, and a second jaw member comprising a second tip and a second passageway for slidably receiving the suture, wherein at least one of the first and second jaw members is pivotally mounted so as to be movable between (i) at least one open position in which the first and second tips of the first and second jaw members are separated from one another by a gap, and (ii) a closed position in which the first and second passageways form a continuous pathway;

a gripping assembly comprising a first gripper comprising a first gripping surface, and a second gripper comprising a second gripping surface, wherein at least one of the first and second grippers is movably mounted to the shaft so as to be movable between (i) a release position in which the first and second gripping surfaces of the first and second grippers are separated from one another by a gap which is larger than the diameter of a suture which is to be used to form a loop of the suture, and (ii) a gripping position in which the first and second gripping surfaces of the first and second grippers are separated from one another by a distance which is less than the diameter of a suture which is used to form the loop of the suture;

an electrode assembly comprising an electrode for selectively applying an electric potential to suture clamped between the first and second gripping surfaces of the first and second grippers, wherein the electrode is movably mounted to the shaft so as to be movable between (i) a non-weld position in which the electrode is spaced from suture clamped between the first and second gripping surfaces of the first and second grippers, and (ii) a welding position in which the electrode engages suture clamped between the first and second gripping surfaces of the first and second grippers; and an operating mechanism for selectively operating the gripping assembly and the electrode assembly in response to movement of at least one of the first and second jaw members of the jaw assembly, wherein, when the electrode assembly is in its non-weld position, and the gripping assembly is in its release position, and the jaw assembly is in its closed position, and when suture is positioned between the first and second gripping surfaces of the gripping assembly, progressive movement of the at least one of the first and second jaw members of the jaw assembly towards its at least one open position causes, sequentially:

(a) at least one of the first and second grippers to move from its release position to its gripping position;

(b) the electrode to move from its non-weld position to its welding position; and (c) at least one of the first and second grippers to move from its gripping position to its release position;

positioning the apparatus adjacent to the tissue while (i) the jaw assembly is in its at least one open position, (ii) the gripping assembly is in its release position and (iii) the electrode assembly is in its non-weld position;

moving at least one of the first and second jaw members so that the jaw assembly is in its closed position;

advancing the suture through the continuous pathway so that the suture forms a loop of suture; and progressively moving the at least one of the first and second jaw members of the jaw assembly towards its at least one open position causing, sequentially:

(a) at least one of the first and second grippers to move from its release position to its gripping position;

(b) the electrode to move from its non-weld position to its welding position; and (c) at least one of the first and second grippers to move from its gripping position to its release position.

In one form of the present invention, there is provided a suture advancement/retraction mechanism for advancing/retracting suture, the suture advancement/retraction mechanism comprising:

a first tubular element comprising a side wall having a distal end, a proximal end, and a lumen extending therebetween, a shoulder formed on the outside of the side wall, and a flange extending radially outwardly from the side wall, the flange being spaced from the shoulder, and a portion of the side wall adjacent to the shoulder being compressible;

a second tubular element comprising a side wall having a distal end, a proximal end, and a lumen extending therebetween, a shoulder formed on the inside of the side wall, and a flange extending radially outwardly from the side wall, the second tubular element being mounted concentrically on the first tubular element so that the shoulder formed on the inside of the side wall of the second tubular element is engageable with the shoulder formed on the outside of the side wall of the first tubular element;

a spring mounted concentrically over the side wall of the first tubular element so as to engage the flange of the first tubular element and the flange of the second tubular element, whereby to bias the first tubular element proximally and the second tubular element distally, whereby to bias the shoulder of the first tubular element and the shoulder of the second tubular element into engagement with one another; and a stop engageable with the first tubular element so as to selectively stop proximal movement of the first tubular element, such that:

(i) when the first tubular element is in engagement with the stop and the flange of the second tubular element is forced toward the flange of the first tubular element so as to compress the spring, a suture may be advanced through the lumen of the first tubular element;

(ii) when the flange of the second tubular element is thereafter forced away from the flange of the first tubular element, the shoulder of the second tubular element engages the shoulder of the first tubular element so as to compress the side wall of the first tubular element and grip the suture advanced through the lumen of the first tubular element, whereby to drive the suture distally;

(iii) when the flange of the second tubular element is thereafter moved toward the flange of the first tubular element, the shoulder of the second tubular element remains engaged with the shoulder of the first tubular element so as to continue to compress the side wall of the first tubular element and grip the suture advanced through the lumen of the first tubular element, whereby to drive the suture proximally; and (iv) when the first tubular element is thereafter moved into engagement with the stop and the flange of the second tubular element is moved toward the flange of the first tubular element, the shoulder of the second tubular element disengages from the shoulder of the first tubular element so as to stop compressing the side wall of the first tubular element and release the suture extending through the lumen of the first tubular element.

In one form of the present invention, there is provided a medical device for advancing and retracting a suture, the medical device comprising:

a first tubular element, a second tubular element, a spring, and a stop;

the first tubular element comprising a first side wall, a first shoulder formed on an outside of the first side wall, and a first flange spaced from the first shoulder and extending radially outward from the first side wall, the first side wall comprising a distal end, a proximal end, a lumen extending between the proximal and distal ends of the first side wall, and a compressible portion adjacent the first shoulder;

the second tubular element comprising a second side wall, a second shoulder formed on an inside of the second side wall, and a second flange extending radially outwardly from the second side wall, the second tubular element being mounted concentrically on the first tubular element so that the second shoulder of the second tubular member is engageable with the first shoulder of the first tubular element, and the second side wall comprising a distal end, a proximal end, and a lumen extending between the proximal and distal ends of the second sidewall;

the spring being mounted concentrically over the side wall of the first tubular element so as to engage the flange of the first tubular element and the flange of the second tubular element, the spring being positioned to bias the first tubular element proximally and the second tubular element distally, and the spring being positioned to bias the first shoulder and the second shoulder into engagement with one another; and the stop being selectively engageable with the first tubular element so as to stop proximal movement of the first tubular element, such that:

(i) on the conditions the first tubular element is engaged with the stop, and the second flange is forced toward the flange, the suture is unconstrained to be advanced through the lumen of the first tubular element; and thereafter, (ii) to drive the suture distally on the condition the second flange of the second tubular element is forced away from the first flange, the second shoulder engages the first shoulder and compresses the compressible portion of the first side wall to grip the suture advanced through the lumen of the first tubular element; and thereafter, (iii) to drive the suture proximally on the condition the second flange is moved toward the first flange, the second shoulder remains engaged with the first shoulder so as to continue to compress the compressible portion of the first side wall to grip the suture advanced through the lumen of the first tubular element; and thereafter, (iv) to release the suture extending through the lumen of the first tubular element on the conditions the first tubular element is moved into engagement with the stop, and the second flange is moved toward the first flange, the second shoulder disengages from the first shoulder so as to stop compressing the compressible portion of the first side wall.

In one form of the present invention, there is provided a method for advancing/retracting suture, the method comprising:

providing a suture advancement/retraction mechanism for advancing/retracting suture, the suture advancement/retraction mechanism comprising:

a first tubular element comprising a side wall having a distal end, a proximal end, and a lumen extending therebetween, a shoulder formed on the outside of the side wall, and a flange extending radially outwardly from the side wall, the flange being spaced from the shoulder, and a portion of the side wall adjacent to the shoulder being compressible;

a second tubular element comprising a side wall having a distal end, a proximal end, and a lumen extending therebetween, a shoulder formed on the inside of the side wall, and a flange extending radially outwardly from the side wall, the second tubular element being mounted concentrically on the first tubular element so that the shoulder formed on the inside of the side wall of the second tubular element is engageable with the shoulder formed on the outside of the side wall of the first tubular element;

a spring mounted concentrically over the side wall of the first tubular element so as to engage the flange of the first tubular element and the flange of the second tubular element, whereby to bias the first tubular element proximally and the second tubular element distally, whereby to bias the shoulder of the first tubular element and the shoulder of the second tubular element into engagement with one another; and a stop engageable with the first tubular element so as to selectively stop proximal movement of the first tubular element, such that:

(i) when the first tubular element is in engagement with the stop and the flange of the second tubular element is forced toward the flange of the first tubular element so as to compress the spring, a suture may be advanced through the lumen of the first tubular element;

(ii) when the flange of the second tubular element is thereafter forced away from the flange of the first tubular element, the shoulder of the second tubular element engages the shoulder of the first tubular element so as to compress the side wall of the first tubular element and grip the suture advanced through the lumen of the first tubular element, whereby to drive the suture distally;

(iii) when the flange of the second tubular element is thereafter moved toward the flange of the first tubular element, the shoulder of the second tubular element remains engaged with the shoulder of the first tubular element so as to continue to compress the side wall of the first tubular element and grip the suture advanced through the lumen of the first tubular element, whereby to drive the suture proximally; and (iv) when the first tubular element is thereafter moved into engagement with the stop and the flange of the second tubular element is moved toward the flange of the first tubular element, the shoulder of the second tubular element disengages from the shoulder of the first tubular element so as to stop compressing the side wall of the first tubular element and release the suture extending through the lumen of the first tubular element;

moving the first tubular element into engagement with the stop, and forcing the second flange towards the flange so as to compress the spring;

advancing a suture through the lumen of the first tubular element;

forcing the flange of the second tubular element away from the flange of the first tubular element so as to cause the shoulder of the second tubular element to engage the shoulder of the first tubular element so as to compress the side wall of the first tubular element and grip the suture advanced through the lumen of the first tubular element, whereby to drive the suture distally;

moving the flange of the second tubular element towards the flange of the first tubular element, while the shoulder of the second tubular element remains engaged with the shoulder of the first tubular element so as to continue to compress the side wall of the first tubular element and grip the suture advanced through the lumen of the first tubular element, whereby to drive the suture proximally; and moving the first tubular element into engagement with the stop and moving the flange of the second tubular element toward the flange of the first tubular element so that the shoulder of the second tubular element disengages from the shoulder of the first tubular element so as to stop compressing the side wall of the first tubular element and release the suture extending through the lumen of the first tubular element.

In one form of the present invention, there is provided an apparatus for applying suture to tissue, wherein the suture comprises a biocompatible, electrically conductive thermoplastic material and having a diameter, the apparatus comprising:

a shaft having a distal end and a proximal end;

a jaw assembly comprising a first jaw member comprising a first tip, a first passageway for slidably receiving suture and a first slot, and a second jaw member comprising a second tip, a second passageway for slidably receiving suture and a second slot, wherein at least one of the first and second jaw members is pivotally mounted to the shaft so as to be movable between (i) at least one open position in which the first and second tips of the first and second jaw members are separated from one another by a gap, and (ii) a closed position in which the first and second tips of the first and second jaw members engage one another so that the first and second passageways form a continuous pathway;

a gripping assembly comprising a first gripper comprising a first gripping surface, a second gripper comprising a second gripping surface, and a gripper clip for engaging the first gripper and the second gripper so as to move at least one of the first and second grippers between (i) a release position in which the first and second gripping surfaces of the first and second grippers are separated from one another by a gap which is larger than the diameter of a suture which is to be used to form a loop of suture, and (ii) a gripping position in which the first and second gripping surfaces of the first and second grippers are separated from one another by a distance which is less than the diameter of a suture which is used to form the loop of suture;

an electrode assembly comprising an electrode for selectively applying an electric potential to suture clamped between the first and second gripping surfaces of the first and second grippers, wherein the electrode is movable between (i) a non-weld position in which the electrode is spaced from suture clamped between the first and second gripping surfaces of the first and second grippers, and (ii) a welding position in which the electrode engages suture clamped between the first and second gripping surfaces of the first and second grippers;

an actuator rod assembly for selectively operating the jaw assembly, the gripping assembly and the electrode assembly in response to movement of the actuator rod assembly in a distal direction, the actuator rod assembly comprising an actuator rod movably mounted to the shaft, a drive pin mounted to the actuator rod and extending through the first slot of the first jaw member and the second slot of the second jaw member, the gripper clip of the gripping assembly being mounted to the actuator rod, and the electrode of the electrode assembly being spring-biased away from the actuator rod and into engagement with the first and second grippers of the gripper assembly when the gripper assembly is in its gripping position, wherein, when the electrode assembly is in its non-weld position, the gripping assembly is in its release position, and the jaw assembly is in its open position, and suture is positioned between the first and second grippers of the gripping assembly, progressive movement of the actuator rod in a distal direction causes, sequentially:

(a) at least one of the first and second jaws of the jaw assembly to move from its open position into its closed position;

(b) at least one of the first and second grippers to move from its release position to its gripping position; and (c) the electrode to move from its non-weld position to its welding position; and subsequent progressive movement of the actuator rod in a proximal direction causes, sequentially:

(d) the electrode to move from its weld position to its non-welding position;

(e) at least one of the first and second grippers to move from its gripping position to its release position; and (f) at least one of the first and second jaws of the jaw assembly to move from its closed position into its open position.

In one form of the present invention, there is provided a medical device comprising:

a jaw assembly, a gripping assembly, an electrode assembly, and an actuator rod assembly operably coupled to the jaw assembly, the gripping assembly, and the electrode assembly;

the jaw assembly comprising a first jaw member and a second jaw member, the first jaw member comprising a first tip, a first slot, and a first passageway for receiving a suture, the second jaw member comprising a second tip, a second slot, and a second passageway for receiving the suture, at least one of the first and second jaw members being movable between an open position and a closed position, the open position being a position in which the first and second tips of the first and second jaw members are separated from one another by a gap, and the closed position being a position in which the first and second passageways form a continuous passageway for the suture;

the actuator rod assembly comprising a movable actuator rod and a drive pin mounted to the actuator rod, the drive pin extending through the first slot of the first jaw member and the second slot of the second jaw member;

the gripping assembly comprising a first gripper, a second gripper, and a gripper clip, the first gripper comprising a first gripping surface, the second gripper comprising a second gripping surface, the gripper clip being mounted to the actuator rod and engaging the first gripper and the second gripper so as to move at least one of the first and second grippers between a release position and a gripping position, the release position being a position in which the first and second gripping surfaces of the first and second grippers are separated from one another by a gap larger than a diameter of the suture, and the gripping position being a position in which the first and second gripping surfaces of the first and second grippers are separated from one another by a distance smaller than the diameter of the suture; and the electrode assembly comprising an electrode configured to apply an electric potential to the suture between the first and second gripping surfaces of the first and second grippers, the electrode being movable between a non-weld position and a welding position, the non-weld position being a position in which the electrode is spaced from the suture between the first and second gripping surfaces of the first and second grippers, and the welding position being a position in which the electrode engages the suture between the first and second gripping surfaces of the first and second grippers;

wherein on the condition the gripper assembly is in the gripping position, the electrode of the electrode assembly is spring-biased away from the actuator rod and into engagement with the first and second grippers of the gripper assembly; and wherein on the conditions the electrode assembly is in the non-weld position, the gripping assembly is in the release position, the jaw assembly is in the open position, and suture is positioned between the first and second grippers of the gripping assembly, then a first progressive movement of the actuator rod in a distal direction causes, sequentially:

(a) at least one of the first and second jaws of the jaw assembly to move from the open position to the closed position, (b) at least one of the first and second grippers to move from the release position to the gripping position, and (c) the electrode to move from the non-weld position to the welding position, and a subsequent second progressive movement of the actuator rod in a proximal direction causes, sequentially:

(d) the electrode to move from the weld position to the non-welding position, (e) at least one of the first and second grippers to move from the gripping position to the release position, and (f) at least one of the first and second jaws of the jaw assembly to move from the closed position into the open position.

In one form of the present invention, there is provided a method for applying suture to tissue, the method comprising:

providing apparatus for applying suture to tissue, wherein the suture comprises a biocompatible, electrically conductive thermoplastic material and having a diameter, the apparatus comprising:

a shaft having a distal end and a proximal end;

a jaw assembly comprising a first jaw member comprising a first tip, a first passageway for slidably receiving suture and a first slot, and a second jaw member comprising a second tip, a second passageway for slidably receiving suture and a second slot, wherein at least one of the first and second jaw members is pivotally mounted to the shaft so as to be movable between (i) at least one open position in which the first and second tips of the first and second jaw members are separated from one another by a gap, and (ii) a closed position in which the first and second tips of the first and second jaw members engage one another so that the first and second passageways form a continuous pathway;

a gripping assembly comprising a first gripper comprising a first gripping surface, a second gripper comprising a second gripping surface, and a gripper clip for engaging the first gripper and the second gripper so as to move at least one of the first and second grippers between (i) a release position in which the first and second gripping surfaces of the first and second grippers are separated from one another by a gap which is larger than the diameter of a suture which is to be used to form a loop of suture, and (ii) a gripping position in which the first and second gripping surfaces of the first and second grippers are separated from one another by a distance which is less than the diameter of a suture which is used to form the loop of suture;

an electrode assembly comprising an electrode for selectively applying an electric potential to suture clamped between the first and second gripping surfaces of the first and second grippers, wherein the electrode is movable between (i) a non-weld position in which the electrode is spaced from suture clamped between the first and second gripping surfaces of the first and second grippers, and (ii) a welding position in which the electrode engages suture clamped between the first and second gripping surfaces of the first and second grippers;

an actuator rod assembly for selectively operating the jaw assembly, the gripping assembly and the electrode assembly in response to movement of the actuator rod assembly in a distal direction, the actuator rod assembly comprising an actuator rod movably mounted to the shaft, a drive pin mounted to the actuator rod and extending through the first slot of the first jaw member and the second slot of the second jaw member, the gripper clip of the gripping assembly being mounted to the actuator rod, and the electrode of the electrode assembly being spring-biased away from the actuator rod and into engagement with the first and second grippers of the gripper assembly when the gripper assembly is in its gripping position, wherein, when the electrode assembly is in its non-weld position, the gripping assembly is in its release position, and the jaw assembly is in its open position, and suture is positioned between the first and second grippers of the gripping assembly, progressive movement of the actuator rod in a distal direction causes, sequentially:

(a) at least one of the first and second jaws of the jaw assembly to move from its open position into its closed position;

(b) at least one of the first and second grippers to move from its release position to its gripping position; and (c) the electrode to move from its non-weld position to its welding position; and subsequent progressive movement of the actuator rod in a proximal direction causes, sequentially:

(d) the electrode to move from its weld position to its non-welding position;

(e) at least one of the first and second grippers to move from its gripping position to its release position; and (f) at least one of the first and second jaws of the jaw assembly to move from its closed position into its open position;

positioning the apparatus adjacent to the tissue while the jaw assembly is in its at least one open position, the gripping assembly is in its release position, and the electrode assembly is in its non-weld position;

progressively moving the actuator rod in a distal direction so as to cause, sequentially:

(a) at least one of the first and second jaws of the jaw assembly to move from its open position into its closed position;

(b) at least one of the first and second grippers to move from its release position to its gripping position; and (c) the electrode to move from its non-weld position to its welding position; and subsequently progressively moving the actuator rod in a proximal direction so as to cause, sequentially:

(d) the electrode to move from its weld position to its non-welding position;

(e) at least one of the first and second grippers to move from its gripping position to its release position; and (f) at least one of the first and second jaws of the jaw assembly to move from its closed position into its open position.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 7H is a schematic view showing the distal end effector of FIG. 7G, with a knife blade advanced to cut the suture;

FIG. 7I is a schematic view showing the distal end effector of FIG. 7H, with the grasper in a re-opened position;

FIGS. 12*a* and 12*b* are detail isometric schematic views of sub-components of the device shown in FIG. 11;

DETAILED DESCRIPTION OF THE PREFERRED EMBODIMENTS

Figure 1:
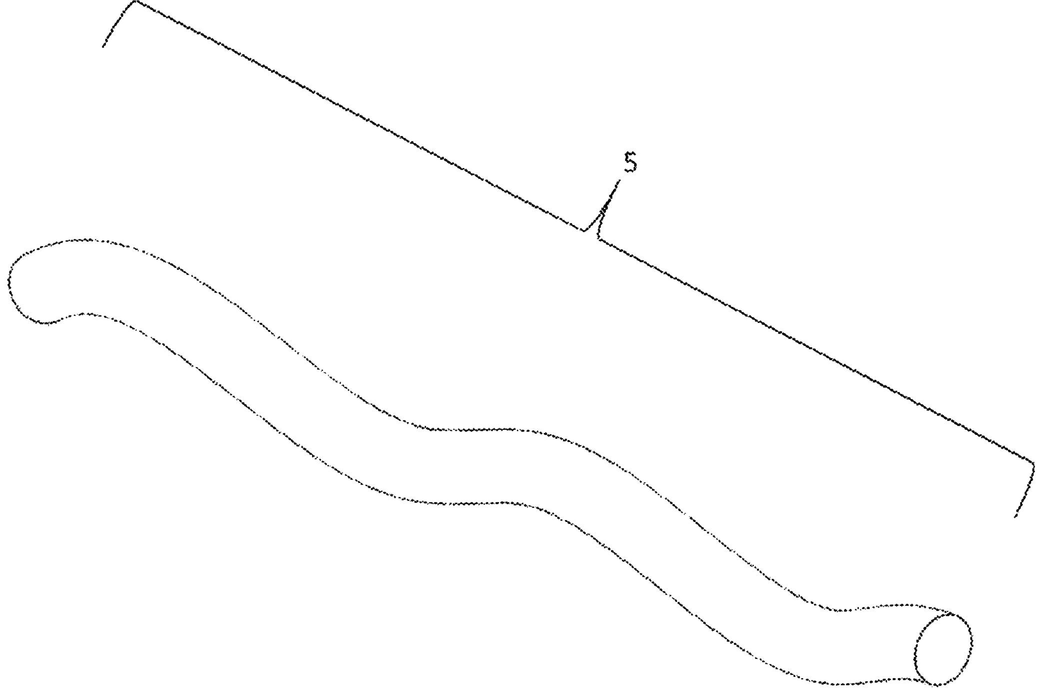
FIG. 1 is a schematic view showing a short length of filamentous material formed in accordance with the present invention (the filamentous material is sometimes referred to herein as "conductive thermoplastic suture")

The present invention comprises the provision and use of a new and improved method and apparatus for producing suture welds of sufficient strength and reliability to replace, or enhance the strength of, suture knots or other loop closure devices.

This disclosure describes inventive concepts with reference to specific examples. However, the intent is to cover all modifications, equivalents, and alternatives of the inventive concepts that are consistent with this disclosure.

For the purposes of the present patent application, the term "suture" is intended to mean a filament used in surgery to join tissue and/or objects (e.g., with a suturing stitch), or to ligate vessels, tissue or objects (e.g., with a ligating stitch).

For the purposes of the present invention, the term "stitch" is intended to mean a length of suture where portions of the length of suture are joined together to form a continuous loop, with that loop passing through or around tissue and/or objects to provide a surgical purpose, such as closing a wound (e.g., with a suturing stitch), occluding a vessel (e.g., with a ligating stitch), etc.

For the purposes of the present invention, the term "suture loop" is intended to mean a length of suture which is formed into a continuous structure with overlapping portions, before and/or after joining of those overlapping portions, e.g., by welding.

The Invention in General

Forming surgical stitches in anatomic regions with difficult surgical access is a challenge in minimally invasive surgery. This disclosure describes an invention that joins sutures by welding (instead of, for example, tying or knotting). This saves time and can be done in extremely confined spaces. Unlike existing suture welding systems, the present invention can deliver suture welds through a serpentine path, such as through a curved catheter, using low-cost welding apparatus. Aspects of the disclosed invention can be particularly beneficial to manufacturers of robotic surgical systems. For example, a fully automated suturing device accessory can be utilized in surgical robotic systems.

Conventional "needle-and-thread" suturing requires manual or instrument access and is time-consuming, requires maneuvering room and leaves bulky knots at the surgical site. Crimp-type joinder devices leave behind a foreign body (e.g., a metal crimp) at the joinder site, and the high crimping force required to actuate the crimp necessitates substantial shaft diameter and limited shaft length.

Existing suture welding devices utilizing the direct application of heat risk undesirable heating of surrounding tissues and/or suture weakening. Existing ultrasonic suture welding devices are bulky and expensive and require straight line access to the surgical site. Existing surgical robotic manipulators are time-consuming, require maneuvering room, and have a steep learning curve.

Traditionally, formed sutures are passed through tissue with a needle and tied with a knot into a loop to close wounds and allow the healing of tissue. Minimally invasive surgery (MIS) and robotic surgery place demands on the surgeon's skill due to the need to tie suture knots in regions of the body which are inaccessible to the surgeon's hands. Many surgical instruments have been developed that assist the surgeon in knot tying or provide a knot substitute. Such instruments have been invented by the present inventor and others. One known instrument comprises a tool for the formation of welded loops of suture, and another considers the welded loop of suture itself as a surgical fastener. While this method of joining suture into stitches facilitates suturing in difficult to access regions of the body, in practice it requires an ultrasonic generator, transducer and wave guide to complete welds in monofilament suture. This apparatus is bulky and expensive, and requires straight-line access to the surgical site from the point of incision.

The present invention seeks to improve upon these earlier inventions through the use of a novel suture material and novel welding apparatus that does not require bulky, costly ultrasonic equipment and can be delivered through a slender and/or curved shaft.

Novel aspects of the disclosed invention include, among other things:

1. a suture material that is directly weldable using a small amount of simple low voltage electrical energy;
2. a tissue fastening device or construct comprising a continuous welded loop of filamentous material consisting of an electrically weldable polymer;
3. an apparatus for welding electrically weldable suture that offers precise control over weld parameters so as to ensure a consistent, high strength weld;
4. an apparatus for welding electrically weldable suture that can safely operate inside the body without damaging adjacent tissue; and
5. an apparatus for welding electrically weldable suture that can be delivered through a serpentine path to remote regions of a body.

These, and other, benefits can be achieved by the new material, apparatus, method and devices of the present invention.

The suture material aspect of the present invention is made of a filament of biocompatible material, of a diameter, strength and flexibility consistent with surgical suture, and electrically conductive with a predictable resistance value.

The apparatus aspect of the present invention includes a mechanism for holding the overlapping portion of a suture loop; a mechanism for applying contact pressure through the overlapping region; and a mechanism for applying and controlling electrical current through the overlapping region to cause localized heating of the overlapping region by the electrical current passing through the overlapping region and thereby causing localized melting of the overlapping region, which then re-solidifies so as to form a weld.

Some versions of the apparatus further include a mechanism for clamping the suture to maintain suture tension during the welding process; a mechanism for trimming suture tails extending past the suture loop; a handle with controls for allowing a user (e.g., a surgeon) to maneuver the apparatus and initiate the welding process; and an elongated straight, curved, articulating, flexible and/or steerable shaft connecting the distal welding apparatus to the proximal handle, allowing the user to maneuver the welding apparatus into regions of the body with difficult access (such as in MIS procedures).

Further versions of the apparatus include means for controllably or automatically penetrating tissue, passing suture, tensioning suture, trimming suture tails and releasing the formed tissue-fastening suture loop. Examples of these means are disclosed in prior U.S. Pat. No. 5,417,700 (which patent is hereby incorporated herein by reference) by the present inventor and may be used individually or in combination with this new welding apparatus.

The welding process aspect of the present invention shares many characteristics in common with resistance or spot welding of metals, with several important novel distinctions, including but not limited to: low voltage and special electrical isolation necessary for medical devices; the ability to work with non-metallic conductive materials; and means for controlling the localization and depth of material melt so as to preserve the high strength of the highly linearized molecular chains of the conductive polymer or the composite materials being welded.

The suture loop formed by the material, apparatus and process disclosed herein is a tissue-fastening device or construct in the form of a continuous loop formed in situ. The loop comprises a filament of the biocompatible, conductive material disclosed herein, arcing approximately in the configuration of a circle, with an overlapping region joined by a weld.

Also disclosed herein are other structures made of the disclosed material, and welded in situ, but not necessarily taking the form of a loop or comprising filamentous material of a uniform cross-section.

In one form of the present invention, the welded suture loops are used to secure together two or more portions of tissue.

In another form of the present invention, the welded suture loops are used to ligate tissue.

The Material Used to Form the Weldable Suture and/or the Weldable Structures

FIG. 1 shows a short length of filamentous biocompatible material 5. In one version of the present invention, material 5 has the characteristics of being substantially round in cross-section, and falling within the ranges dictated by United States Pharmacopeia for suture diameters (USP29-861) and tensile strengths (USP29-881) and equivalent international standards. Material 5 further has the characteristics of being electrically conductive with a known resistance, and meltable with a melting temperature above 37° C. (so that material 5 is in solid form in a human body). Thus, material 5 comprises an electrically conductive thermoplastic material.

In a preferred form of the invention, material 5 is a monofilament of a thermoplastic polymer compounded with a conductive additive. In some versions, a dispersant is used to assure uniform mixing of the conductive additive within the polymer matrix. In some versions, the base thermoplastic polymer and conductive additive (and dispersant, if required) are melt-compounded (mixed), extruded, and drawn to produce a monofilament with substantially linear molecular chains for superior strength and flexibility. In other versions, the melt-compounded (mixed) material is injection molded into single or multi-part devices for medical applications. In some versions, the thermoplastic polymer is a bio-absorbable material currently approved for use as a suture or implant material (e.g., Polylactic Acid (PLA), Polyglycolide (PGA), Polydioxanone (PDS), a thermoplastic linear polyester such as that sold under the tradename TephaFLEX™, etc.). In other versions, the thermoplastic polymer is a non-absorbable material (e.g., Nylon, Polypropylene, Polycarbonate, etc.). In some versions, the conductive additive is an inert and/or non-toxic material such as carbon black, carbon fiber, iron oxide ($Fe_{203}$ and others) or metallic powders, nanoparticles (such as carbon nanotubes or fullerenes, aka "Buckyballs") or metal coated glass microspheres. In other versions, the conductive additive is any one of intrinsically conducting polymers (ICPs) including, but not limited to, polyacetylene, polyaniline, polythiophene, and polyphenylenevinylene. In some versions, these non-thermoplastic polymers are compounded with thermoplastic base polymers. In other versions, the non-thermoplastic polymers are applied as a film coating to a base polymer filament or part. In some versions the conductive coating is a continuous or patterned coating of conductive ink. In some versions a conductive polymer or composite may be co-extruded on the outside of another not necessarily conductive polymer at its core. In a version the core material has a higher melting temperature than the co-extruded outside layer. In other versions, the filament may be a multi-strand structure such as braided suture made of bundles of microfilaments of conductive thermoplastic polymer, or a composite of different filaments braided together. In one version, conductive and non-conductive filaments are combined into a single braided suture. In another embodiment, microfilaments of varying melt temperatures and conductivity are braided together such that localized weld melting does not melt filaments of higher melting temperature, thereby preserving their highly linearized molecular orientation and high strength characteristics and producing a strong weld region. In one version, high strength, high-melt-temperature polymer filaments are provided in a low-melt temperature metallic matrix such that when applying electric current through adjacent portions of the polymer filament/metal matrix, the metal fuses but leaves the high strength filaments undamaged. In still another version, metallic suture or wire is used, however, pure metal is generally less desirable than conductive thermoplastic because high melt temperatures of metals and high thermal conductivity in metals risk damage to surrounding tissue, and melt spread in metals is more difficult to control than melt spread in polymers. In a version of the material, the material filament has transverse (side-to-side) conductivity but not axial (end-to-end) conductivity, which has the benefit of protecting the body from stray electrical current in the event of a break in the suture before or during welding. The transverse but not axial conductivity feature may result from drawing or stretching a composite material with a low conductive additive fill ratio, since the chain of additive may be broken axially during stretching but compacted transversely due to diameter reduction.

In one form of the invention, material 5 is a conductive thermoplastic polymer.

Apparatus for Welding Conductive Thermoplastic Suture

Figure 2A:
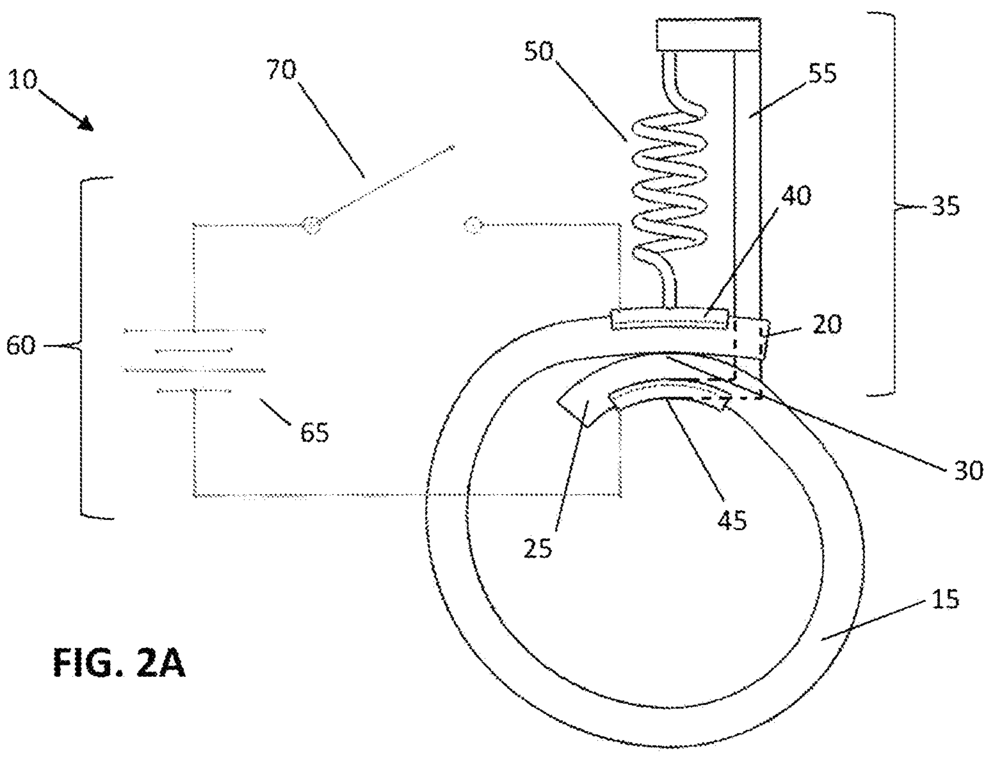
FIG. 2A is a schematic view showing novel apparatus for welding conductive thermoplastic suture.

FIG. 2A shows an apparatus 10 for welding a length of conductive thermoplastic suture 15. The length of conductive thermoplastic suture 15 comprises a first end 20 and a second end 25. First end 20 and second end 25 overlap at a contact point 30 so as to form a loop of suture 15. The loop of suture is held in its loop configuration by a clamping mechanism 35 applied at contact point 30. Clamping mechanism 35 comprises a first electrode 40 conforming to the surface of first end 20 of suture 15 and a second electrode 45 conforming to the surface of second end 25 of suture 15. A spring 50 applies a predetermined force between electrodes 40, 45 so as to maintain pressure on contact point 30. In one version, first electrode 40 and second electrode 45 are disposed substantially parallel to one another, resulting in line contact between first suture end 20 and second suture end 25 (not shown). In another version (i.e., the version shown in FIG. 2A), there is a relative curvature between first electrode and second electrode 45, resulting in a point contact between first suture end and second suture end 25. A structural frame 55 holds the components of the clamping mechanism (i.e., first electrode 40, second electrode 45 and spring 50) in place. Importantly, structural frame 55 is non-conductive between first electrode 40 and second electrode 45. An electrical circuit 60 comprising, at a minimum, a power source 65 and a switch 70, is connected to first electrode 40 and second electrode 45 as shown in FIG. 2A, such that closing switch 70 applies a voltage across first electrode 40 and second electrode 45 and allows current to flow through first suture end 20 and second suture end 25 at contact point 30. Preferably, power source 60 comprises a DC battery, but in other versions, power source 60 may comprise an exterior AC power source with an isolation transformer and a rectifier, or a low- or high-frequency AC power source.

In other versions of the present invention, additional features may be added to apparatus 10 in order to facilitate its use as a surgical instrument, such as tissue penetrating and suture passing means; tensioning means; clamping means to secure suture ends 20, 25 so as to facilitate welding with the suture under tension; suture tail-trimming means; weld region drying gas introduction means; an elongated and/or serpentine delivery shaft; and/or a handle for manual user interface or an electro-mechanical interface for connection to a surgical robot. These additional means and features are well known in the art and described in detail in prior patents (e.g., U.S. Pat. No. 5,417,700) by the present inventor and others.

Figure 2B:
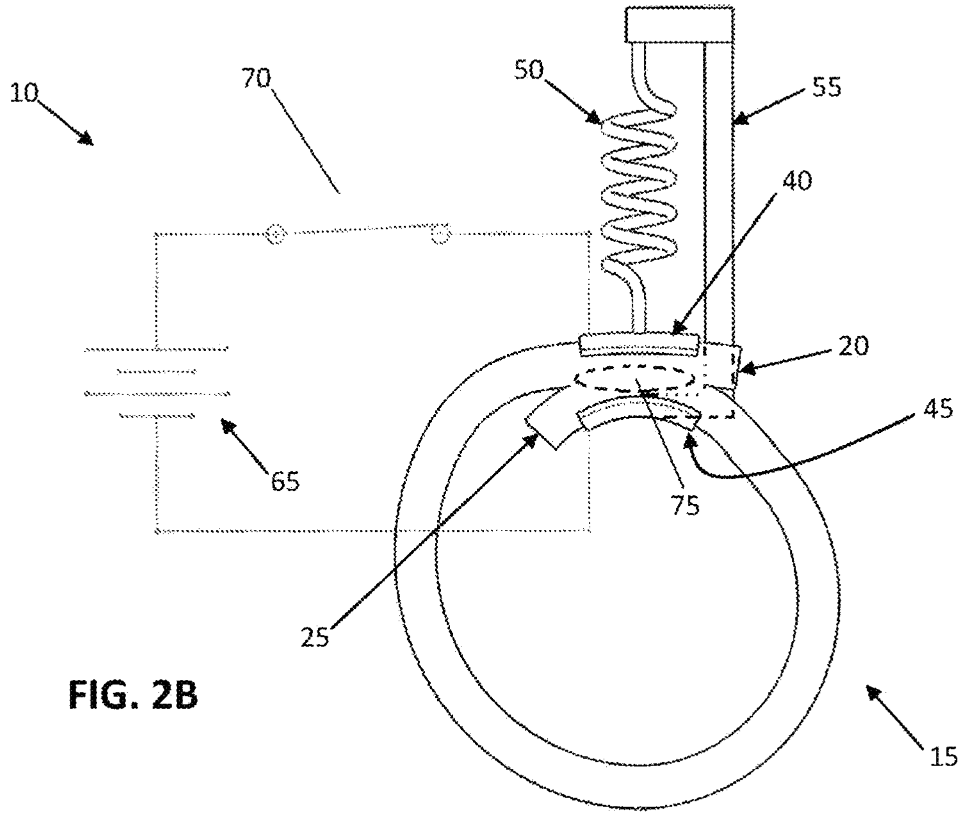
FIG. 2B is a schematic view showing the formation of a weld in conductive thermoplastic suture using the novel apparatus of FIG. 2A.

An illustrative method and process for forming a weld in conductive thermoplastic suture 15 is shown in FIG. 2B. Closing switch 70 causes current to flow from first electrode 40, through first suture end 20, across contact point 30, through second suture end 25 and then to second electrode 45. The highest resistance in this circuit is at contact point 30, resulting in heat build-up taking place in this region and spreading into first suture end 20 and second suture end 25. The heat build-up results in a localized melt region 75 that spreads into first suture end 20 and second suture end 25 as the heat increases. In one version, switch 70 is opened and the current stopped before the melt spreads across the full cross-section of the suture material. This differs from conventional resistance welding of metal where the full metal thickness is usually desired to be involved in the weld and is due to the non-isotropic nature of drawn, extruded monofilament suture.

In order to repeatedly and reliably achieve the optimum depth of melt penetration into suture ends 20, 25, a number of process control methods may be employed. In many of these process control methods, we will be referring to circuitry and components not shown in the simplified schematic shown in FIGS. 2A and 2B, such as a microprocessor and various sensors, however, they can be assumed to be deployed in the conventional manner familiar to those skilled in the art. In one such version, a simple timer is used to control the amount of time that the weld circuit is switched on. In another version, first and second electrodes 40, are configured such that as melting spreads, electrodes 40, 45 move toward each other as the melted material is displaced, and electrodes 40, 45 contact each other when the optimum amount of material has melted. The contacting electrodes short together, shunting current around the suture and stopping the heating. A current sensor may then be used to signal a microprocessor to interrupt the weld circuit. In another version, a displacement sensor may be substituted for the self-contacting electrodes to signal a microprocessor to shut off the circuit when the desired weld displacement has occurred. Other versions employ temperature sensors to control the weld circuit through a microprocessor, shutting off the weld circuit when a pre-set peak temperature or thermal distribution has been sensed. In still other versions, combinations of time, displacement and temperature sensors are employed and optimum weld parameters are determined by a microprocessor-based algorithm.

Note that the apparatus and method shown in FIGS. 2A and 2B are applicable to both tissue suturing procedures and tissue ligating procedures.

Tissue Fastening Device or Construct Formed by Welded Suture

Figure 3:
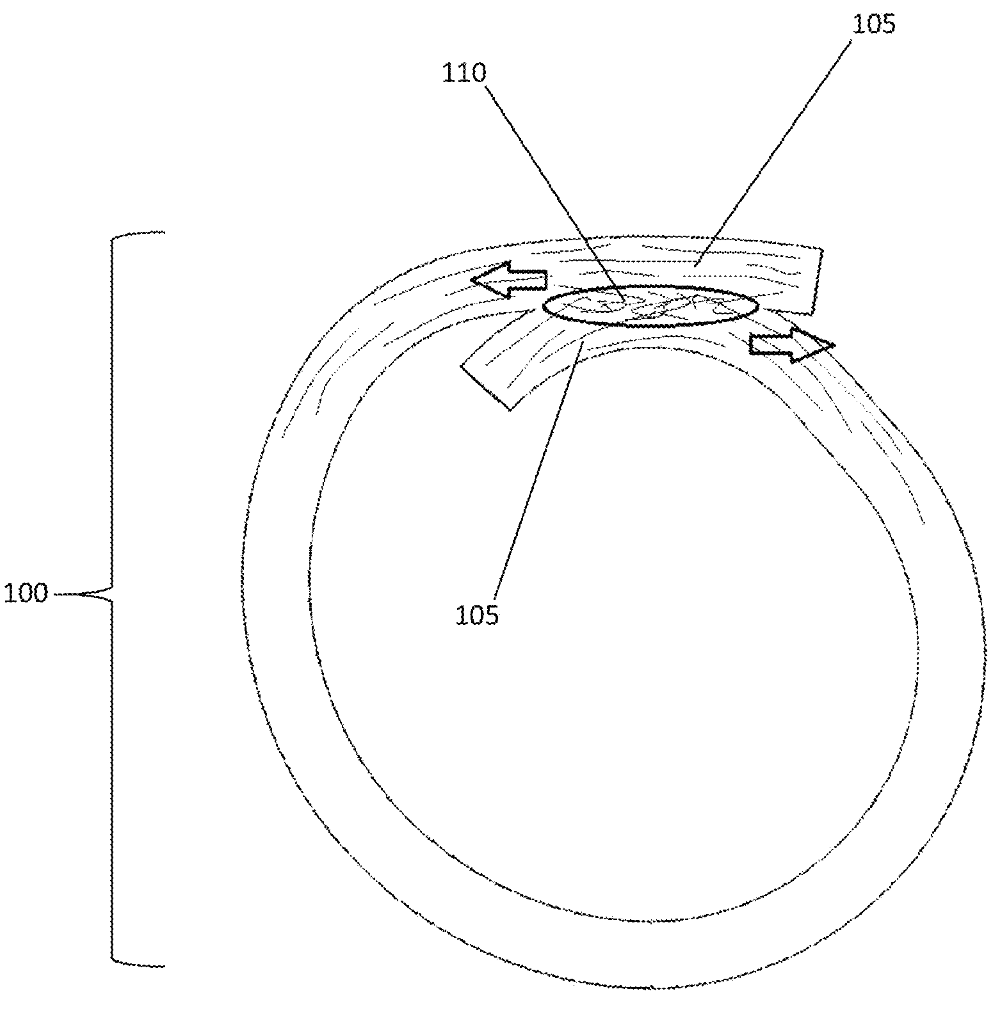
FIG. 3 is a schematic view showing a tissue fastening device or construct formed in accordance with the present invention.

FIG. 3 shows a tissue fastening device or construct 100 having a length of electrically conductive thermoplastic material formed into a continuous loop in situ, and joined by a partial depth penetration weld. In this figure, we see regions of virgin monofilament 105 with high tensile strength resulting from highly linearized molecular chains, notionally represented by lines roughly parallel to the suture axis, surrounding a weld region 110 with amorphous molecular orientation, notionally represented by random, disorganized lines. The tensile strength of the virgin monofilament is significantly stronger than that of the re-melt region. When tension is placed on the loop, the top and bottom portions of the overlapping loop ends load the weld region in shear, and since the area of the weld region is greater than the cross-section of the suture, the stress in this region is reduced as long as there is virgin high strength suture material on both sides of the weld region to distribute the load.

Tissue-Securing Devices of Molded Thermoplastic Material

Figures 4A, 4B:
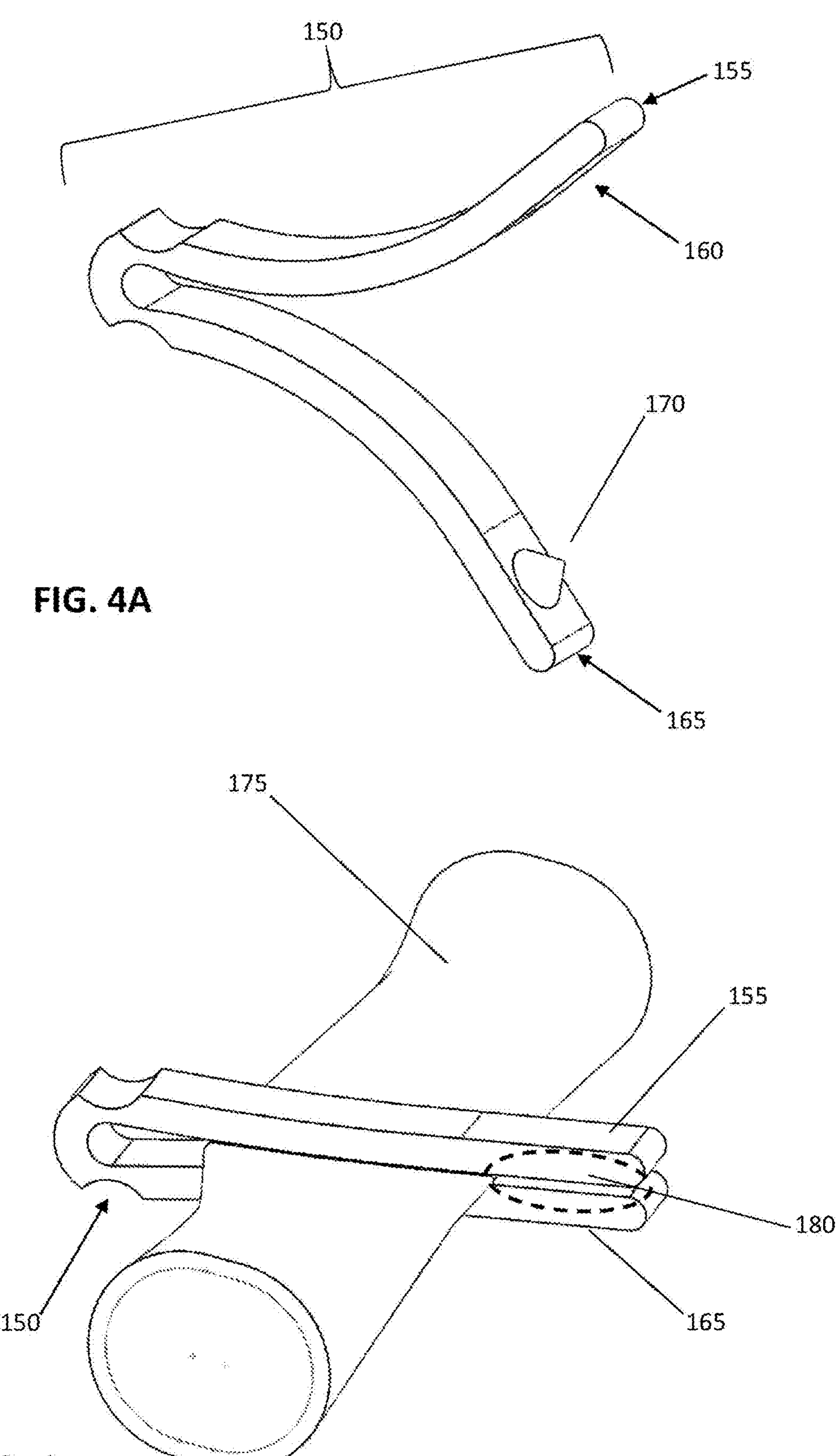
FIGS. 4A and 4B are schematic views showing a novel device made of molded conductive thermoplastic material that is intended to be electrically welded in situ.

FIGS. 4A and 4B show a clip 150 made of molded conductive thermoplastic material that may be electrically welded in situ, e.g., to occlude vessels such as veins and arteries for surgical hemostasis, or to clamp together tissue, etc. FIG. 4A shows clip 150 prior to deployment. Clip 150 comprises a first end 155 having a recess 160 and a second, opposing end 165 having a protruding feature 170. Protruding feature 170 on second end 165 mates with recess 160 on first end 155 so as to create a contact point of high resistance to initiate the weld melt. FIG. 4B shows clip 150 welded in situ around a blood vessel 175. Electrodes (not shown) applied to facing surfaces of first end 155 and second end 165 on clip 150 initiate a weld melt region 180 and bond first end 155 and second end 165 to one another so that clip 150 occludes blood vessel 175.

Figure 5A:
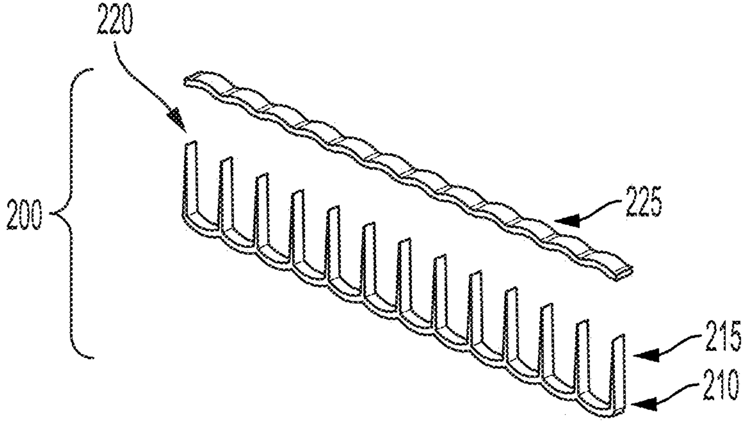
FIGS. 5A and 5B are schematic views showing another novel device made of molded conductive thermoplastic material that is intended to be electrically welded in situ.
Figure 5B:
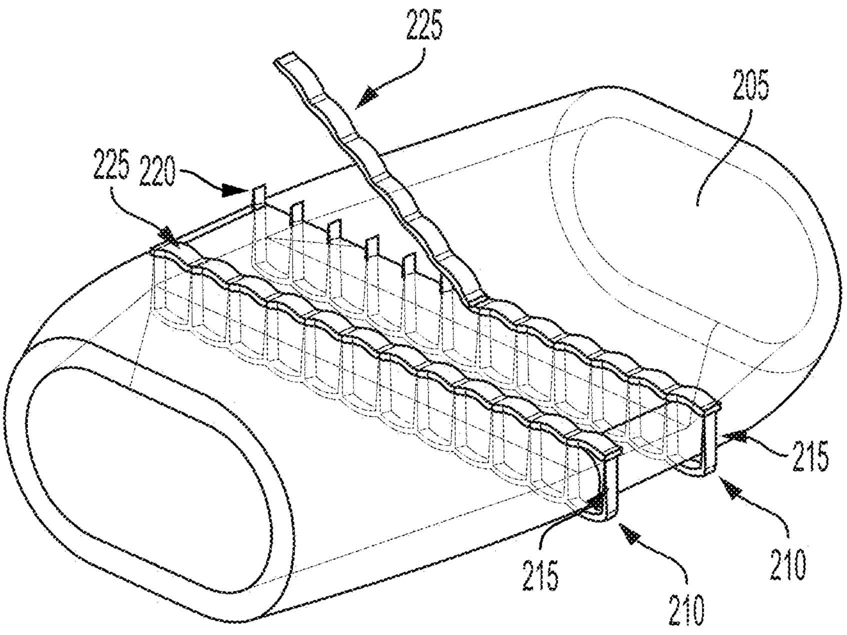

FIGS. 5A and 5B show another illustrative device 200 made of molded conductive thermoplastic material that is electrically welded in situ to occlude a section of a hollow organ 205, such as a stomach, to allow the organ to be surgically divided. Device 200 comprises (i) a first strip 210 having a row of conductive thermoplastic needles 215 terminating in needle tips 220, and (ii) a second strip 225 having counterpart recesses (not shown) for receiving needle tips 220. In this version of the invention, an apparatus (not shown) delivers first strip 210 of conductive thermoplastic needles 215 through two layers of the organ (i.e., through the two side walls of the hollow organ) and second strip 225 is welded to the needle tips 220 of first strip 210 after needle tips 220 have penetrated and emerged from the organ. By controlling the depth of melting of needles 215, the distance between the top portion (i.e., second strip 225) and bottom portion (i.e., first strip 210) of device 200 can be controlled, thereby controlling the degree of "squeeze" applied to the organ and accommodating organs with variable thickness. In this way, welded surgical fasteners functionally similar to a row of stitches or surgical staples may be delivered in a continuous linear process.

Suturing and Ligating Instruments

Figures 6, 7A:
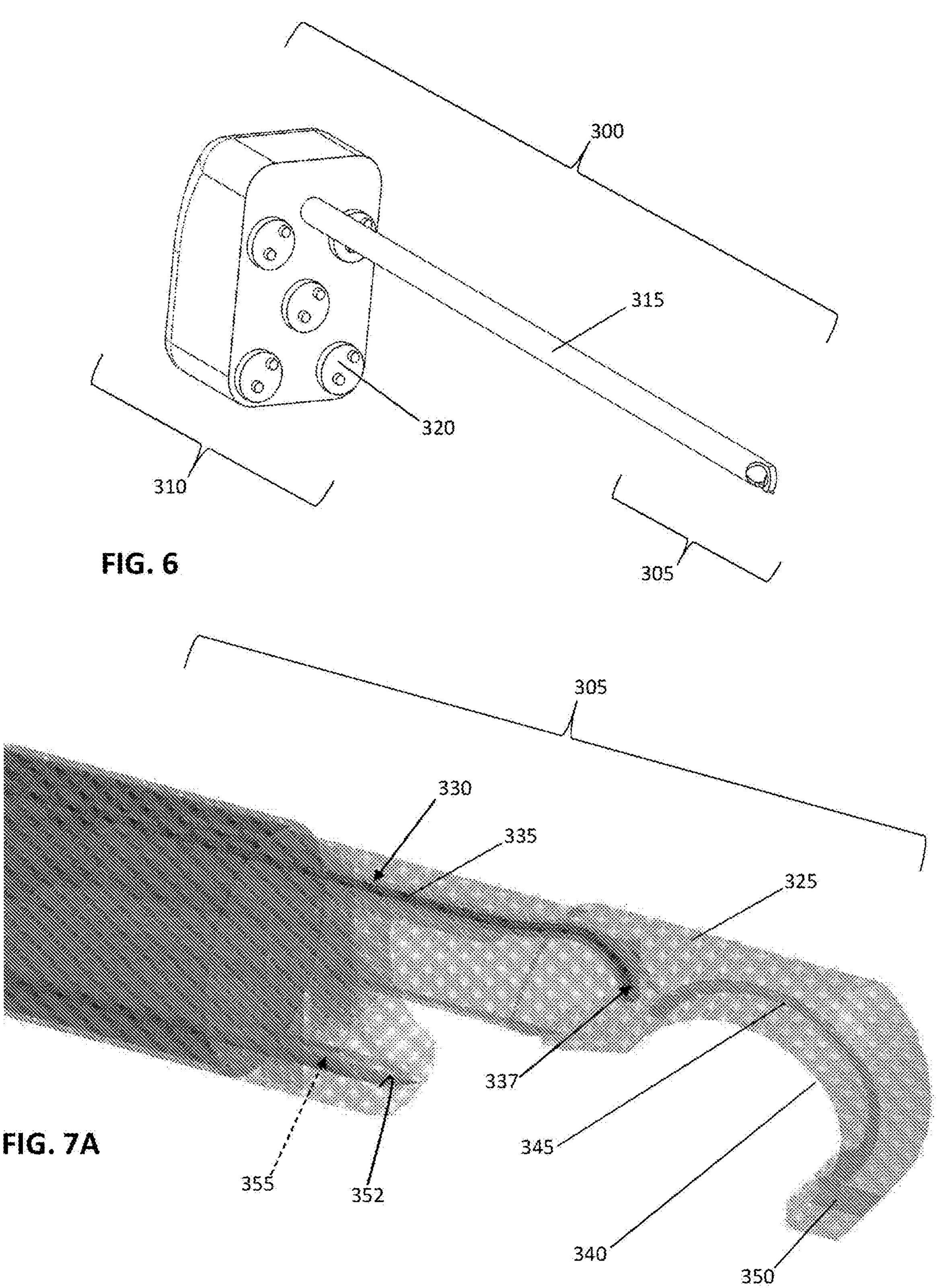
FIG. 6 is a schematic view showing a novel suturing instrument for use in surgery.
FIG. 7A is a schematic view showing the distal end effector portion of the novel suturing instrument of FIG. 6.

FIG. 6 shows a suturing instrument 300 for surgery comprising a distal end 305 and a proximal end 310 connected by a shaft 315. Distal end 305 is an end effector and includes mechanical and electrical means for manipulating tissue and suture material for the formation of surgical stitches. Proximal end 310 contains actuating means for driving and operating the stitch-forming means at distal end 305 through wires and linkages (not shown in FIG. 6) passing through shaft 315. Shaft 315 has sufficient length to reach anatomical structures within the interior of a body, with proximal end 310 of the instrument remaining outside of a body, distal end 305 reaching target tissue at a surgical site, and shaft 315 passing through intervening tissue and spaces, e.g., by passing through a small incision in a body wall such as the abdominal wall. In one version (not shown), proximal end 310 of instrument 300 includes a handle adapted to be held by a human hand and the actuating means on proximal end 310 includes various buttons, triggers, levers, etc. for controlling the stitch-forming means at distal end 305, and a battery for supplying power to weld the suture. In another version (also not shown), the handle contains motors, linear actuators, pneumatic or hydraulic cylinders, or other actuation means to drive the stitch-formation means, a microprocessor-controlled circuit to sequence the stitch formation and welding, a trigger or button to initiate the stitch formation process, and a battery to power the actuators and circuit. Still other versions have a handle and external power means such as a power cord or pneumatic or hydraulic hoses. In another version (shown), proximal end 310 includes electrical and/or mechanical interfaces 320 for connection to a surgical robot.

FIG. 7A shows a version of a distal end effector 305 for surgical stitching instrument 300 (or other surgical stitching instrument). Distal end effector 305 comprises a slidable grasper 325 for grasping a piece of tissue and means for passing and welding a loop of suture about the grasped tissue, as will be discussed in further detail below.

Slidable grasper 325 includes a passage 330 for passing a length of conductive thermoplastic polymer monofilament suture 335 (having a distal end 337) therethrough, a hook feature 340 with a groove 345 opening on the inside of hook feature 340, and a needle hole 350 aligning with groove 345 of hook feature 340. Slidable grasper 325 also comprises a bore 352 for passing a needle 355 therethrough.

Figure 7B:
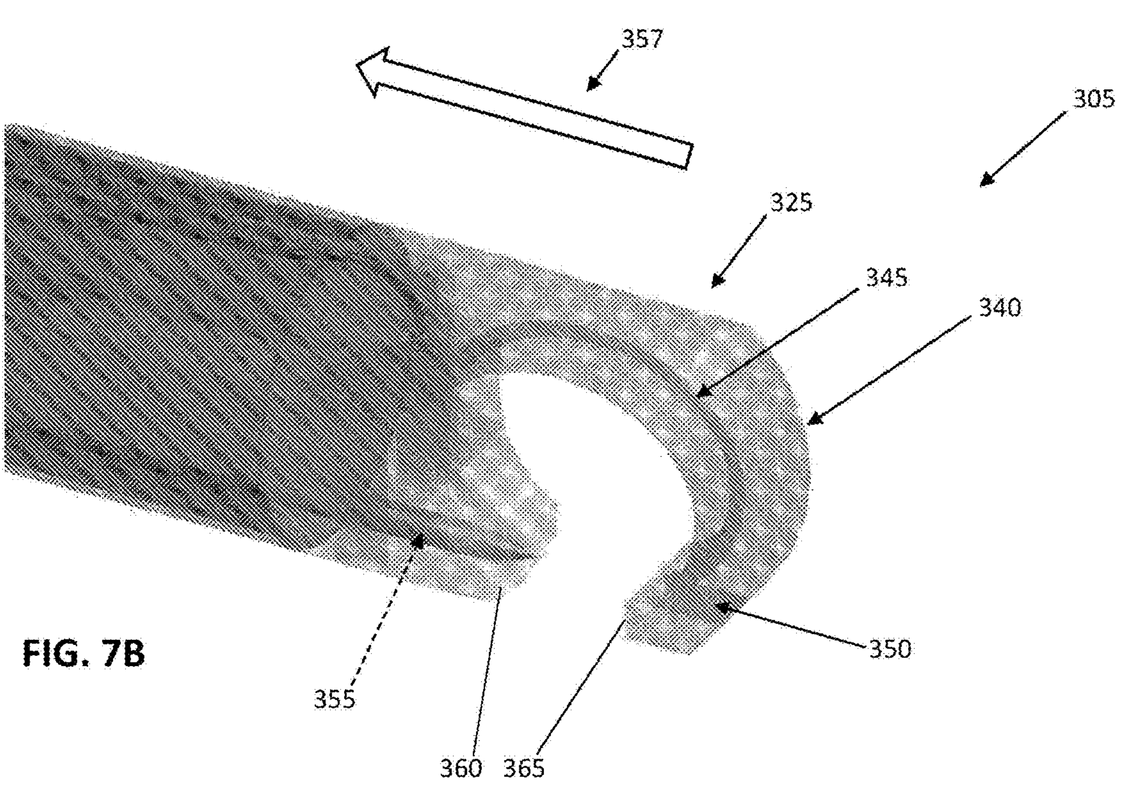
FIG. 7B is a schematic view showing actuation of the grasper portion of the distal end effector shown in FIG. 7A.

In use, and looking now at FIG. 7B, hook feature 340 of slidable grasper 325 is moved proximally (i.e., in the direction of arrow 357) so as to pinch the tissue to be sutured (not shown) between a first textured grasping surface 360 and a second textured grasping surface 365.

Figure 7C:
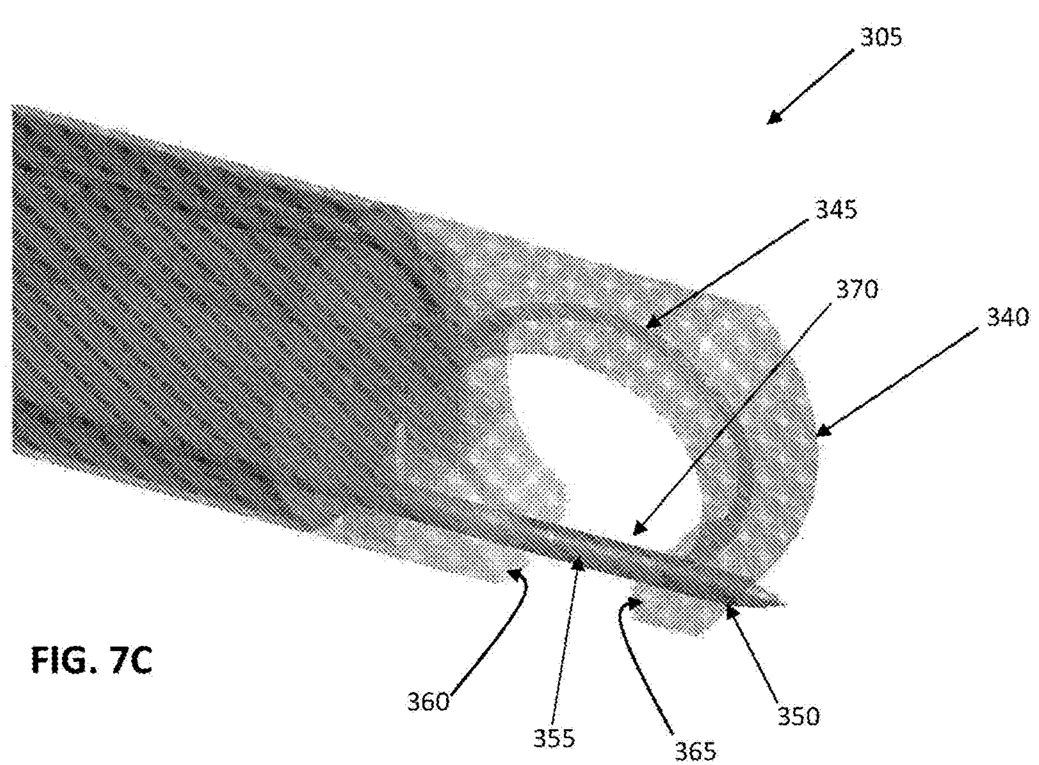
FIG. 7C is a schematic view showing a needle (having a groove) advanced through the tissue (not shown) pinched between the grasping surfaces of the distal end effector.

Looking now at FIG. 7C, needle 355 comprises a groove 370 so that after needle 355 has been advanced through the tissue (not shown) which is pinched between grasping surfaces 360, 365 and needle 355 is disposed in needle hole 350 of hook feature 340, groove 370 in needle 355 is aligned with groove 345 in hook feature 340, whereby to form a continuous circular path (i.e., by means of groove 345 of hook feature 340 and groove 370 in needle 355).

Figure 7D:
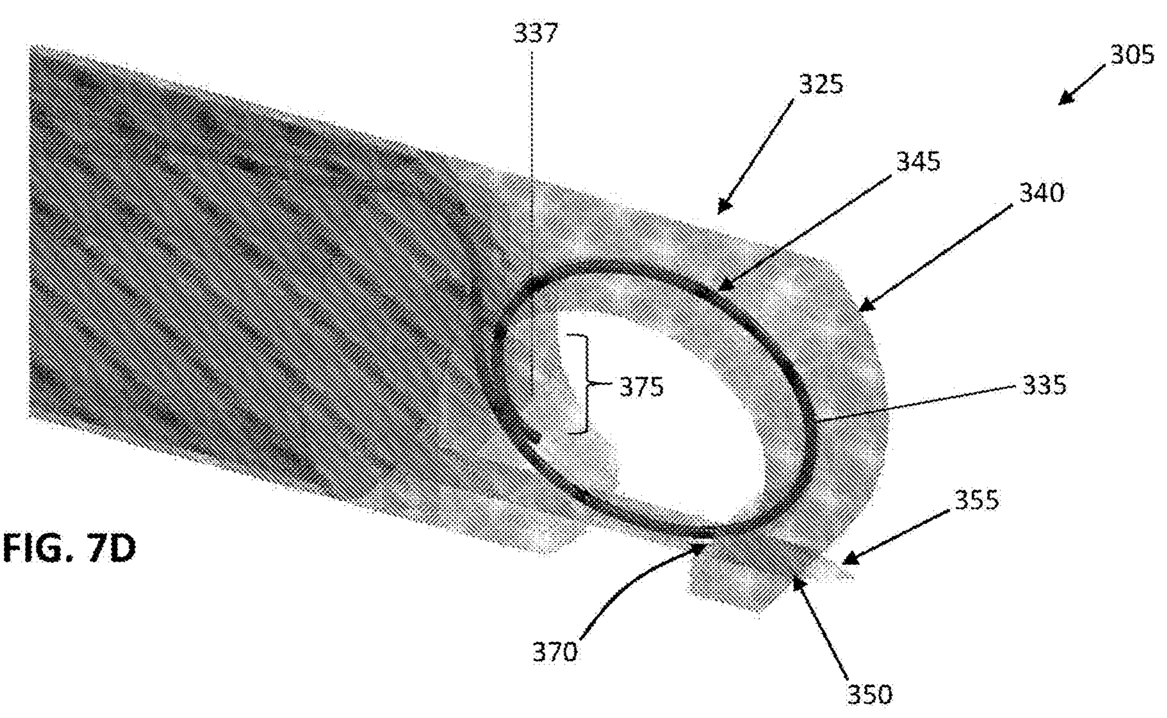
FIG. 7D is a schematic view showing the distal end effector of FIG. 7C, with a suture advanced by pushing the suture into the groove of the needle and a groove of the grasper.

Looking next at FIG. 7D, suture 335 may be advanced through the continuous circular path formed by groove 370 of needle 355 and groove 345 of hook feature 340 until distal end 337 of suture 335 passes back over a portion of suture 335 proximal to distal end 337, whereby to form a loop of suture passing through the tissue captured in distal end effector 305, with distal end 337 of suture 335 contacting the proximal portion of suture 335 at overlapping region 375. Suture 335 is advanced by motor-driven rollers in shaft 315 and/or proximal end 310 of instrument 300 which engage and push suture 335 through the circular path, or by other driving means in shaft 315 and/or proximal end 310 of instrument 300 (not shown) known to those skilled in the art.

After suture 335 has been advanced through the aforementioned circular path so as to form the loop of suture, an articulating gripping mechanism 400 may be used to firmly grasp distal end 337 of suture 335 adjacent the proximal portion of suture 335 at overlapping region 375, leaving proximal portion of suture 335 free to slide axially for tensioning. To this end, and looking now at FIG. 7E, articulating gripping mechanism 400 comprises a first lever 405 and a second lever 410 which pivot about pins 415 and 420, respectively. When suture 335 is being advanced through groove 370 of needle 355 and groove 345 of hook feature 340, levers 405, 410 are held apart, creating a gap in line with groove 370 in needle 355 and circular groove 345 of hook feature 340, thereby allowing distal end 337 of suture 335 to pass through the gap in order to form the loop of suture. After distal end 337 of suture 335 is in place at overlapping region 375, levers 405, 410 are closed on distal end 337 of suture 335, grasping distal end 337 and holding it firmly in place in overlapping region 375. Levers 405, 410 are made of a non-electrically-conductive material except for a first electrode 425 disposed where levers 405, 410 grip distal end 337 of suture 335. Electrode 425 only makes electrical contact with distal end 337 of suture 335.

Figure 7E:
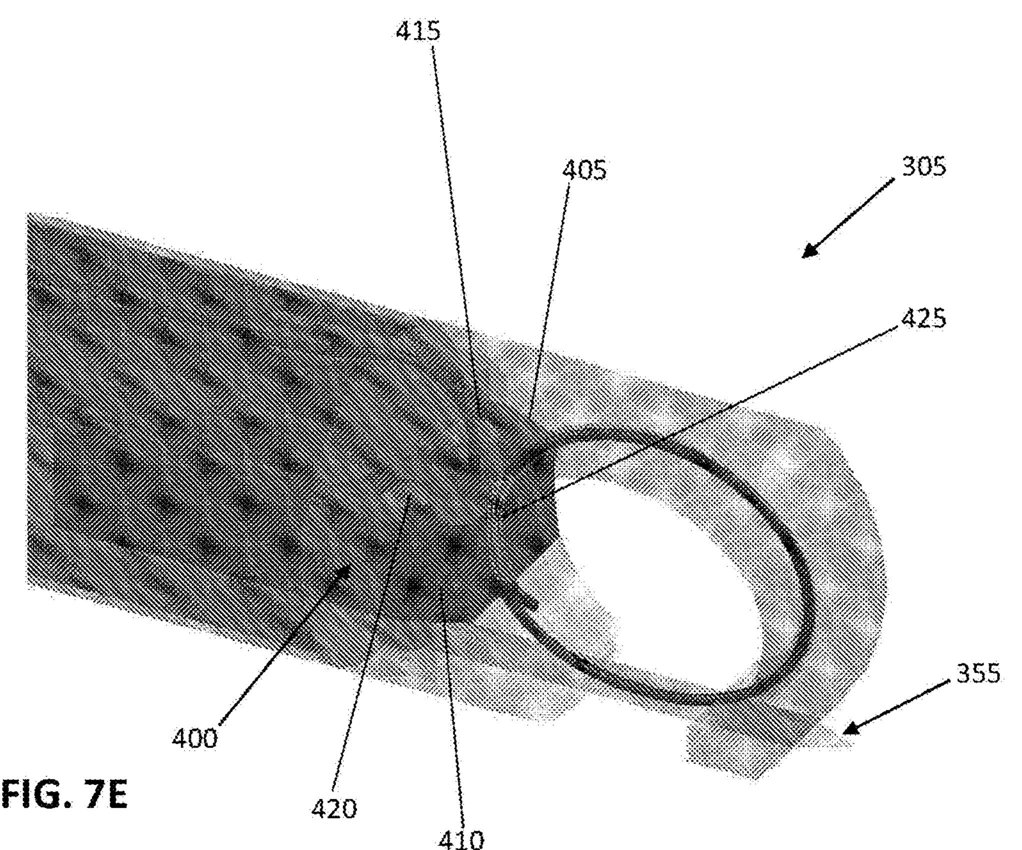
FIG. 7E is a schematic view showing actuation of the articulating gripping mechanism of the distal end effector of FIG. 7D.
Figure 7F:
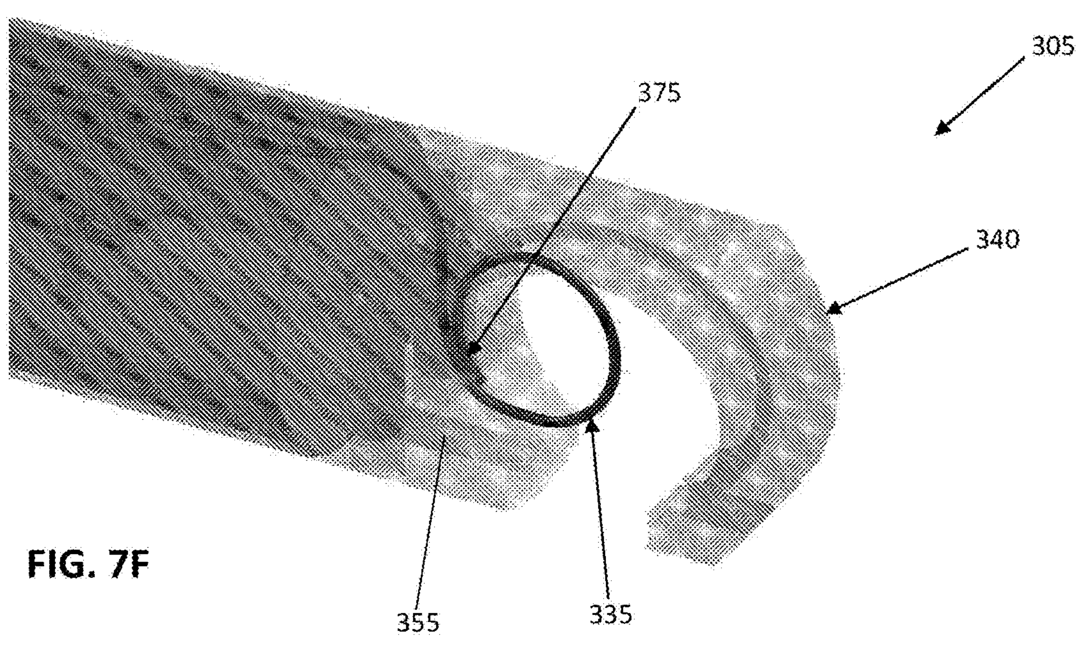
FIG. 7F is a schematic view showing the distal end effector of FIG. 7E, with the needle retracted and a suture advancement mechanism reversed.

After distal end 337 of suture 335 is clamped by levers 405, 410 in overlapping region 375, needle 355 is retracted and the suture advancement means that advanced suture 335 through the circular path is reversed so as to retract the loop of suture 335 and tighten the loop of suture 335 around the tissue grasped by slidable grasper 325 (FIG. 7F).

Figure 7G:
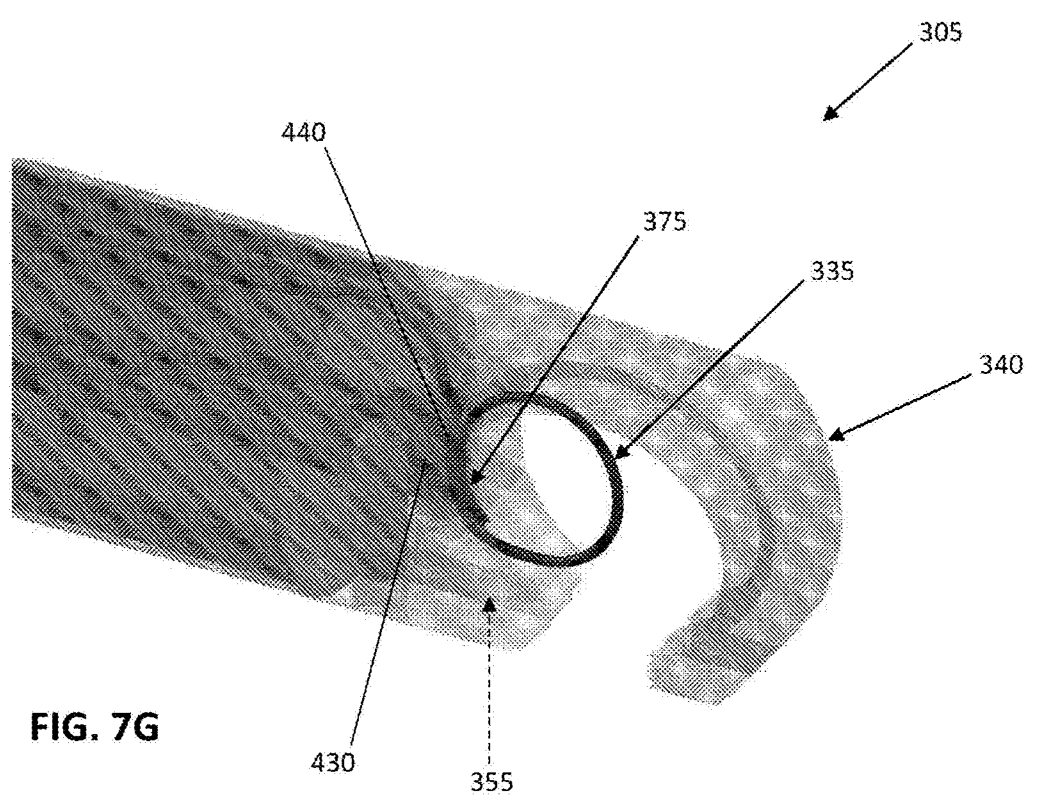
FIG. 7G is a schematic view showing the distal end effector of FIG. 7F, with an electrode advanced to contact a portion of the suture.

Once the loop of suture has been tightened around the tissue (not shown), a second electrode 430 is advanced to contact the portion of suture that overlaps with distal end 337 of suture 335 (i.e., portion 440 of FIG. 7G) in overlapping region 375. Voltage potential is applied across first electrode 425 and second electrode 430 and current flows across the overlapping suture region 375, thereby causing heating, melting and the formation of a weld in accordance with the method described above in relation to FIG. 2A.

After welding distal end 337 of suture 335 to the proximal portion of the suture at overlapping suture region 375, a knife blade 500 is advanced to cut the suture supply proximal to the weld so as to separate the welded loop from instrument 300 (FIG. 7H). Hook feature 340 of slidable grasper 325 is then moved distally so as to re-open slidable grasper 325, thereby releasing the pinched tissue. First lever 405 and second lever 410 are also separated to release the welded loop stitch 445 surrounding the tissue (FIG. 7I). The actuators at proximal end 310 of instrument 300 then return distal end effector 305 to the position of FIG. 7A and instrument 300 is ready to form another stitch.

It should be understood that a wide range of additional devices and systems can use the disclosed material, apparatus and method and are included in the scope of the present disclosure.

It will be appreciated that, if desired, suturing instrument 300 can be used for ligating tissue as well as for suturing tissue. By way of example but not limitation, in an exemplary ligating application, with suturing instrument 300 in the position shown in FIG. 7B, the instrument is slipped around the tissue (e.g., the vessel) which is to be ligated. Then needle 355 is advanced distally (FIG. 7C) so as to capture the tissue which is to be ligated in the space between slidable grasper 325, the shaft of suturing instrument 300 and needle 355. Then the suture is advanced through the aforementioned circular path (FIG. 7D) so that the looped suture surrounds the tissue which is to be ligated. Next, the looped suture is gripped by levers 405, 410 (FIG. 7E), needle 355 is retracted and the suture loop is tightened (FIG. 7F). Then the suture loop is welded (FIG. 7G), and excess suture is trimmed (FIG. 7H). Finally, the suture loop (and ligated vessel) are released from suturing instrument 300 (FIG. 7I). Note that for tissue ligating applications, needle 355 can have a blunt distal end if desired.

Suturing End Effector for Use in Robotic Surgery

Figures 8A, 8B:
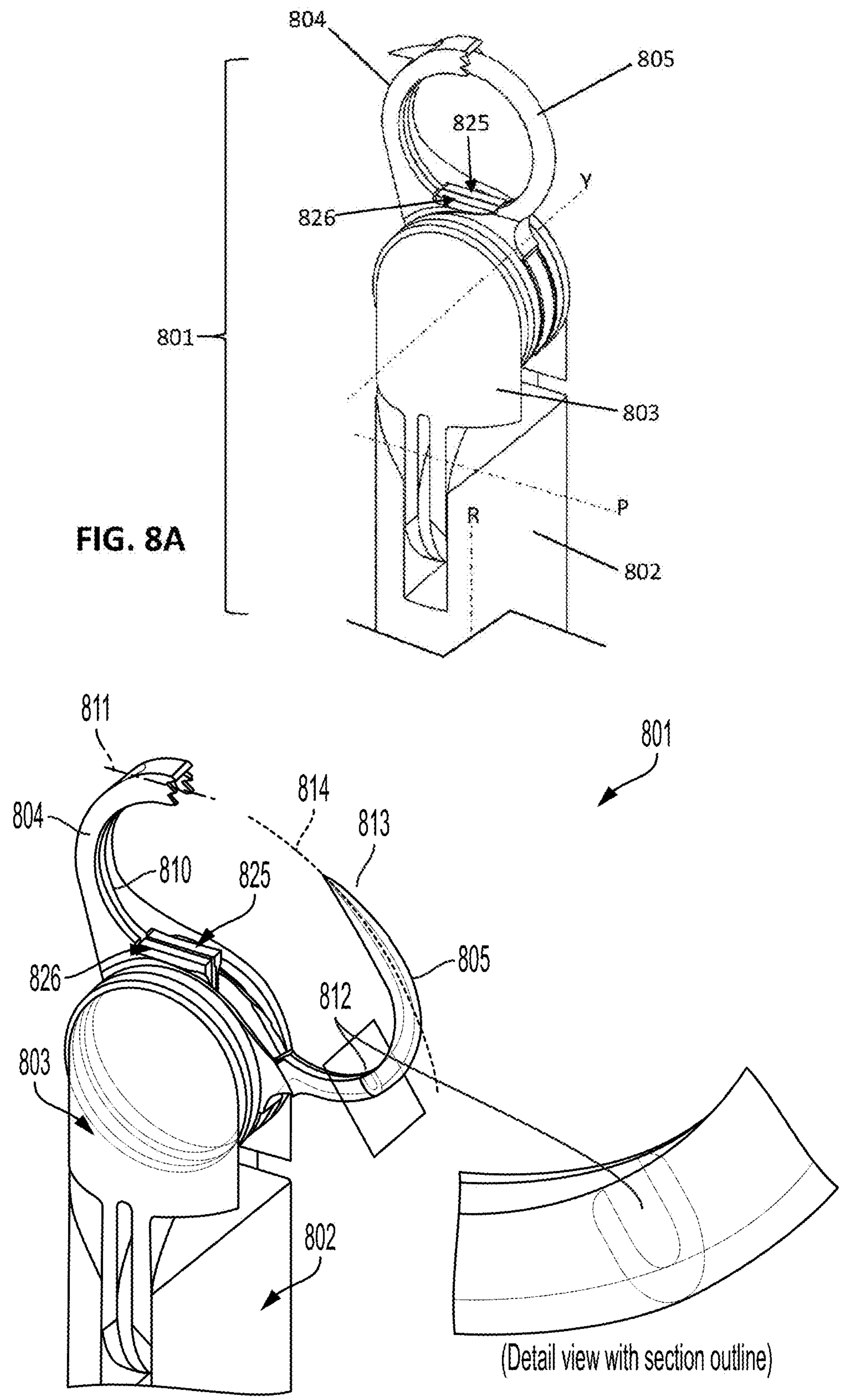
FIGS. 8A and 8B are schematic views showing a novel end effector for use in robotic surgery.

FIG. 8A shows a version of the present invention incorporated into a highly articulated end effector 801 for robotic surgery. This embodiment includes a four degree of freedom (DoF) slave-robot end effector controlled remotely by a surgeon stationed at a master-robot control console. The principal degrees of freedom include: an instrument shaft 802 rolling about axis R, a mid-section “knuckle” 803 articulating in pitch about axis P, and first (804) and second (805) independently rotating tool elements disposed in opposition to each other, each rotating about yaw axis Y. Other robotic end effectors employ articulating segments or other means to achieve four or five DoF motion, and the present invention applies to these devices also. The end effector described thus far in this paragraph is known to the art and is in common usage in robotic surgery. We will now describe novel aspects unique to the present invention.

FIG. 8B shows an embodiment of the present invention that forms a suture stitch in the same manner as the invention described in FIGS. 7A through 7I, but differs through the addition of a highly articulated end effector (e.g., the end effector of FIG. 8A). In an embodiment, first articulating opposed tool element 804 is a semi-circular shaped rigid body with an inward facing groove 810 terminating in a needle hole 811 at its distal end. Second tool element 805 is a semi-circular shaped needle with an inward facing suture groove 812 and a sharp tissue penetrating point 813 on its distal end. The distal portion of the needle 805 (i.e., second tool element 805) has a radius 814 to align with needle-receiving hole 811 in tool element 804. When first and second tool elements 804 and 805 are closed in opposition (as shown in FIG. 8A), inward facing grooves 810 and 812 form a continuous groove through which suture may be advanced.

Figures 8C, 8D, 8E, 8F:
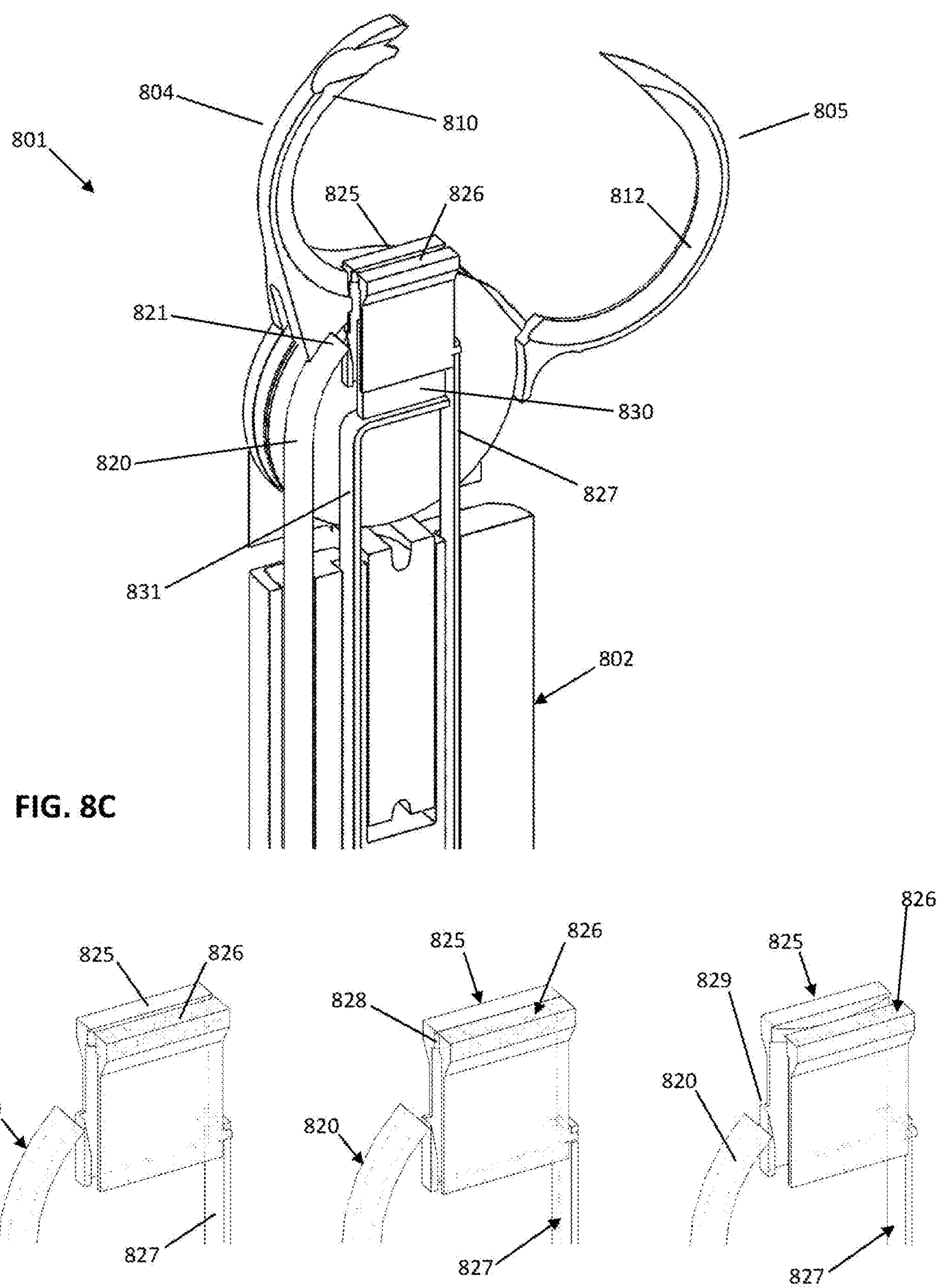
FIGS. 8C-8F are schematic views showing further details of the novel end effector shown in FIGS. 8A and 8B.

FIG. 8C shows a partial section view of an embodiment of the present invention schematically displaying the means for forming a suture stitch with the end effector. A flexible suture delivery tube 820 aligns with grooves 810 and 812 in opposing tool elements 804 and 805 when tool elements 804 and 805 are closed in opposition. The distal end 821 of the suture delivery tube 820 is fixed relative to first tool element 804 (in other embodiments the mechanism may be reversed and delivery tube 820 may be fixed to second tool element 805). The flexibility of the suture delivery tube 820 allows the suture delivery tube to maintain its alignment with first tool element 804 throughout the full range of motion of the articulating end effector. The flexible suture delivery tube 820 serves the same purpose as the suture passage 330 described in FIG. 7A, with the difference of being flexible and allowing articulation of the end effector.

FIGS. 8D, 8E and 8F show detail views of suture grippers 825 and 826. Suture grippers 825 and 826 provide multiple functions in the suture formation process. In an embodiment they are arranged on a ramped guide surface provided on the end effector (not shown in FIGS. 8D, 8E and 8F, but of the sort well known to those skilled in the art of gripping mechanisms) such that they separate as grippers 825 and 826 move distally and come together as they move proximally. Their movement is controlled by flexible gripper actuation linkage 827 which has sufficient flexibility to actuate the grippers throughout the full range of motion of the end effector. The grippers 825 and 826 move into three distinct positions: feed position (FIG. 8D) where the grippers are separated partially to allow suture to pass between them, clamp/weld position (FIG. 8E) where steps 828 in the gripper surfaces come together to clamp and hold the distal end of the suture strand (i.e., the overlapping portions of the suture strand) for loop tensioning and welding, and release/cut position (FIG. 8F) where the grippers separate wide enough to release the welded loop of suture and sharp cutter surface 829 slides distally to snip the welded suture loop free of the suture supply exiting feed tube 820.

FIG. 8C also shows weld electrode 830 actuated distally and proximally by flexible electrode linkage 831 which has sufficient flexibility to control movement of the weld electrode throughout the full range of motion of the end effector. In an embodiment the suture grippers 825 and 826 are electrically insulated except for the distal surfaces of the grippers contacting the distal side of the overlapping conductive suture segments held in the clamped position. The electrode 830 is electrically insulated except for a portion of the distal surface which can be brought into contact with the proximal side of the overlapping conductive suture segments held in the clamped position. In an embodiment either or both flexible actuation linkages 827 (of grippers 825 and 826) and 831 (of electrode 830) are insulated, and conductive and arranged to deliver electrical energy to either the grippers or the electrode or both. In other embodiments separate flexible insulated wires deliver electrical energy to either or both grippers 825 and 826 and/or electrode 830. In embodiments where only one element (i.e., the grippers 825 and 826, or the electrode 830) has an insulated conductor, the other element (i.e., the electrode 830, or the grippers 825 and 826) may be connected to ground through the instrument shaft and connected components. Electrical potential is applied between the non-insulated portions of the gripper surfaces and the electrode, causing current to flow through the overlapping conductive suture segments, thereby causing localized melting at the interface between the suture segments, resulting in a welded connection between the suture segments. Where the overlapping conductive suture segments are either end of a continuous suture loop, a welded stitch is formed.

Note that, if desired, end effector 801 can be used for tissue ligating as well as tissue suturing. By way of example but not limitation, where end effector 801 is to be used to ligate tissue (e.g., a vessel), arms 804, 805 are deployed around the tissue so as to envelope the tissue without penetrating the tissue. In this way, the suture loop is positioned around the tissue prior to suture tightening and welding.

FIGS. 8G-8M show an embodiment of the present invention that eliminates the need for flexible gripper actuation linkage 827 and flexible electrode linkage 831 adjacent to actuating grippers 825 and 826 and electrode 830, by using a cam (see below) linked to the relative movement of tool element 804 and needle 805 to move grippers 825 and 826. The benefits of this alternative arrangement include (i) design simplification, and (ii) a reduction in the total number of actuators (or DoFs) needed to complete a stitch, i.e., a reduction by two in the total number of actuators needed to complete a stitch (i.e., two fewer actuators or DoFs are needed to complete a stitch using this alternative arrangement).

Figure 8G:
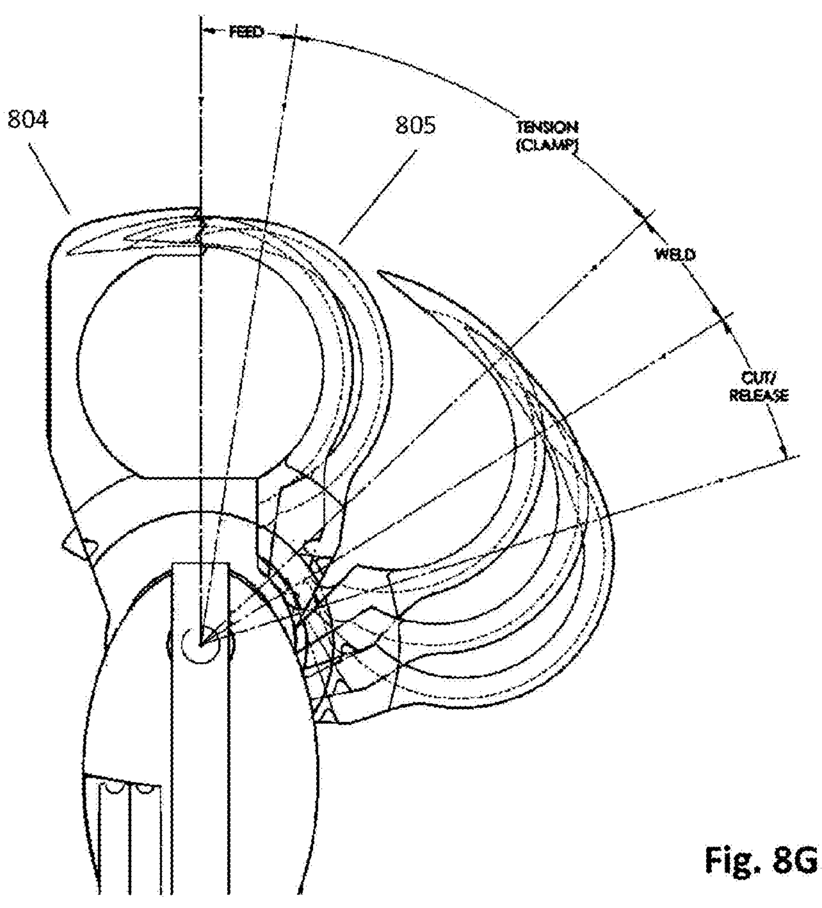
FIGS. 8G-8M are schematic and partial section views showing another form of the invention.

FIG. 8G shows the distal portion of an end effector, the relative angular relationship between tool element 804 and phantom images of needle 805, with the phantom images of needle 805 divided into four regions or positions: (i) feed, (ii) tension (or clamp), (iii) weld and (iv) cut/release.

Figure 8H:
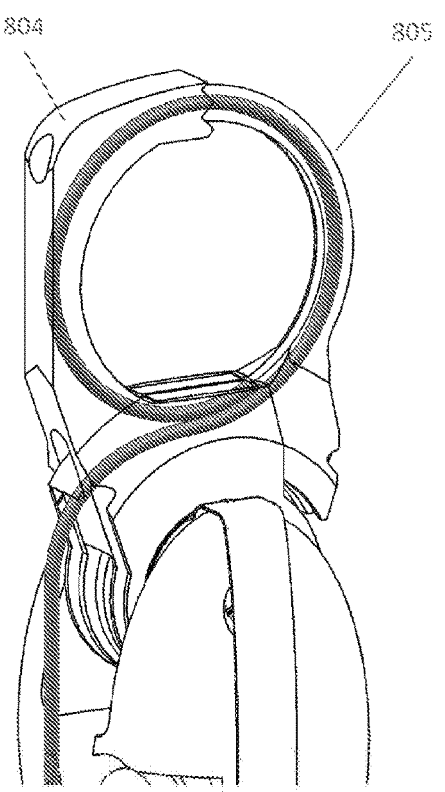

FIG. 8H shows suture having been fed into the inward-facing groove 812 in needle 805, in a manner similar to that shown in FIG. 7D.

Figure 8I:
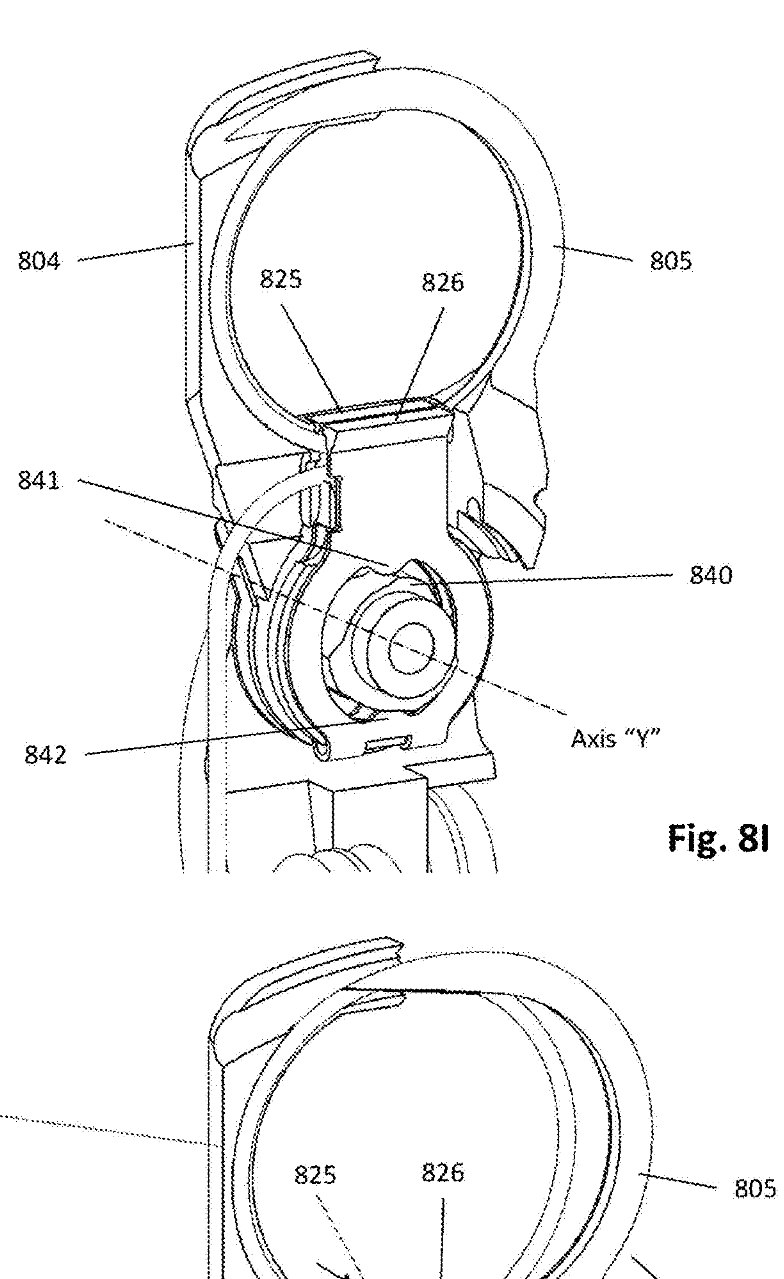

FIG. 8I shows a partial section view of the inner workings of the hub defined by axis Y, which is the rotational axis of tool element 804 and needle 805, and showing a cam 840 which is part of, or carried by, needle 805 and therefore rotates with needle 805. In a manner similar to that shown in FIG. 8D, we can see in FIG. 8 grippers 825 and 826 are positioned slightly open by cam 840 bearing against follower surfaces 841 and 842 (which are part of the grippers 825 and 826).

Figure 8J:
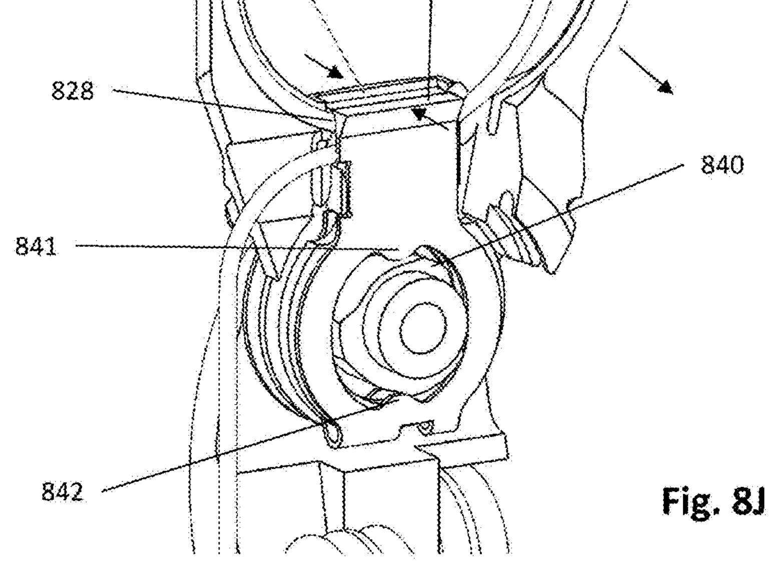

FIG. 8J shows needle 805 and cam 840 (connected to needle 805) rotated slightly past the “feed” zone (see FIG. 8G) and rotated into the “tension (or clamp)” zone (see FIG. 8G), such that cam 840 forces the grippers 825 and 826 in a proximal direction where a ramped surface closes the gap between the grippers, causing stepped surfaces 828 of grippers 825 and 826 to grip the distal end of the suture, in a manner similar to that shown in FIG. 7E, so that the suture may be tensioned.

Figure 8K:
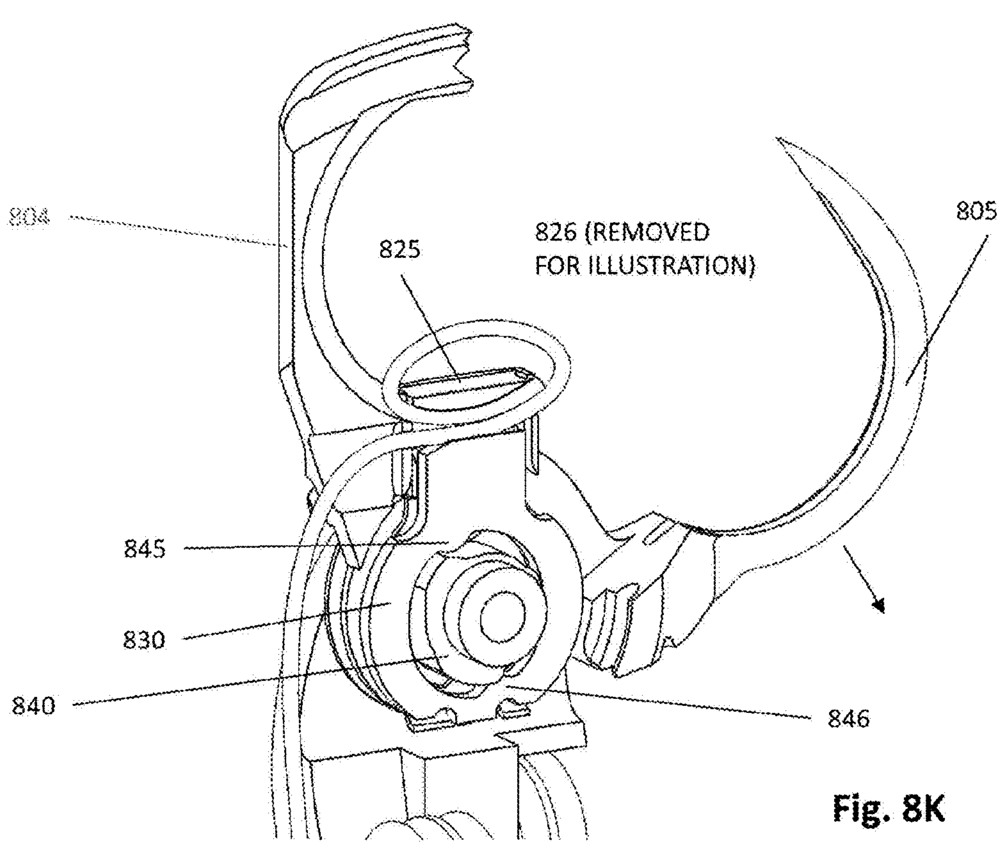

FIG. 8K shows the suture having been tensioned in a manner similar to that shown in FIG. 7F, and needle 805 further rotated to a position in the “tension (or clamp)” zone (see FIG. 8G) just before the “weld” zone (see FIG. 8G). FIG. 8K further shows weld electrode 830 sandwiched between grippers 825 and 826 (near-side gripper 826 has been removed from this section view to allow visualization of electrode 830). Electrode 830 has cam follower surfaces 845 and 846 which are rotationally advanced from gripper follower surfaces 841 and 842 such that electrode 830 moves before grippers 825 and 826 move as needle 805 and cam 840 rotate, thereby allowing a single cam surface to perform multiple functions in sequence (i.e., to move grippers 825 and 826, and then moving electrode 830). In other embodiments, multiple cam lobes may be employed to accomplish this same sequenced operation.

Figure 8L:
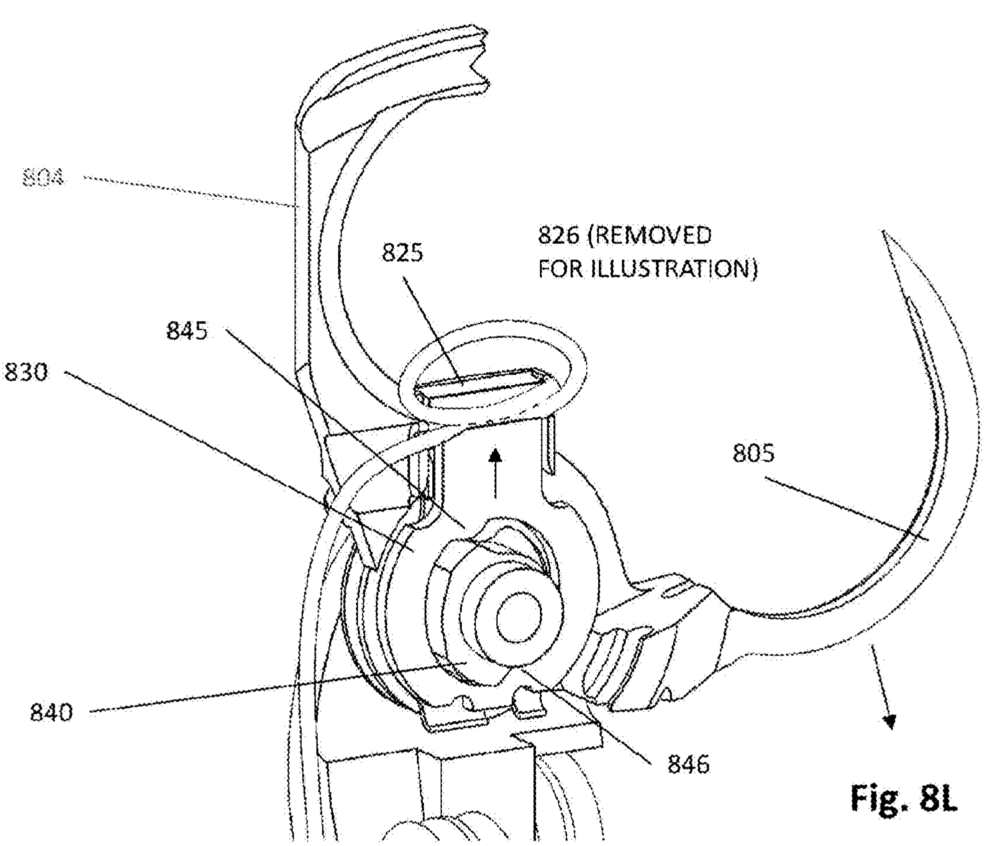

FIG. 8L shows needle 805 and cam 840 rotated into the “weld” zone (see FIG. 8G). In FIG. 8L we see grippers 825 and 826 (again, near-side gripper 826 has been removed from this section view to allow visualization of electrode 830) still gripping the distal end of the suture while electrode 830 has been advanced so as to compress the overlapping portion of the suture loop. In a manner similar to FIG. 7G, electrical current is then applied across the overlapping portion of the suture loop through (i) conductive surfaces on grippers 825 and 826, and (ii) electrode 830, thereby causing a weld to form in the overlapping portion of the suture loop.

Figure 8M:
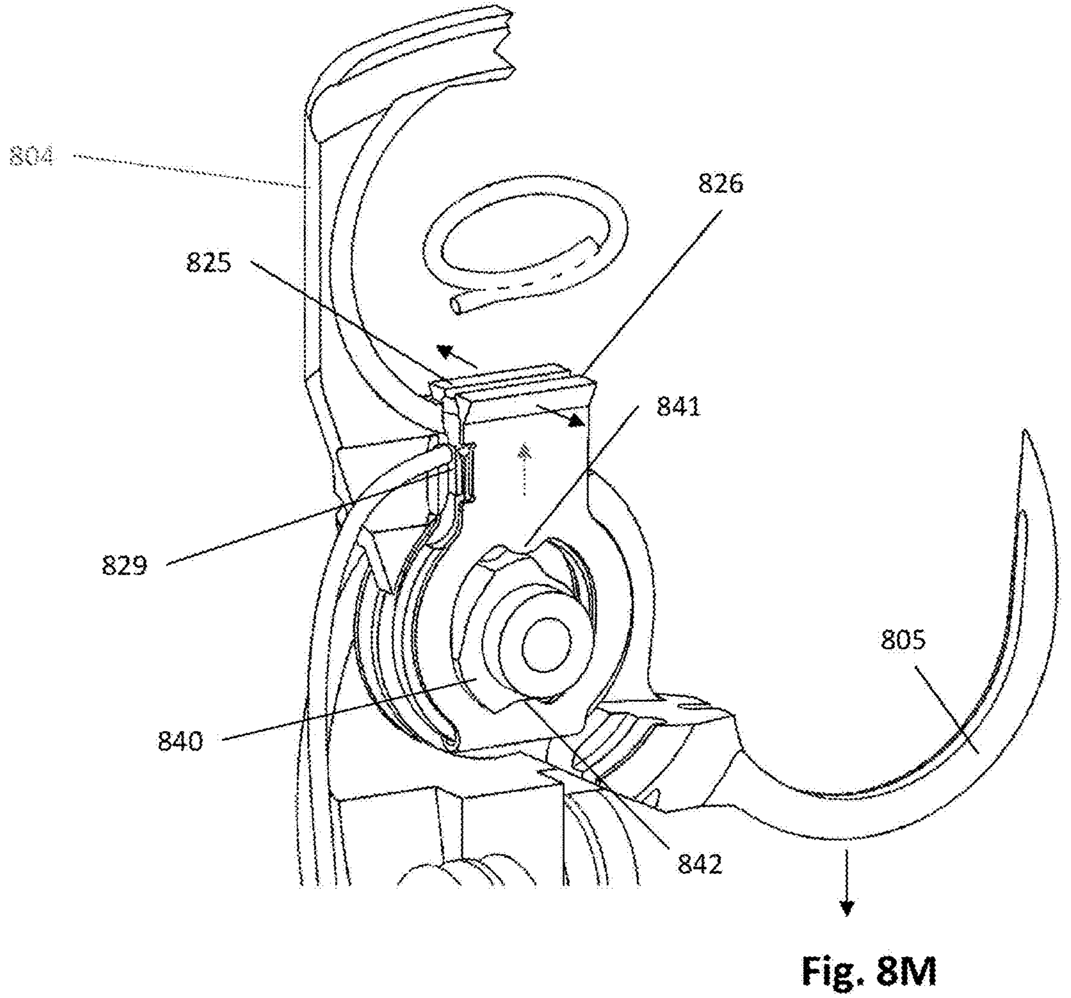

FIG. 8M shows needle 805 and cam 840 rotated into the "cut/release" zone (see FIG. 8G). In FIG. 8M, we see grippers 825 and 826 (near-side gripper 826 is no longer removed from this view) advanced distally by cam 840, causing the gripping surfaces to separate, while at the same time advancing sharp cutter surface 829 across the suture feed opening, thereby cutting the suture loop free from the suture supply and releasing the stitch (i.e., the welded suture loop) from the suturing instrument.

It will be appreciated that needle 805 may be moved through its aforementioned operating positions in a variety of ways which will be well known to those skilled in the art in view of the present disclosure, e.g., needle 805 may be caused to pivot about a pivot axis by advancing and retracting an actuating rod.

FIGS. 9A-9E illustrate an embodiment of the present invention in a body as it might be viewed by a surgeon at a robotic control console.

Figures 9A, 9B, 9C, 9D, 9E:
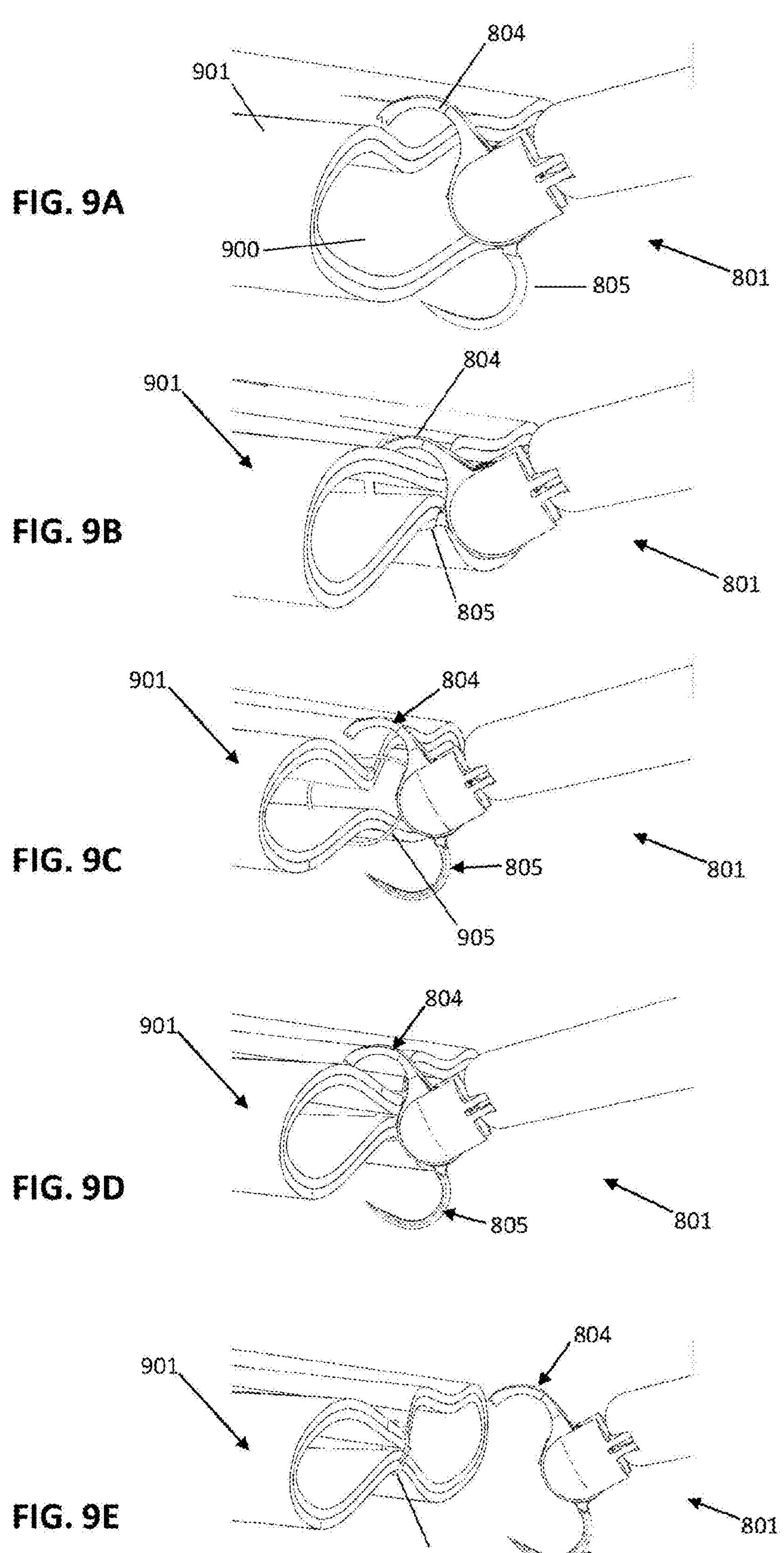
FIGS. 9A-9E are schematic views showing an anatomical closure being effected with the novel end effector shown in FIGS. 8A and 8B.

FIG. 9A shows an opening 900 in tissue 901 that the surgeon would like to close with a stitch. The surgeon's hand and wrist movements at the master-robot on the control console are replicated by the instrument end effector 801 in the body. The surgeon's thumb and forefinger movements are replicated by the tool element 804 and the needle 805. The surgeon positions the tool element 804 and needle 805 astride the tissue opening to be stitched.

FIG. 9B shows the tool element 804 and needle 805 closed in opposition in response to the surgeon bringing their thumb and forefinger together. The needle 805 has penetrated through both sides of the tissue opening, completing a continuous circular groove (i.e., the conjoined circular grooves 812 and 810) from the needle 805 to the tool element 804. If they are happy with the stitch location defined by the needle placement, the surgeon initiates the stitch process by depressing a footswitch, or a voice-activated command, or other means available to initiate action. In an embodiment the stitch process is a fully automated sequence. In other embodiments some steps are automatically initiated in sequence and others are initiated by the surgeon. The first step in this sequence is activation of a suture advancing mechanism connected to the flexible suture delivery tube 820, which advances a fixed length of conductive suture equal to the circumference of the continuous inward facing groove of the tool element 804 and needle 805 (i.e., the conjoined circular grooves 810 and 812), plus additional material to form an overlapping region for the suture loop. The next step in the sequence is activation of an actuating mechanism connected to the flexible gripper actuation linkage 827 and the suture grippers 825 and 826 to move the grippers from the feed position (FIG. 8D) to the clamp/weld position (FIG. 8E), thereby gripping the distal end of the advanced suture in the overlap region.

FIG. 9C shows the tool element 804 and needle 805 opened and released from the tissue leaving conductive suture 905 threaded through both sides of the tissue opening. In an embodiment this motion is controlled by the surgeon at the control console by separation of their thumb and forefinger. In another embodiment, the separation of the tool element 804 and needle 805 is automatically initiated by the robot as part of the automated stitching process.

FIG. 9D shows the suture loop tensioned by reversal of the suture advancing mechanism. In an embodiment, tensioning is initiated automatically and suture is pulled to a predetermined or programmed tension value. In another embodiment, the surgeon controls the tensioning process through a control means such as a trigger, slide mechanism, foot switch or similar means. In an embodiment, the control means includes tactile haptic feedback such that the surgeon has the sensation of pulling on the suture to achieve the desired tension of the stitch. In an embodiment where the separation of the tool element 804 and the needle 805 is performed automatically by the robot, the surgeon controls and feels tension through haptic feedback by separation of their thumb and forefinger which is temporarily disengaged from controlling the motion of the tool element 804 and needle 805. Once desired or predetermined tension has been achieved, the weld process is initiated by initiation of an actuator connected to the flexible electrode linkage 831. The electrode 830 is brought into contact with the proximal side of the overlapping region of the conductive suture loop with a predetermined contacting force. Electrical current is then passed through the overlapping region (i.e., by passing an electrical current between electrode 830 and grippers 825 and 826), causing the interface between the suture segments in the overlapping region to locally melt and fuse into a weld.

FIG. 9E shows the final step of the stitching sequence where the tensioned, welded loop 906 has been cut free from the suture supply exiting the suture delivery tube 820 and released from the end effector by actuation and movement of the suture grippers 825 and 826 from the clamp/weld position (FIG. 8E) to the cut/release position (FIG. 8F).

Figures 10A, 10B, 10C, 10D, 10E:
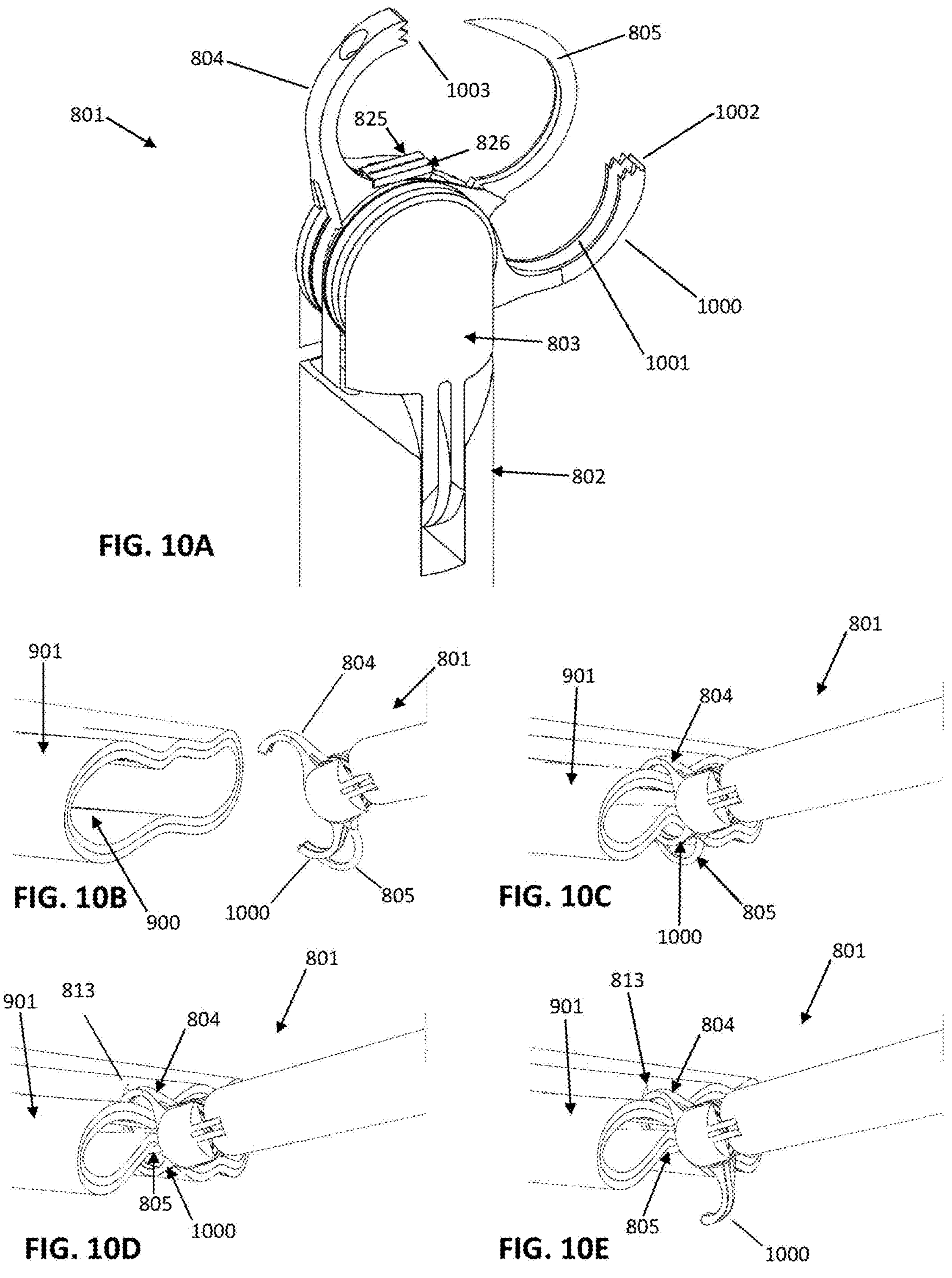
FIG. 10A is a schematic view showing another novel end effector for use in robotic surgery.
FIGS. 10B-10E are schematic views showing an anatomical closure being effected with the novel end effector shown in FIG. 10A.

FIG. 10A shows an embodiment with integrated tissue grasping and manipulation capability. This embodiment of an end effector has a first tool element 804, a needle 805, and a second opposing hollow tool element 1000. Hollow tool element 1000 includes an opening 1001 which is sufficiently large for needle 805 to rotate through, and a blunt or textured, non-tissue-penetrating end 1002 that directly opposes and aligns with a matching blunt or textured non-tissue-penetrating end 1003 on tool element 804.

FIGS. 10B through 10*e* show an embodiment of end effector with tissue grasping and manipulation capability (i.e., the end effector of FIG. 10A) as it might be viewed in a body by a surgeon at a robot control console.

FIG. 10B shows first and second opposing tool elements 804 and 1000 separated in preparation for grasping tissue. Needle 805 is outside hollow tool element 1000 and needle point 813 (not shown in FIG. 10B) protected in hollow opening 1001. The motion of the opposing tool elements is controlled by the movement of the surgeon's thumb and forefinger, and needle 804 moves with, and maintains its protected orientation with hollow tool element 1000, while the surgeon grasps and manipulates tissue as one might do with surgical forceps.

FIG. 10C shows the opposing tool elements 804 and 1000 grasping tissue at a location where the surgeon would like to place a stitch. The non-tissue-penetrating ends of the opposing tool elements 804 and 1000 pinch the tissue at the exact spot where the needle 805 will penetrate, thereby facilitating easy entry and penetration by the needle 805. When satisfied with the location, the surgeon initiates the stitching process by depressing a foot switch, using a voice command or other means to initiate the automated sequence. The first step in the sequence is activation of an actuator that "fires" the needle 805 through the tissue.

FIG. 10D shows needle point 813 penetrating the tissue and seated in needle hole 811 in tool element 804, and establishing (in conjunction with tool element 804) an uninterrupted suture groove (i.e., the conjoined circular grooves 810 and 812) through the tissue.

FIG. 10E shows hollow tool element 1000 retracted from the tissue, either by action on the part of the surgeon or automatically as part of the automated stitch sequence, leaving needle 805 in place (i.e., passed through the tissue and seated in needle hole 811 in tool element 804). The remainder of the stitch sequence is the same as that described in FIGS. 9B through 9E.

Suture Feeding and Tensioning Mechanism and Replaceable Suture Cartridge

Figure 11:
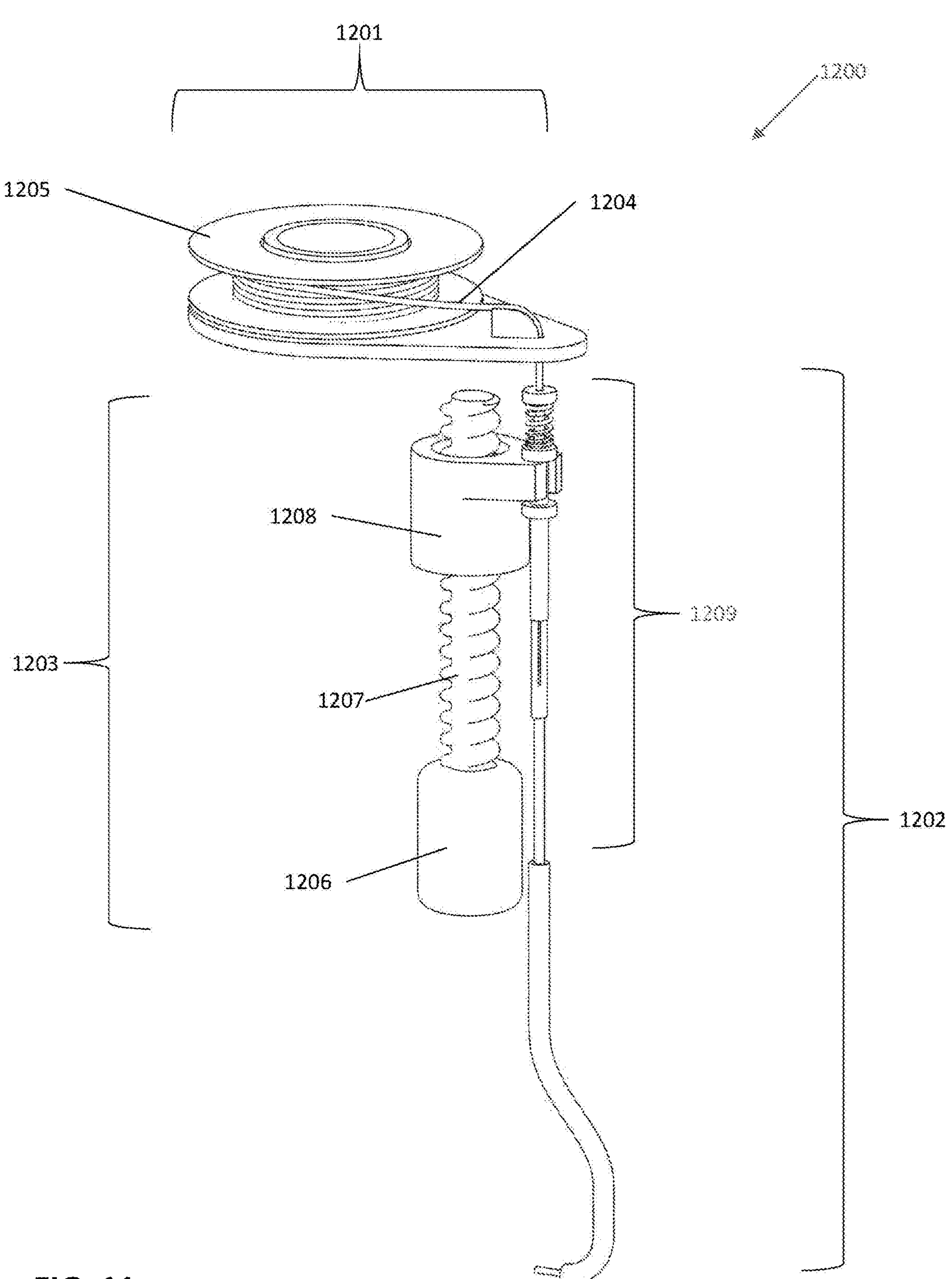
FIG. 11 is an isometric schematic view of an embodiment of a suture feeding and tensioning means for an automated suturing and/or ligating instrument.

FIG. 11 shows an embodiment of a suture feeding and tensioning mechanism 1200 for (i) advancing suture so as to form a loop configuration, and (ii) retracting the suture when it is in the loop configuration so as to tension the suture. In one form of the invention, suture feeding and tensioning mechanism 1200 comprises a supply 1201 of weldable suture filament, a means 1202 for guiding the suture to an end effector, and a reversible suture driving means 1203 for advancing/retracting the suture.

In the embodiment shown, the supply of weldable suture filament 1204 is wound on a freely rotating spool 1205. In other embodiments, the supply may be in the form of a free coil of suture, a straight length of suture, or any other form of containment from which suture filament may be drawn.

In the embodiment shown, a means 1202 is provided for guiding the suture to an end effector. This means 1202 comprises a system of tubing (rigid, flexible, or a combination of both) with an inside diameter which is slightly larger than the diameter of the suture filament 1204. In other embodiments, the means for guiding the suture may be one or more passages machined or molded into the internal componentry of an instrument. In embodiments with articulating end effectors, a flexible section of tubing may be used at the distal end to guide the suture through the end effector's one or more articulating joints. In some embodiments where articulation movement of the end effector changes the distance between (i) the feeding and tensioning mechanism 1200 and (ii) the end effector, the suture guiding means 1202 and/or the entire suture feeding and tensioning mechanism 1200 moves axially within the instrument to maintain a constant length of suture filament. In other embodiments, a computer calculates changes in suture guide passage length based on articulation angles and compensates for the changes in guide passage length by repositioning the actuator.

In the embodiment shown, a reversible suture driving means 1203 is provided. Reversible suture driving means 1203 comprises a reversible linear actuator (in this embodiment comprising a motor 1206, a screw 1207 and a nut 1208), and a translatable suture gripping means 1209. In this embodiment, the translatable suture gripping means 1209 comprises a collet-like device as illustrated in FIGS. 12*a* and 12*b*, wherein the collet-like device comprises a first tubular element 1301 having slits 1302 and an external conical surface 1303, and a second tubular element 1304 having an internal conical surface 1305. The first and second tubular elements 1301, 1304 are concentric, such that when the internal and external conical surfaces 1303, 1305 of first tubular element 1301 and second tubular element 1304 are forced together by a spring 1306, the walls of the first tubular element 1301 in the vicinity of the slits 1302 distort inward so as to grip a suture filament disposed within first tubular element 1301.

In other embodiments, different suture driving means are optionally employed, including other types of linear actuators such as pneumatic or hydraulic cylinders, motor, cable and pulley drives, piezoelectric "inchworm" type drives, and others. In still other embodiments, non-linear drive means, such as pinch rollers, are optionally used. In other embodiments, different means of gripping the suture are optionally used, such as the aforementioned pinch rollers, mechanical graspers, magnetic grippers and the like. In yet another embodiment, an optional piezoelectric inchworm actuator acts directly on the suture itself, rather than on the tubular gripping mechanism. In this way the inchworm actuator combines the functions of the actuator and the suture gripping means. Still another embodiment optionally employs a linear (or other) actuator to drive the translatable suture gripping means assembly against a linear spring such that the feeding action is accomplished by releasing the potential energy of the spring. This embodiment has the advantage of high-speed suture advancement within the end effector which leverages the time dependent stiffness of the polymer suture material to effectively push foreign material out of the suture path.

Figures 13A, 13B, 13C, 13D:
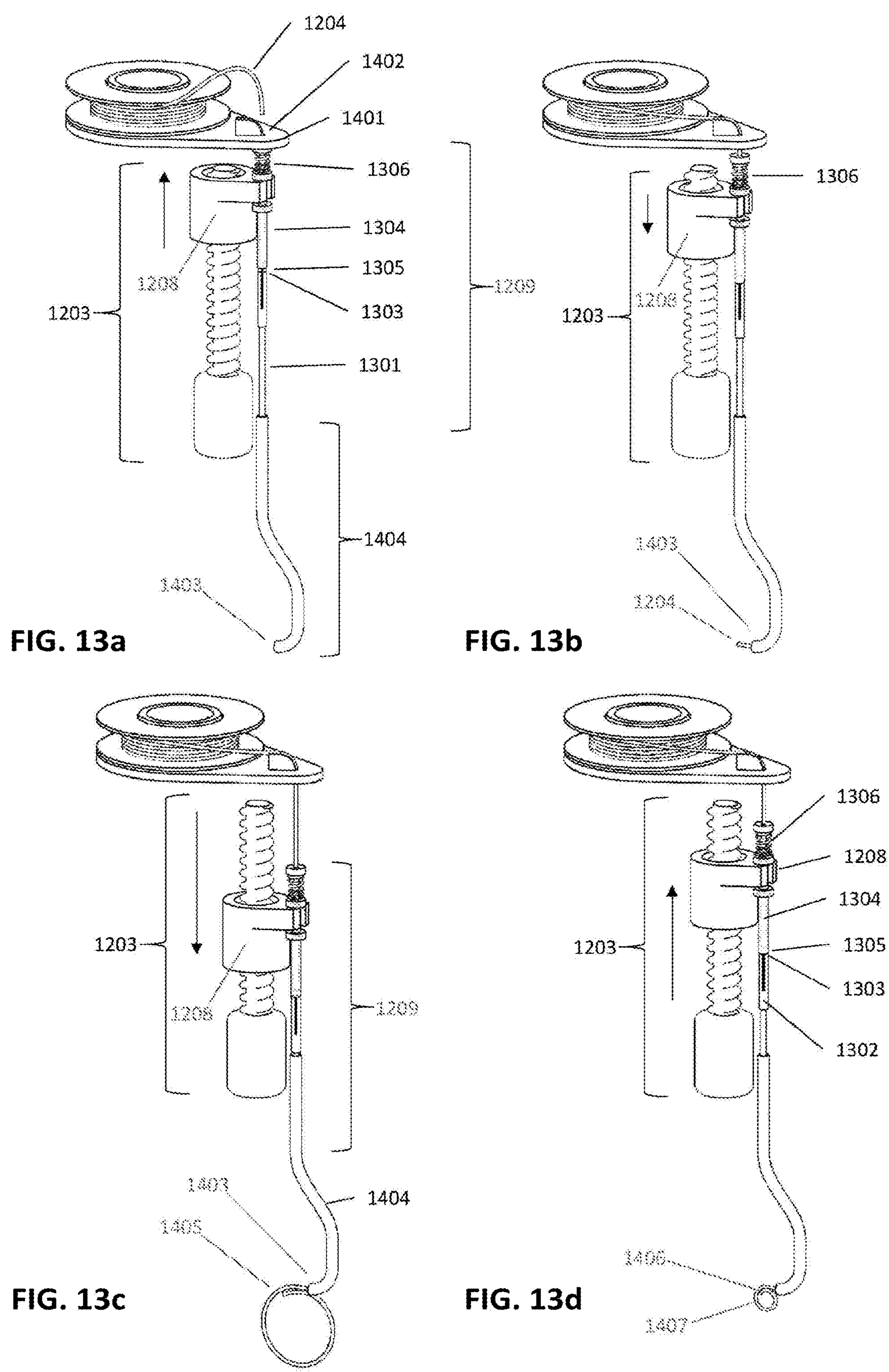
FIGS. 13*a*-13*d* are isometric schematic views of the operational steps of the device shown in FIG. 11.

Functional operation of suture feeding and tensioning mechanism 1200 is shown in FIGS. 13*a*-13*d*. FIG. 13*a* shows the initial step of the loading of the suture into mechanism 1200. The actuator nut 1208 of actuator 1203 has been driven upwards (as indicated by the arrow pointing up in this figure) to a mechanical stop 1401, compressing spring 1306. Upward movement of actuator nut 1208 causes relative movement of first tubular gripping element 1301 and second tubular gripping element 1304, separating the external conical element 1303 and internal conical element 1305, and thereby releasing the grip feature and allowing suture 1204 to be inserted through a hole 1402 in the mechanical stop 1401 that aligns with the internal lumen of the tubular gripping elements 1301 and 1304. The suture 1204 is then advanced, either by hand or by mechanical means (not shown) through the translatable suture gripping means 1209, to the distal end 1403 of an axially fixed, non-translating, flexible tube 1404 which communicates with a suturing/ligating end effector (not shown in FIGS. 13*a*-13*d*) described elsewhere in this application. Once thus loaded, suture feeding and tensioning mechanism 1200 can form many suture loops (e.g., fastening stitches or ligation stitches) and will not need to be reloaded until the suture supply 1201 runs out.

FIG. 13*b* shows suture feeding and tensioning mechanism 1200 in its "ready to stitch" configuration, in which the mechanism is ready to begin forming a suture loop. Suture 1204 has been advanced to the distal end 1403 of non-translating flexible tube 1404. The actuator nut 1208 of actuator 1203 has been driven downwards slightly, to a position allowing the spring 1306 to move tubular gripping elements 1301 and 1304 towards one another, whereby to impart a gripping force on the suture within the translatable suture gripping means 1209.

FIG. 13*c* shows the "feed" configuration of suture feeding and tensioning mechanism 1200. At the appropriate time in the suturing or ligating sequence (described elsewhere), suture 1204 will be advanced into the end effector (not shown in FIGS. 13*a*-13*d*) so as to form a loop 1405 of suture that will be welded (by a suturing/ligating end effector, not shown in FIGS. 13*a*-13*d*) to form a stitch (i.e., a suturing stitch or a ligating stitch). In FIG. 13*c*, the actuator nut 1208 of actuator 1203 has moved the translatable suture gripping means 1209 distally (i.e., downward in the orientation of FIG. 13*c*), into the close-fitting lumen of non-translating flexible tube 1404, where suture 1204 emerges at the distal end 1403 into the end effector (not shown in FIGS. 13*a*-13*d*), where suture 1204 forms a loop 1405.

FIG. 13*d* shows the "tensioning" configuration of suture feeding and tensioning mechanism 1200, in which tension is applied to the suture to tighten the suture loop. The distal end 1406 of suture 1204 has been gripped within the end effector (not shown in FIGS. 13*a*-13*d*) and the suture can now be tensioned to form a smaller, tighter stitch 1407 (which may be a suturing stitch or a ligating stitch). To accomplish this tensioning action, actuator 1203 is reversed, translating actuator nut 1208 in an upward (proximal) direction. Since the actuator nut 1208 is attached to the second (outer) tubular element 1304 and pulls the second outer tubular element 1304, and since the suture 1204 is gripped by the end effector (not shown in FIGS. 13*a*-13*d*) and the inner lumen of the first (inner) tubular element 1301 frictionally engages the suture, thereby holding first inner tubular element 1301 stationary, the external conical feature 1303 and internal conical feature 1305 separate from one another, thereby reducing the gripping force on the suture. A relationship exists between suture tension and grip force such that at a predetermined tension, the spring will compress and the suture will slip, thereby regulating the tension forces on the suture (which must be tight enough to effectively perform its surgical function and not so tight as to damage tissue or break the suture filament). Once the suture starts slipping at the desired tension, the actuator 1203 will continue to move the slipping translatable suture gripping means 1209 to the position shown in FIG. 13*b*, in which the system will be ready to form the next suture loop (e.g., a suturing stitch or a ligating stitch) after the current suture loop is welded and cut free of the end effector.

In the embodiment shown in FIGS. 11, 12*a*, 12*b* and 13*a*-13*d*, spring 1306 is of a known force which will impart a known, repeatable tension on the suture when the suture is tensioned to the point that it begins to slip. In other embodiments, the spring force is adjustable by changing the initial compression of the spring, either manually or by remote control, and either prior to use or during a surgical procedure. In still another embodiment, suture tension is automatically regulated in real time as part of a haptic feedback system that allows the surgeon to have the sensation of feeling the tension that the robotic instrument is imparting on tissue through the robotic instrument control station. The suture tension slip limit is correlated to the haptic tension felt by the surgeon so that the haptic tension remains constant as the suture beings to slip.

In an embodiment where suture feeding and tensioning mechanism 1200 is located in the proximal end of the suturing/ligating instrument (which carries the suturing/ligating end effector), the distance between the suture supply and the end effector may be quite long, therefore, one of the advantages of the embodiment shown in FIGS. 11, 12*a*, 12*b* and 13*a*-13*d* is that the first and second tubular elements 1301, 1304 can be made very long, allowing the suture supply 1201 and suture driving means 1203 to be located in the proximal end of the instrument, and the gripping means 1209 to be located distally, near the end effector. In this way, frictional losses from pushing a suture filament through a long tube are minimized, as are inaccuracies in feed length due to compressive elasticity of a long length suture being pushed through a long tube.

In practice, a robotic suturing and/or ligating instrument may be cleaned and re-sterilized after a surgical procedure, and so it can be re-used on multiple patients. However, suture filament is subject to strict sterilization and processing guidelines and may be difficult to re-sterilize once exposed to contamination. Further, suture is consumable, and a robotic suturing and/or ligating instrument may need to be re-loaded with suture after extended use. It is, therefore, desirable in some instrument embodiments that part or all of a suture feeding and tensioning system (e.g., the suture feeding and tensioning system 1200 shown in FIGS. 11, 12*a*, 12*b* and 13*a*-13*d*) be separable from the main suturing/ligating instrument and replaceable, in use. To this end, it can be desirable to provide part or all of a suture feeding and tensioning system in the form of a "suture cartridge". In one embodiment, a suture cartridge is provided comprising (i) an enclosure, the enclosure having an opening and a means for fastening the enclosure to a suturing/ligating instrument, (ii) a supply of weldable suture contained within the enclosure, and (iii) a means for advancing suture out of the opening of the enclosure and to the suturing/ligating instrument and retracting suture from the suturing/ligating instrument (e.g., for suture tensioning).

Figure 13E:
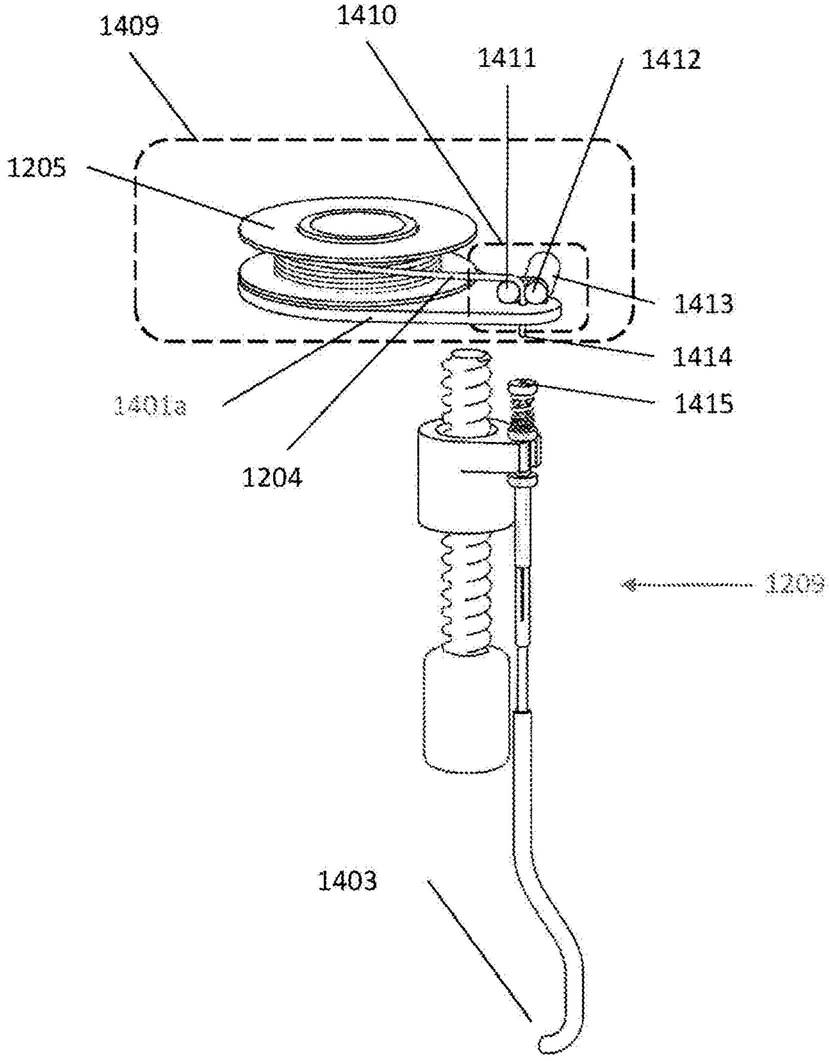
FIG. 13*e* is a schematic view showing a suture cartridge in combination with the device shown in FIG. 11.

FIG. 13*e* shows an embodiment where the supply of suture 1201 is a removable and replaceable part of the suture feeding and tensioning mechanism 1200. The ability to replace the supply of suture is of particular importance where the instrument incorporating the suture feeding and tensioning mechanism 1200 is reusable and must be re-sterilized between surgeries inasmuch as suture is difficult to re-sterilize once exposed to contamination. In the embodiment shown in FIG. 13*e*, a suture cartridge 1409 is provided. Suture cartridge 1409 comprises a length of suture 1204 on a spool 1205. Spool 1205 is mounted to a frame or housing 1401*a* (which may include the mechanical stop 1401 discussed above) and further includes a suture pre-feeding mechanism 1410. In one embodiment, the suture pre-feeding mechanism 1410 comprises first and second pinch-rollers 1411, 1412 which engage suture 1204. Pinch-rollers 1411, 1412 are driven by a source of rotational energy 1413 such as a motor or a knob turned by hand. Frame or housing 1401*a* is arranged such that it releasably attaches to the instrument incorporating the suture feeding and tensioning mechanism 1200. Frame or housing 1401*a* includes an alignment feature (not shown) that ensures that the suture end 1414 exiting the suture pre-feeding mechanism 1410 is aligned with the proximal opening 1415 in translatable suture gripping means 1209.

In practice, changing a suture cartridge 1409 in an instrument incorporating a suture feeding and tensioning mechanism 1200 will involve the steps of:

(1) driving the suture feeding and tensioning mechanism 1200 to the "Loading Position" (shown in FIG. 13*a*);

(2) releasing a mechanical latching means (not shown) to release the old suture cartridge which is to be replaced;

(3) separating the old suture cartridge (and any remaining old suture) from the instrument;

(4) positioning a new cartridge 1409 on the instrument and engaging the aforementioned mechanical latching means (not shown) to attach the new suture cartridge 1409 to the instrument and align the exiting suture end 1414 with the proximal opening 1415 in translatable suture gripping means 1209;

(5) using the suture pre-feeding mechanism 1410 to advance the exiting suture end 1414 into the translatable suture gripping means 1209 and then all the way to the distal end 1403 of the axially fixed, non-translating, flexible tube 1404 which communicates with a suturing/ligating end effector (not shown in FIGS. 13*a*-13*e*)—note that in some embodiments, this pre-feeding step is accomplished automatically through a controller operating a motorized source of rotational energy 1413 (e.g., a motor); and in other embodiments, pre-feeding is accomplished manually where the source of rotational energy 1413 comprises a hand-turned knob;

(6) moving the suture feeding and tensioning mechanism 1200 to the "Ready to Stitch" position shown in FIG. 13*b*.

The remainder of the stitch cycle is identical to that previously described and shown in FIGS. 13*c* and 13*d*.

It should be noted that other embodiments of the suture cartridge 1409 and the suture feeding and tensioning mechanism 1200 may vary in the location of elements within the system. In other words, an embodiment may have a suture cartridge 1409 comprising just a spool 1205 of suture, and the suture pre-feeding mechanism 1410 may be housed in the instrument along with the remainder of the suture feeding and tensioning mechanism 1200; or an embodiment may include a suture cartridge 1409 that includes not only the suture 1204, spool 1205, frame or housing 1401*a*, and suture pre-feeding mechanism 1410, but also the translatable suture gripping means 1209, while the reversible suture driving means 1203 remains part of the instrument; or an embodiment may include any other similar division of components, while still retaining the essence of the present invention.

Ligating End Effector for Use in Robotic Surgery

Figures 14A, 14B:
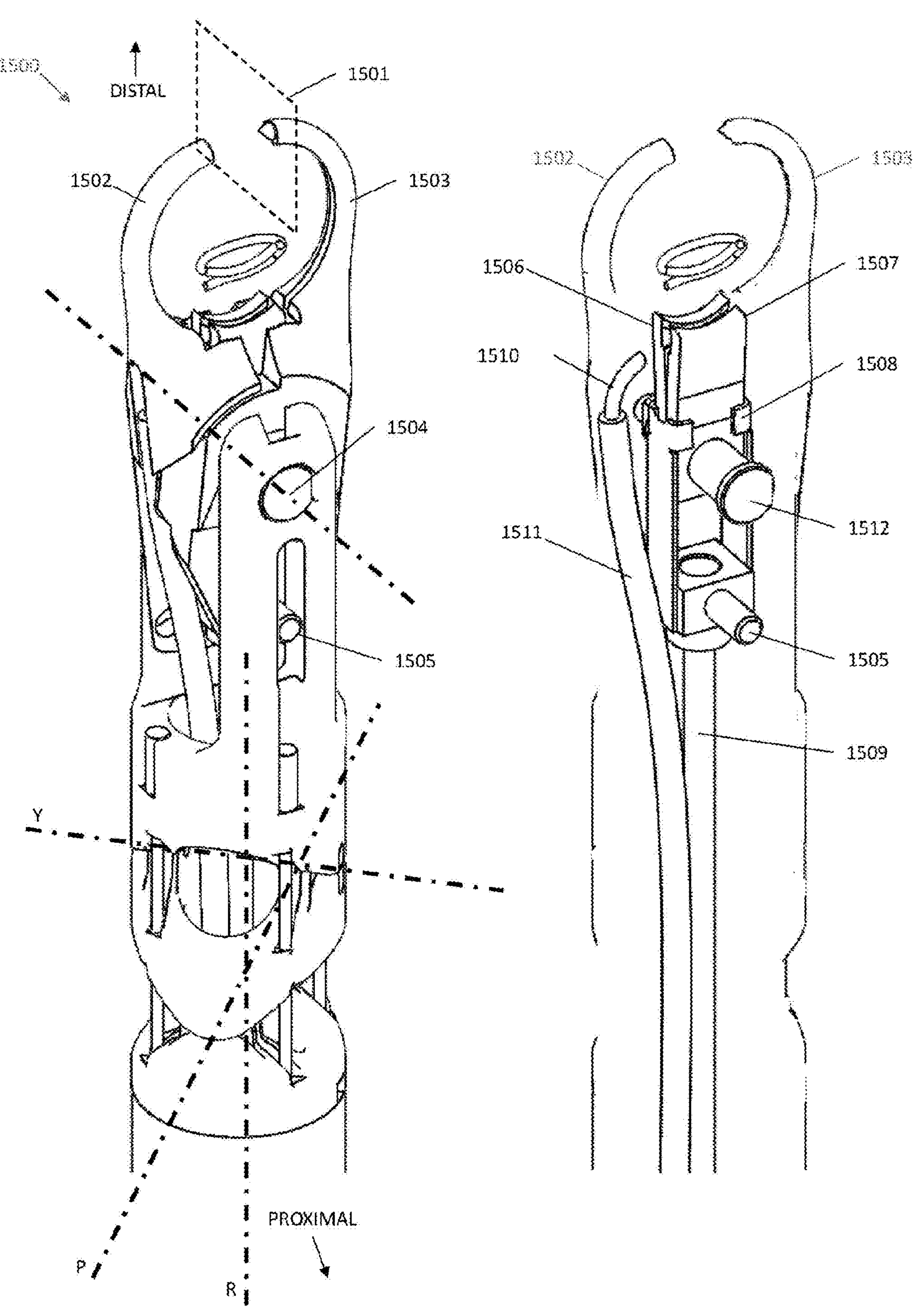
FIGS. 14*a* and 14*b* are isometric orientational views of a novel robotic instrument end effector particularly useful for vessel ligation.

FIG. 14*a* shows a novel end effector 1500 particularly suited for surgical ligation of vessels in a body. Although some embodiments of the illustrated end effector may be coupled directly to the distal end of a shaft of a surgical instrument under robotic control, FIG. 14*a* illustrates other embodiments in which a platform for this end effector 1500 includes rolling articulation joints for pitch (P) and yaw (Y) about orthogonal axes, and roll (R) about a centerline. Such a platform is commonly referred to as a "wrist" and may include one, two, three, or more, controllable mechanical degrees-of-freedom (DOFs). A fourth degree of freedom is also present, comprising a first opposing jaw member 1502 and a second opposing jaw member 1503 moving symmetrically about a plane 1501 and pivoting about a hinge axis 1504 in response to the axial movement of a drive pin 1505 engaging slots (not shown in FIG. 14*a*) in the proximal portions of the first and second jaws 1502, 1503.

FIG. 14*b* shows the arrangement and relative position of some of the internal components added to the aforementioned instrument platform to form the novel suturing and/or ligating end effector 1500. These components include a first gripper 1506 and a second gripper 1507, a gripper actuating clip 1508, a flexible actuator rod 1509, a rigid suture guide tube 1510, a flexible suture guide tube 1511, and a jaw hinge pin 1512. The function of these components will become clear in subsequent description and figures, they are presented here in outline form to orient the reader as to their location within the instrument platform.

Figures 15A, 15B, 15C, 16A, 16B:
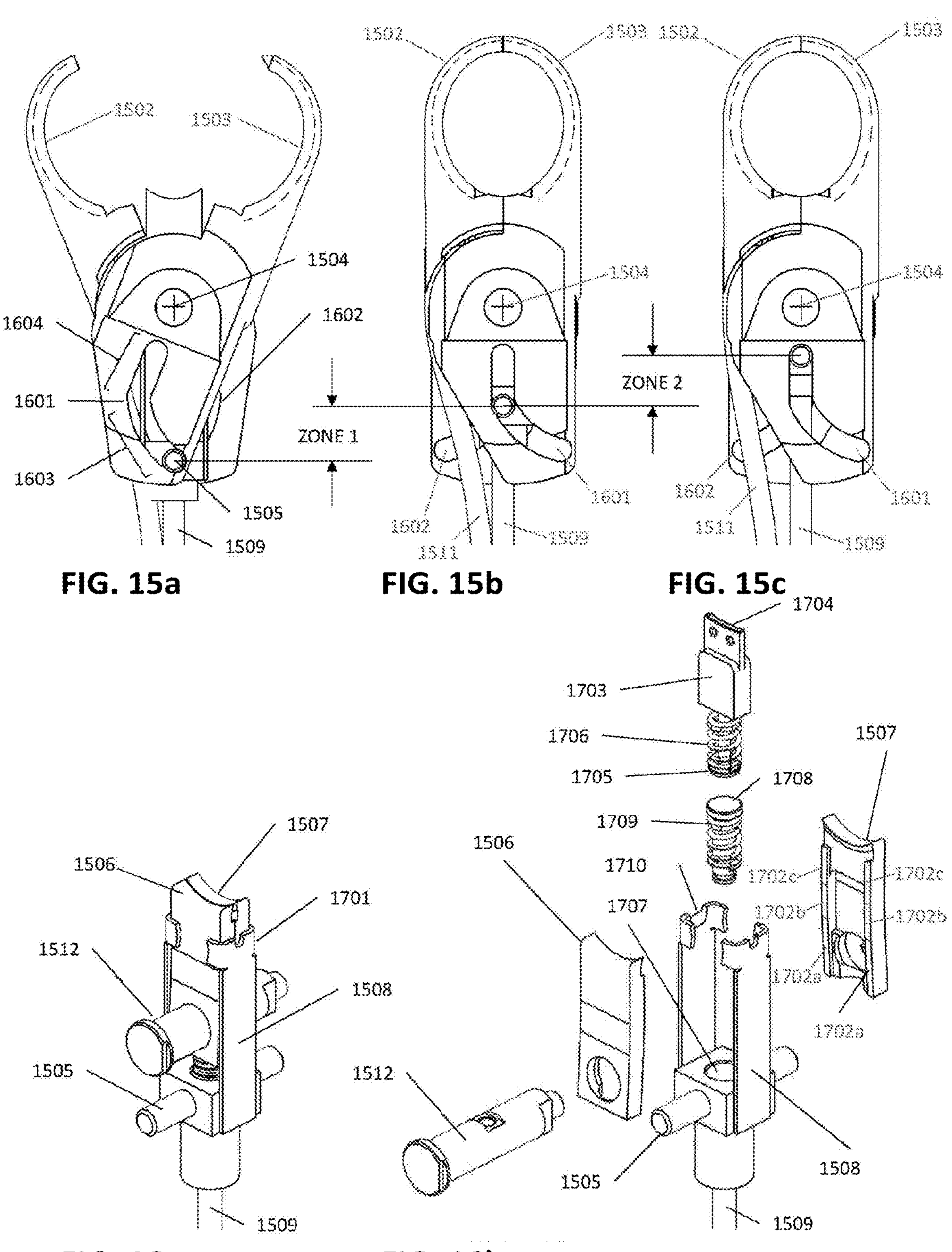
FIGS. 15*a*-15*c* are front detail views showing the relationship between actuator position and jaw movement for the end effector shown in FIGS. 14*a* and 14*b;*
FIG. 16*a* is an isometric schematic view of a novel internal mechanism for handling suture that is a part of the end effector of FIG. 14*a;*
FIG. 16*b* is an exploded schematic view of a novel internal mechanism for handling suture that is a part of the end effector of FIG. 14*a;*

FIGS. 15*a*-15*c* show the first and second opposing jaw members 1502, 1503 with selected end effector supporting structure removed. The jaw members 1502, 1503 pivot about hinge axis 1504 in response to the axial (distal-proximal along the centerline of the end effector) movement of drive pin 1505 in first jaw slot 1601 and second jaw slot 1602 (located in second jaw member 1503, behind first jaw member 1502 in FIGS. 15*a*-15*c*). The jaw slots 1601, 1602 have two geometric regions: a first slot region 1603 (shown in FIG. 15*a* on first jaw slot 1601, but also present on second jaw slot 1602) where axial (proximal/distal) movement of the drive pin 1505 causes reciprocal motion of first jaw 1502 and second jaw 1503; and a second slot region 1604 (shown in FIG. 15*a* on first jaw slot 1601, but also present on second jaw slot 1602) where axial movement of drive pin 1505 does not result in jaw movement (the jaws instead remaining in a closed orientation relative to one another, as seen in FIGS. 15*b* and 15*c*). It can be seen, therefore, that over the length of axial travel of the drive pin 1505 in slots 1601 and 1602, there are two zones: Zone 1 from the proximal most position of drive pin 1505 to approximately the midpoint of its range of movement, in which the movement of drive pin 1505 moves jaw members 1502, 1503 (see FIGS. 15*a* and 15*b*); and Zone 2 from approximately the midpoint of drive pin range of travel to the distalmost drive pin position, in which no jaw movement occurs (see FIGS. 15*b* and 15*c*). In this way, it can be seen that a single degree of freedom (i.e., axial movement of actuator rod 1509 in slots 1601, 1602) can be used to accomplish multiple functions by operating in different zones.

FIG. 16*a* shows an assembly of components for the handling, welding, trimming and release of welded suture loops for the formation of surgical stitches for suturing and ligating. First gripper 1506 and second gripper 1507 are restrained from axial movement by hinge pin 1512. Gripper actuating clip 1508 is connected to flexible actuator rod 1509 which moves axially in response to user and/or computer control inputs. Pinching features 1701 on gripper actuating clip 1508 slide on first gripper 1506 and second gripper 1507 and pinch the gripper pair together at different locations along their length as the flexible actuator rod 1509 moves. In other words, first gripper 1506 and second gripper 1507 can be moved towards or away from one another by axial movement of flexible actuator rod 1509.

FIG. 16*b* shows an exploded view of the assembly in FIG. 16*a*. Facets 1702, three per side (1702*a*, 1702*b*, 1702*c*), are present on the inside opposing edges of the first and second grippers 1506, 1507 such that the grippers rock angularly against each other depending on where along their length they are pinched by gripper actuator 1508. Sandwiched between the grippers 1506, 1507 is an electrode 1703 with an exposed conductive surface 1704 at its distal end. Electrode 1703 is connected to a switched electrical current source (not shown) by a flexible wire (not shown). A first protruding headed pin 1705 extends proximally from electrode 1703, and a light spring 1706 acts against the head 1706*a* (see FIGS. 17*a*-17*f*) of pin 1705 and a counterbore 1706*b* (see FIGS. 17*a*-17*f*) in the proximal side of hinge pin 1512 to maintain a light proximal (downward) force on the electrode 1703. Housed within a central bore 1707 in gripper actuator clip 1508 is a second headed pin 1708 which has its head 1708*a* supported with a heavy spring 1709 which engages an annular shoulder 1709*a* set at the base of central bore 1707. Gripper actuator clip 1508 includes a sharpened edge 1710 on one side.

FIGS. 17*a*-17*f* are section views of the assembly shown in FIGS. 16*a* and 16*b* showing sequential functional aspects of this assembly.

Figures 17A, 17B, 17C, 17D, 17E, 17F:
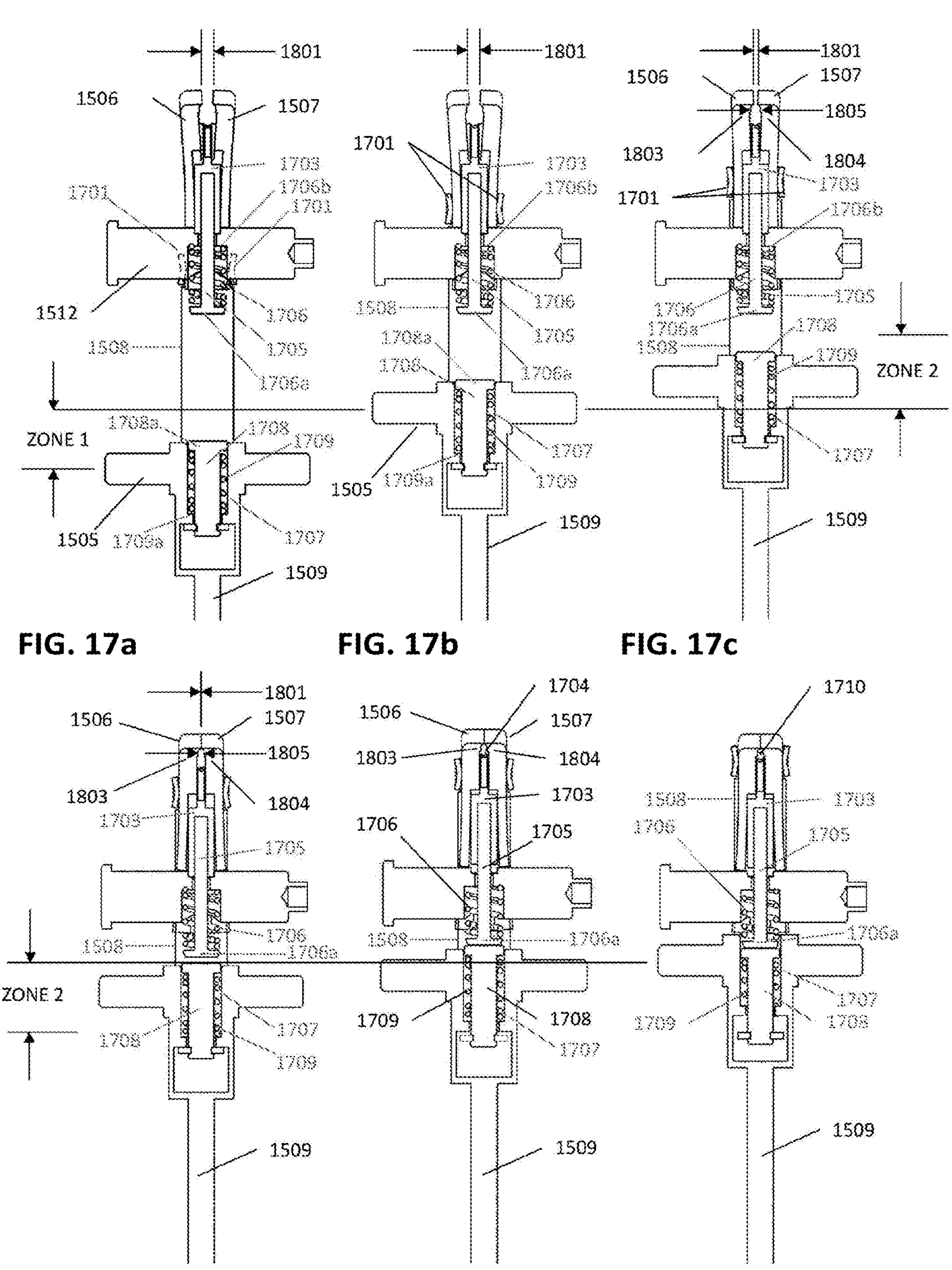
FIGS. 17*a*-17*f* are a series schematic side section views showing the sequence of operation of the suture handling mechanism of FIGS. 16*a* and 16*b*.
Figures 18A, 18B, 18C:
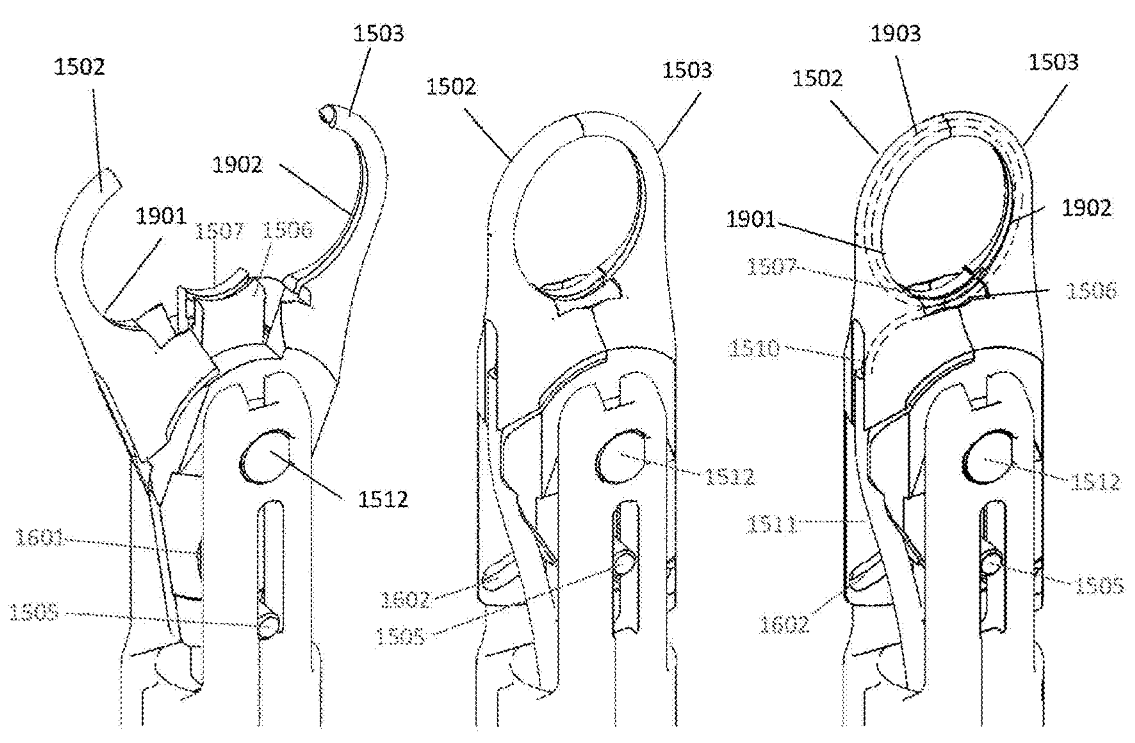
FIGS. 18*a*-18*f* are isometric schematic views showing the operational steps of the ligating instrument of FIGS. 14*a* and 14*b* from the user's perspective.

FIG. 18*a* shows flexible actuator rod 1509 in its proximal most position. Drive pin 1505 engages first jaw slot 1601 and second jaw slot 1602 (neither of which are shown in this view) to position first jaw 1502 and second jaw 1503 (neither of which are shown in this view) in their fully open position (i.e., the position shown in FIG. 15*a*). Gripper actuator clip pinching features 1701 (shown in phantom in FIG. 17*a*, behind hinge pin 1512) pinch first gripper 1506 and second gripper 1507 on their proximal most edge, rocking the grippers on their proximal most of three sets of opposing facets 1702*a* (not shown in FIG. 17*a*) to create a gap 1801 at the distal edges of first gripper 1506 and second gripper 1507. In this component orientation, gripper gap 1801 is wider than the diameter of a suture filament.

FIG. 17*b* shows flexible actuator rod 1509 moved distally so that drive pin 1505 (connected to actuator rod 1509) is also moved distally to the distal end of Zone 1 (i.e., the jaw movement zone which is shown in FIG. 15*b*). Pinching features 1701, which are carried by gripper actuator clip

1508 (which is also connected to flexible actuator rod 1509) have moved the same distance distally by sliding along the edges of grippers 1506 and 1507, however, the pinchers 1701 are still in the region of the proximal most of the three sets of gripper facets 1702*a* (not shown in FIG. 17*b*), and therefore the wide gripper gap 1801 remains unchanged. An important aspect of this embodiment is the ability to use one actuator (one degree of freedom) to control multiple functions. It can be seen that when the actuator rod 1509 moves drive pin 1505 within Zone 1, the jaws 1502, 1503 move according to user input and the assembly shown in FIGS. 16*a* and 16*b* remain unaffected. When the actuator rod 1509 moves drive pin 1505 in Zone 2, the assembly shown in FIGS. 16*a* and 16*b* is activated while the jaws 1502, 1503 remain closed and stationary.

FIG. 17*c* shows flexible actuator rod 1509, as well as connected drive pin 1505 and pincher features 1701, driven distally, so that drive pin 1505 is in the proximal region of Zone 2 (i.e., the position shown in FIG. 15*b*). Pinching features 1701 have slid distally along the edges of grippers 1506 and 1507 to roughly mid-way along their length, thereby rocking the middle of the three gripper facets 1702*b* (not shown in FIG. 17*c*) into contact. As a result, the distal surfaces of grippers 1506, 1507 have moved toward each other to reduce the width of gripper gap 1801 so that it is less than one suture diameter wide (but still greater than zero). First stepped surface 1803 and second stepped surface 1804 on the inner surfaces of grippers 1506 and 1507, respectively, form a step gap 1805 (FIG. 17*c*) that has a width that is greater than one suture diameter and less than 2 suture diameters. This gap arrangement 1805 allows suture to be threaded between first stepped surface 1803 and second stepped surface 1804 without restriction, while not being able to escape through the now-reduced gap 1801.

FIG. 17*d* shows actuator rod 1509 moved still further distally. Pinching features 1701 on gripper actuator clip 1508 now pinch first gripper 1506 and second gripper 1507 along the distal third of their length, thereby rocking the grippers onto the distalmost of the three sets of edge facets 1702*c* (not shown in FIG. 17*d*), further narrowing distal gripper gap 1801, and narrowing step gap 1805 to a width of less than one suture diameter, thereby allowing stepped surfaces 1803 and 1804 to grasp the distal end of a suture loop threaded between the grippers 1506, 1507. Once the distal end of the suture loop is grasped by grippers 1506, 1507, the suture feed mechanism (e.g., the suture feed mechanism shown in FIGS. 11, 12*a*, 12*b* and 13*a*-13*d*) may be reversed and the suture loop tensioned to the desired force.

Figures 18D, 18E, 18F:
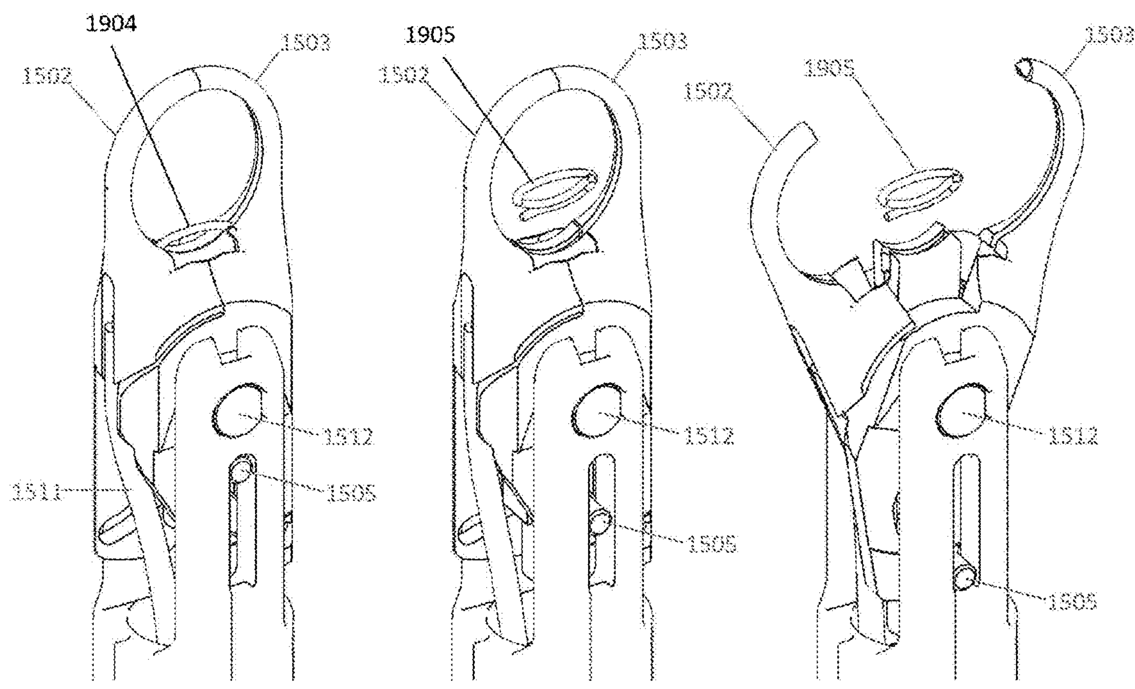

FIG. 18*e* shows actuator rod 1509 moved still further distally. It can be seen that second headed pin 1708 (held distally under the force of heavy spring 1709) is in contact with first headed pin 1705 (held proximally under the light force of light spring 1706), thereby causing first pin 1705 and connected electrode 1703 to move distally (i.e., upwards in the direction of use shown in FIG. 17*e*) and bringing distal conductive electrode surface 1704 into contact with overlapping suture segments (not shown in FIG. 17*e*) held in the vicinity of step gap 1805. When the overlapping suture segments block further distal movement of electrode 1703, continued distal movement of actuator rod 1509 compresses heavy spring 1709. The force of the electrode 1703 bearing on the overlapping suture segments (held between grippers 1506 and 1507) is now equal to the compressed spring force of heavy spring 1709 minus the compressed spring force of light spring 1706. In one embodiment, grippers 1506 and 1507 are made of a conductive material and are connected to one pole of a power source (e.g., electrical ground) and conductive surface 1704 of electrode 1703 is connected to the switched opposite pole of the same power source. In a preferred embodiment, grippers 1506 and 1507 are made of a non-conducting material (e.g., a ceramic) and stepped surfaces 1803 and 1804 of grippers 1506 and 1507 have electrically conductive cladding connected to one pole of a power source and electrically conductive surface 1704 of electrode 1703 is connected to the switched opposite pole of the same power source, such that controlled electrical current (triggered by external means) can be caused to flow between overlapping segments of a suture loop, thereby welding the overlapping segments of suture loop together. After welding, a dwell time of up to ½ second may be required to allow the melted polymer in the weld zone to solidify before moving on to the next step in the sequence.

FIG. 17*f* shows actuator rod 1509 moved to its distalmost position. Sharpened edge 1710 (far side of assembly, shown also in FIG. 16*b*) of actuator clip 1508 slides distally with movement of the actuator rod 1509 so that sharpened edge 1710 extends across the opening of rigid suture guide tube 1510 (shown in FIG. 14*b*), thereby trimming the welded suture loop from the suture supply. In the final step of the sequence, actuator rod 1509 is moved to its middle (i.e., the distal end of Zone 1 as shown in FIG. 15*c*) position, returning to the configuration shown in FIG. 17*b*, thereby re-opening distal gripper gap 1801 to a width which is greater than one suture diameter, and thereby releasing the tensioned, welded, trimmed suture loop from the end effector. The user is then free to manually open first jaw 1502 and second jaw 1503 (not shown in FIG. 17*f*), thereby returning to the configuration of FIG. 17*a* to reposition the end effector for the next stitch.

FIGS. 18*a*-18*e* show an embodiment of the ligating device 1500 in use, as seen from the user's perspective.

FIG. 18*a* shows first jaw 1502 and second jaw 1503, with first inward-facing groove 1901 and second inward-facing groove 1902, respectively. First jaw 1502 and second jaw 1503 pivot about hinge pin 1512. Drive pin 1505 is in its fully proximal position, so the jaws are fully open (i.e., in the position shown in FIG. 15*a*).

FIG. 18*b* shows drive pin 1505 in its mid-stroke position (i.e., at the distal end of Zone 1/beginning of Zone 2), so the jaws are fully closed (i.e., in the position shown in FIG. 15*b*). Prior to initiating the loop-forming sequence, the jaws 1502, 1503 are free to open and close in response to inputs from the user at a surgical robotic control console or other input device. All surgeon-initiated jaw movements occur with drive pin 1505 operating in Zone 1. In order to ligate (tie-off) a blood vessel or other tubular anatomic structure (not shown), the surgeon will first dissect the connective tissue adhering to the vessel to obtain access to its full circumference. The surgeon will then close the jaws 1502, 1503 around the vessel to be ligated under manual control and position the instrument where they want to place a stitch (e.g., a ligating loop). When ready, the user will initiate the loop-forming process by generating a control command, such as by depressing a footswitch, pressing a button, issuing a voice command or taking similar action to initiate the loop-formation sequence.

FIG. 18*c* shows the first step in the automated or semi-automated stitching process controlled by a computer or another type of sequence controller. A loop of suture 1903 (shown in phantom line inside jaws 1502, 1503) is advanced (i) through suture guide tubes 1511 and 1510, (ii) through the aforementioned gap 1805 (formed between first gripper 1506 and second gripper 1507), with gap 1805 having a width which is greater than one suture diameter but less than two suture diameters (see FIG. 17*c*), (iii) around aligned inward-facing grooves 1901 and 1902 formed in jaws 1502 and 1503, respectively, and (iv) back into the gap 1805 formed between grippers 1506, 1507, such that the distal end of the suture loop ends up between stepped surfaces 1803 and 1804 of grippers 1506, 1507. Actuator rod 1509 will then advance to the position shown in FIG. 17*d*, causing gripper actuator clip 1508 to move upward, such that grippers 1506, 1507 grasp the distal end of the suture loop. The suture feed mechanism is then reversed to tension the suture loop around the vessel which is to be ligated. In one embodiment, tensioning is part of the automated sequence and the tension value is pre-determined. In another embodiment, the surgeon selects the tension value or tensions the stitch using haptic feedback through a tactile action at the control console.

FIG. 18*d* shows the tensioned suture loop 1904 in the instrument as it would appear during the welding (see FIG. 17*e*) and trimming (see FIG. 17*f*) steps.

FIG. 18*e* shows the last step of the automated process, in which the actuator rod returns to the release position (see FIG. 17*b*), such that grippers 1506, 1507 open back up to release suture loop 1905 from the end effector. In FIG. 18*e*, the completed stitch 1905 has been released and control of the jaws 1502, 1503 has now been returned to the user. In practice, unless a manual suture tensioning step is included, the automated loop formation process should take less than one second to complete the stitch.

FIG. 18*f* shows the jaws 1502, 1503, having been manually opened by the user, releasing the ligated vessel and ready to reposition for the next suture loop.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An apparatus for applying suture to tissue, wherein the suture comprises a biocompatible, electrically conductive thermoplastic material and has a diameter, the apparatus comprising:

a shaft having a distal end and a proximal end;

a jaw assembly coupled to the shaft, the jaw assembly comprising:

a first jaw member comprising a first connector, and a second jaw member comprising a second connector;

a gripping assembly coupled to the shaft, the gripping assembly comprising:

a first gripper comprising a first gripping surface, and a second gripper comprising a second gripping surface;

an electrode assembly coupled to the shaft, the electrode assembly comprising an electrode movable toward and away from the first and second gripping surfaces; and an actuation assembly operably coupled to the jaw assembly, the gripping assembly, and the electrode assembly, the actuation assembly comprising:

an actuation member movably mounted to the shaft and movable between a first position and a second position relative to the shaft, and a drive member mounted to the actuation member and coupled to the first connector of the first jaw member and the second connector of the second jaw member, wherein movement of the actuation member from the first position toward the second position relative to the shaft causes, sequentially:

(a) at least one of the first and second jaw members of the jaw assembly to move from an initial spaced apart position toward each other and toward a closed position;

(b) at least one of the first and second grippers to move the first and second gripping surfaces from an initial spaced apart position toward each other toward a gripping position; and (c) the electrode to move from an initial position away from the first and second gripping surfaces toward the first and second gripping surfaces.

2. The apparatus according to claim 1, wherein subsequent movement of the actuation member from the second position toward the first position causes, sequentially:

(d) the electrode to move away from the first and second gripping surface toward the initial position;

(e) at least one of the first and second grippers to move the first and second gripping surfaces away from each other and toward the initial spaced apart position; and (f) at least one of the first and second jaw members of the jaw assembly to move away from each other toward the initial spaced apart position.

3. The apparatus according to claim 2, further comprising a cutter blade, wherein movement of the actuation member from the first position toward the second position relative to the shaft further causes movement of the cutter blade in response to movement of the at least one of the first gripping surface and the second gripping surfaces away from each other.

4. The apparatus according to claim 1, wherein the first connector is a first slot and the second connector is a second slot.

5. The apparatus according to claim 4, wherein the first slot comprises a curved portion and a straight portion, and further wherein the second slot comprises a curved portion and a straight portion.

6. The apparatus according to claim 1, wherein the gripping assembly further comprises a gripper clip engageable with the first gripper and the second gripper.

7. The apparatus according to claim 6, further comprising a cutter blade mounted to and moveable with the gripper clip.

8. The apparatus according to claim 1, wherein the electrode assembly is configured to generate an electric potential between the electrode and at least one of the first and second gripping surfaces.

9. The apparatus according to claim 1, wherein the first jaw member comprises a first passageway and the second jaw member comprises a second passageway, and wherein in the closed position, the first and second passageways form a continuous passageway configured to receive a loop of suture.

10. The apparatus according to claim 9, wherein the first passageway in the first jaw member is a groove, and further wherein the second passageway in the second jaw member is a groove.

11. The apparatus according to claim 1, wherein the electrode assembly comprises:

a first electrode;

a second electrode; and a spring biasing the first electrode and the second electrode toward engagement with the gripping assembly.

12. The apparatus of claim 11, wherein the spring biases the first electrode and the second electrode to maintain pressure on a contact region of the suture between a first end of the suture and second end of the suture.

13. The apparatus according to claim 11, further comprising:

a first pin comprising a protruding head, the first pin extending proximally from one of the first and second electrodes; and a hinge pin coupled to the jaw assembly, the first jaw member and the second jaw member pivotable relative to each other about the hinge pin.

14. The apparatus of claim 13, wherein:

the hinge pin includes a counterbore, the hinge pin restrains axial movement of the first gripper and the second gripper, and the spring engages the head of the first pin and the counterbore and exerts a proximally directed biasing force on the first electrode.

15. The apparatus of claim 13, further comprising:

a second pin including a head coupled to a second spring, wherein the second spring exerts a biasing force on the second pin, wherein in a state of contact between the first pin and the second pin, the biasing force of the second spring causes the electrode to move toward the first and second gripping surfaces.

16. The apparatus of claim 1, wherein the actuation member comprises a rod.

17. A method for actuation of a suturing device for applying suture to tissue, comprising:

moving an actuation member of the suturing device and thereby driving movement of a jaw assembly, a gripper assembly, and an electrode assembly operably coupled to the actuation member, wherein movement of the actuation member in a first direction causes, sequentially:

(a) at least one of a first and second jaw of the jaw assembly to move from an initial spaced apart position toward the other of the at least one first and second jaw and toward a closed position;

(b) at least one of first and second grippers of the gripping assembly to move first and second gripping surfaces from an initial spaced apart position toward each other to a gripping position; and (c) an electrode of the electrode assembly to move from an initial position spaced from the first and second gripping surfaces toward the first and second gripping surfaces to a welding position in which the electrode is configured to generate an electric potential with one of the first and second grippers.

18. The method according to claim 17, wherein subsequent movement of the actuation member in a second direction opposite the first direction causes, sequentially:

(d) the electrode to move from its welding position toward the initial position spaced from the first and second gripping surfaces;

(e) at least one of the first and second grippers to move the first and second gripping surfaces toward the initial spaced apart position; and (f) at least one of the first and second jaws of the jaw assembly toward the initial spaced apart position.

19. The method according to claim 18, wherein movement of the actuation member drives movement of a drive component coupled to the first jaw and the second jaw.

20. The method according to claim 19, wherein the drive component comprises a pin received in a first slot of the first jaw and a second slot of the second jaw.

21. The method according to claim 17, wherein movement of the actuation member further causes a cutter blade to move from an initial position spaced from the first and second gripping surfaces toward the first and second gripping surfaces to a cutting position after step (c).

22. The method according to claim 17, wherein movement of the actuation member in the first direction further causes movement of a plurality of pinching features along the first gripper and the second gripper to move the first and second gripping surfaces toward the gripping position at step (b).

23. The method according to claim 17, wherein movement of the actuation member in the first direction further comprises:

causing contact between a first pin coupled to an electrode at a first spring and a second pin within the gripper assembly, wherein the second pin is coupled to a second spring; and causing movement of the electrode toward the welding position at step (c).

24. The method according to claim 17, wherein movement of an electrode of the electrode assembly into the welding position further comprises maintaining the electrode in a biased position to maintain pressure on a contact point.

* * * * *